US011849709B2

(12) United States Patent
Ostertag et al.

(10) Patent No.: US 11,849,709 B2
(45) Date of Patent: *Dec. 26, 2023

(54) GENETICALLY MODIFIED RAT MODELS FOR SEVERE COMBINED IMMUNODEFICIENCY (SCID)

(71) Applicant: Hera Testing Laboratories, Inc., Lexington, KY (US)

(72) Inventors: Eric M. Ostertag, Del Mar, CA (US); John Stuart Crawford, Lexington, KY (US); Joseph Ruiz, Cary, NC (US)

(73) Assignee: Hera Testing Laboratories, Inc., Lexington, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/553,463

(22) Filed: Dec. 16, 2021

(65) Prior Publication Data

US 2022/0167598 A1 Jun. 2, 2022

Related U.S. Application Data

(63) Continuation of application No. 17/335,568, filed on Jun. 1, 2021, which is a continuation of application No. 15/810,272, filed on Nov. 13, 2017, now Pat. No. 11,089,765, which is a continuation of application No. 15/070,275, filed on Mar. 15, 2016, now abandoned, which is a continuation of application No. 13/391,307, filed as application No. PCT/US2010/040768 on Jul. 1, 2010, now Pat. No. 9,314,005.

(60) Provisional application No. 61/222,327, filed on Jul. 1, 2009.

(51) Int. Cl.
| | |
|---|---|
| *A01K 67/027* | (2006.01) |
| *C12N 9/12* | (2006.01) |
| *C12N 9/14* | (2006.01) |
| *C12N 9/22* | (2006.01) |
| *C12N 15/85* | (2006.01) |
| *C12N 15/87* | (2006.01) |
| *C12N 15/90* | (2006.01) |

(52) U.S. Cl.
CPC ........ *A01K 67/0276* (2013.01); *C12N 9/1205* (2013.01); *C12N 9/14* (2013.01); *C12N 9/22* (2013.01); *C12N 15/8509* (2013.01); *C12N 15/87* (2013.01); *C12N 15/907* (2013.01); *A01K 2217/05* (2013.01); *A01K 2217/054* (2013.01); *A01K 2217/056* (2013.01); *A01K 2217/20* (2013.01); *A01K 2217/206* (2013.01); *A01K 2227/105* (2013.01); *A01K 2267/0331* (2013.01); *A01K 2267/0387* (2013.01); *C12N 2015/8536* (2013.01)

(58) Field of Classification Search
None
See application file for complete search history.

(56) References Cited

U.S. PATENT DOCUMENTS

| | | |
|---|---|---|
| 4,670,388 A | 6/1987 | Rubin et al. |
| 4,736,866 A | 4/1988 | Leder et al. |
| 4,870,009 A | 9/1989 | Evans et al. |
| 4,873,191 A | 10/1989 | Wagner et al. |
| 4,897,355 A | 1/1990 | Eppstein et al. |
| 4,945,050 A | 7/1990 | Sanford et al. |
| 4,949,317 A | 8/1990 | McQuitty et al. |
| 4,959,317 A | 9/1990 | Sauer |
| 5,489,742 A | 2/1996 | Hammer et al. |
| 5,569,824 A | 10/1996 | Donehower et al. |
| 5,654,182 A | 8/1997 | Wahl et al. |
| 5,719,055 A | 2/1998 | Cooper |
| 5,792,924 A | 8/1998 | Yoder et al. |
| 6,207,876 B1 | 3/2001 | Kellems et al. |
| 6,218,185 B1 | 4/2001 | Shirk et al. |
| 6,225,121 B1 | 5/2001 | Savakis et al. |
| 6,432,639 B1 | 8/2002 | Lichter et al. |
| 6,475,798 B2 | 11/2002 | Fogarty et al. |
| 6,489,458 B2 | 12/2002 | Hackett et al. |
| 6,790,629 B2 | 9/2004 | Julius et al. |
| 6,962,810 B2 | 11/2005 | Fraser et al. |
| 6,989,441 B2 | 1/2006 | Curtis |
| 7,148,203 B2 | 12/2006 | Hackett et al. |
| 7,223,557 B2 | 5/2007 | Lee et al. |
| 7,262,336 B2 | 8/2007 | Young et al. |
| 7,504,223 B2 | 3/2009 | Srivastava et al. |
| 7,947,448 B2 | 5/2011 | Couillard-Despres et al. |

(Continued)

FOREIGN PATENT DOCUMENTS

| | | |
|---|---|---|
| CN | 105145486 A | 12/2015 |
| EP | 1642970 A1 | 4/2006 |

(Continued)

OTHER PUBLICATIONS

Usui J, Kobayashi T, Yamaguchi T et al. Generation of kidney from pluripotent stem cells via blastocyst complementation. Am. J. Pathol. 180(6), 2417-2426 (2012).*

Kobayashi T, Yamaguchi T, Hamanaka S et al. Generation of rat pancreas in mouse by interspecific blastocyst injection of pluripotent stem cells. Cell 142(5), 787-799 (2010).*

Kitada et al., 2007; Nature Methods pp. 131-133; Transposon-tagged mutagenesis in the rat.*

Gary et al Humanized organs in gene-edited animals Regen. Med. (2016) 11(7), 617-619.*

Gene knockout—Wikipedia The Free Encyclopedia . downloaded Mar. 1, 2023; pp. 1-7.*

(Continued)

*Primary Examiner* — Maria G Leavitt
(74) *Attorney, Agent, or Firm* — COOLEY LLP

(57) ABSTRACT

This invention relates to the engineering of animal cells, preferably mammalian, more preferably rat, that are deficient due to the disruption of tumor suppressor gene(s) or gene product(s). In another aspect, the invention relates to genetically modified rats, as well as the descendants and ancestors of such animals, which are animal models of human cancer and methods of their use.

21 Claims, 6 Drawing Sheets

Specification includes a Sequence Listing.

(56) References Cited

U.S. PATENT DOCUMENTS

| | | |
|---|---|---|
| 7,985,739 B2 | 7/2011 | Kay et al. |
| 7,998,993 B2 | 8/2011 | Perner et al. |
| 8,084,616 B2 | 12/2011 | Gomtsyan et al. |
| 8,137,907 B2 | 3/2012 | Zender et al. |
| 8,558,055 B2 | 10/2013 | Ostertag et al. |
| 8,771,945 B1 | 7/2014 | Zhang |
| 8,795,965 B2 | 8/2014 | Zhang |
| 8,865,406 B2 | 10/2014 | Zhang et al. |
| 8,889,356 B2 | 11/2014 | Zhang |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,206,404 B2 | 12/2015 | Cui et al. |
| 9,314,005 B2 | 4/2016 | Ostertag et al. |
| 9,902,971 B2 | 2/2018 | Frendewey et al. |
| 11,089,765 B2 | 8/2021 | Ostertag et al. |
| 2002/0016975 A1 | 2/2002 | Hackett et al. |
| 2002/0028513 A1 | 3/2002 | Fogarty et al. |
| 2002/0072101 A1 | 6/2002 | Gaughan et al. |
| 2002/0088017 A1 | 7/2002 | Kellems et al. |
| 2002/0132301 A1 | 9/2002 | Curtis |
| 2003/0049728 A1 | 3/2003 | Julius et al. |
| 2003/0120049 A1 | 6/2003 | Schultz et al. |
| 2004/0025197 A1 | 2/2004 | Young et al. |
| 2004/0197910 A1 | 10/2004 | Cooper et al. |
| 2005/0158827 A1 | 7/2005 | Curtis |
| 2006/0026699 A1 | 2/2006 | Largaespada et al. |
| 2006/0194750 A1 | 8/2006 | Shuster et al. |
| 2007/0022485 A1 | 1/2007 | Takeda et al. |
| 2007/0022486 A1 | 1/2007 | Allen |
| 2007/0044162 A1 | 2/2007 | Riess et al. |
| 2007/0209083 A1 | 9/2007 | Thiam et al. |
| 2008/0168571 A1 | 7/2008 | Young et al. |
| 2008/0193375 A1 | 8/2008 | Wu et al. |
| 2009/0131302 A1 | 5/2009 | Pasricha et al. |
| 2010/0287628 A1 | 11/2010 | Ostertag et al. |
| 2011/0035816 A1 | 2/2011 | Ostertag et al. |
| 2011/0145936 A1 | 6/2011 | Ostertag et al. |
| 2012/0151609 A1 | 6/2012 | Ostertag et al. |
| 2012/0177577 A1 | 7/2012 | Ostertag et al. |
| 2014/0041063 A1 | 2/2014 | Ostertag et al. |
| 2014/0304844 A1 | 10/2014 | Jamieson et al. |
| 2015/0047061 A1 | 2/2015 | Murphy et al. |
| 2015/0052623 A1 | 2/2015 | Crawford et al. |
| 2015/0052624 A1 | 2/2015 | Ostertag et al. |
| 2015/0283270 A1 | 10/2015 | An et al. |
| 2016/0046959 A1 | 2/2016 | Landel et al. |
| 2016/0174532 A1 | 6/2016 | Ostertag et al. |
| 2016/0174533 A1 | 6/2016 | Ostertag et al. |
| 2016/0174534 A1 | 6/2016 | Ostertag et al. |
| 2016/0302397 A1 | 10/2016 | Ostertag et al. |
| 2018/0295819 A1 | 10/2018 | Ostertag et al. |
| 2021/0092942 A1 | 4/2021 | Crawford et al. |

FOREIGN PATENT DOCUMENTS

| | | |
|---|---|---|
| JP | 2006141228 A | 6/2006 |
| WO | WO-9707668 A1 | 3/1997 |
| WO | WO-9707669 A1 | 3/1997 |
| WO | WO-0015650 A1 | 3/2000 |
| WO | WO-0244210 A2 | 6/2002 |
| WO | WO-2005003342 A1 | 1/2005 |
| WO | WO-2005020683 A1 | 3/2005 |
| WO | WO-2005053512 A2 | 6/2005 |
| WO | WO-2007053637 A2 | 5/2007 |
| WO | WO-2008015403 A1 | 2/2008 |
| WO | WO-2009037707 A2 | 3/2009 |
| WO | WO-2009050484 A1 | 4/2009 |
| WO | WO-2009055629 A2 | 4/2009 |
| WO | WO-2009055749 A1 | 4/2009 |
| WO | WO-2009061152 A2 | 5/2009 |
| WO | WO-2009071334 A2 | 6/2009 |
| WO | WO-2009072882 A1 | 6/2009 |
| WO | WO-2009084034 A2 | 7/2009 |
| WO | WO-2010124200 A2 | 10/2010 |
| WO | WO-2011002988 A1 | 1/2011 |
| WO | WO-2011011678 A2 | 1/2011 |
| WO | WO-2011014721 A2 | 2/2011 |
| WO | WO-2011017518 A2 | 2/2011 |
| WO | WO-2011022634 A2 | 2/2011 |
| WO | WO-2012129198 A1 | 9/2012 |
| WO | WO-2013032918 A1 | 3/2013 |
| WO | WO-2015065919 A1 | 5/2015 |

OTHER PUBLICATIONS

Acsadi, G. et al., "Human dystrophin expression in mdx mice after intramuscular injection of DNA constructs," Nature, vol. 352, (1991) pp. 815-818.

"Advisory Action" in Request for Ex Parte Reexamination of U.S. Pat. No. 8,558,055 (U.S. Appl. No. 90/013,858), dated Nov. 24, 2017, 5 pages.

Advisory Action in Request for Ex Parte Reexamination of U.S. Pat. No. 8,772,964 (U.S. Appl. No. 90/013,857), dated Jan. 5, 2018, 5 pages.

Advisory Action in Request for Ex Parte Reexamination of U.S. Pat. No. 8,772,964 (U.S. Appl. No. 90/013,857), dated Nov. 24, 2017, 5 pages.

Aitman et al. "Progress and prospects in rate genetics: a community view," Nature Genetics, May 2008, pp. 516-522, vol. 40, No. 5.

Alberts, B., et al., eds., "Studying Gene Expression and Function", Molecular Biology of the Cell, 4th ed., New York: Garland Science, 2002.

Amos-Landgraf, et al. A target-selected Apc-mutant rat kindred enhances the modeling of familial human colon cancer, Proc Natl Acad Sci USA 2007, 104:4036-4041.

Anonymous, Gene Cyp7b1Tn(sb-T2/Bart3)2.306Mcwi, Tar Genome Database, http://rgd.mcw.edu/tools/genes/genesview.cgi?id=2303974 (Mar. 3, 2009), [retrieved on Nov. 5, 2011], 1 page.

Anonymous, "Strain F344-Cyp7b1Tn(sb-T2/Bart3)2.306Mcwi," Rat Genome Database, 2 pages. http://rgd.mcw.edu/tools/strains/strainsview.cgi?id=2303976 (Mar. 3, 2009), [retrieved on Nov. 5, 2010].

Asamoto, M. et al., "Connexin 32 Dominant—Negative Mutant Transgenic Rats are Resistant to Hepatic Damage by Chemicals," Hepatology, Jul. 1, 2004, pp. 205-210, vol. 40(1).

Ashburner, M., et al., "Gene Ontology: tool for the unification of biology. The Gene Ontology Consortium." 'Nature Genetics, May 2000, pp. 25-29, vol. 25.

Ayers et al. "Volume of preclinical xenograft tumors is more accurately assessed by ultrasound imaging than manual caliper measurements," J Ultrasound Med 29:891-901 (2010).

Baghdasaryan, A., et al. "Role of hepatic phospholipids in development of liver injury in Mdr2 (Abcb4) knockout mice," Liver International, Aug. 2008, vol. 28, Issue 7, pp. 948-958.

Bagshawe, K. D. "The First Bagshawe Lecture Towards generating cytotoxic agents at cancer sites," Br. J. Cancer, 1989, pp. 275-281, vol. 60, The Macmillan Press Ltd.

Bagshawe, K.D., "A cytotoxic agent can be generated selectively at cancer sites," Br. J. Cancer, vol. 58 (1988) pp. 700-703.

Baker, M., "Rat embryonic stem cells created," Nature, Dec. 24, 2008, downloaded from http://www.nature.com/news/2008/081224/full/news.2008.1336.html 3 pgs.

Barnes, P.J., "Cytokine modulators as novel therapies for airway disease," Eur Respir J, 2001, 18(Suppl. 34):67s-77s, 11 pgs.

Barthold, S.W., "Generically altered mice: phenotypes, no phenotypes, and Faux phenotypes", Genetica, 2004, vol. 122, pp. 75-88, 14 pgs.

Battelli et al., "T lymphocyte killing by a xanthine-oxidase-containing immunotoxin," Cancer Immunol. Immunother., 1992, 35:421-425.

Belay et al., "Transposon-mediated gene transfer into adult and induced pluripotent stem cells." Curr Gene Ther (2011); 11(5): 406-413.

Ben-Baruch et al. "Interleukin-8 Receptor 13 The Role of the Carboxyl Terminus in Signal Transduction." J Biol Chem 270(16):9121-9128, 1995.

(56) References Cited

OTHER PUBLICATIONS

Berghammer, A.J. et al., "A Universal Marker for Genetically Modified Insects," Nature, vol. 402 (1999) pp. 370-371.
Bessereau, J.L., et al. "Mobilization of a *Drosophila transposon* in the Caenorhabditis elegans germ line," Nature, Sep. 6, 2001, pp. 70-74, vol. 413, Macmillan Magazines Ltd.
Bhasin, A. et al., "Characterization of a Tn5 pre-cleavage synaptic complex", J. Mol. Biol., vol. 302 (2000) pp. 49-63.
Bi, L.L., et al., "Dominant inhibition of Fas ligand-mediated apoptosis due to a heterozygous mutation associated with autoimmune lymphoproliferative syndrome (ALPS) Type 1b," BMC Medical Genetics, 2007, 8:41, 14 pgs.
Biebermann, H., et al., "Autosomal-Dominant Mode of Inheritance of a Melanocortin-4 Receptor Mutation in a Patient with Severe Early-Onset Obesity is Due to a Dominant-Negative Effect Caused by Receptor Dimerization", Diabetes, Dec. 2003, vol. 52, pp. 2984-2988, 5 pgs.
Blackburn et al. "Adenosine Deaminase-deficient Mice Generated Using a Two-stage Genetic Engineering Strategy Exhibit a Combined Immunodeficiency," The Journal of Biological Chemistry, Feb. 27, 1998, pp. 5093-5100, vol. 273, No. 9, The American Society for Biochemistry and Molecular Biology, Inc.
Blackburn et al. "Adenosine mediates IL-13-induced inflammation and remodeling in the lung and interacts in an IL-13-adenosine amplification pathway," The Journal of Clinical Investigation, Aug. 2003, pp. 332-344, vol. 112, No. 3.
Bluestein, A., "Sage's Latest Knockout: $95,000 Lab Rats. St. Louis's Sage Labs has a Radical New Way to build a Better Rat for Scientific Study", Fast Company, Jun. 2011, 6 pgs.
Borish, MD, L.C., et al., "2. Cytokines and chemokines," J Allergy Clin Immunol, 2003, 111(2):S460-S475, 16 pgs.
Boxtel, et al., Homozygous and heterozygous P53 knockout rats develop metastasizing sarcomas with high frequency, Hubrecht Institute for Developmental Biology and Stem Cell Research, Cancer Genomics Centers, KNAW and University Medical Center Utrecht, The Netherlands; Department of Pathobiology, Faculty of Veterinary Medicine, Utrecht University, The Netherlands; Department of Medical Genetics, University Medical Center Utrecht, The Netherlands no date].
Breedveld, P. et al., "The Effect of Bcrpl (Abcg2) on the In vivo Pharmacokinetics and Brain Penetration of Imatinib Mesylate (Gleevec): Implications for the Use of Breast Cancer Resistance Protein and P-Glycoprotein Inhibitors to enable the Brain Penetration of Imatinib in Patients," Cancer Research, 2005, pp. 2577-2582, vol. 65(7).
Brigham et al., "Expression of a Prokaryotic Gene in Cultured Lung Endothelial Cells after Lipofection with a Plasmid Vector," Am J Respir Cell Mol Biol., 1989, 1:95-100.
Brinster et al. "Factors affecting the efficiency of introducing foreign DNA into mice by microinjecting eggs," Proc. Natl. Acad. Sci. USA, Jul. 1985, pp. 4438-4442, vol. 82.
Brinster et al., "No simple solution for making transgenic mice." Cell (1989); 59(2): 239-241.
Brown, V.I. and Greene, M.I. "Molecular and Cellular Mechanisms of Receptor-Mediated Endocytosis," DNA and Cell Biology, 1991, pp. 399-409, vol. 10, No. 6.
Bucheton, A. et al. "The Molecular Basis of I-R Hybrid Dysgenesis in *Drosophila melanogaster*: Identification, Cloning, and Properties of the I Factor," Cell, 1984, pp. 153-163, vol. 38, Issue 1.
Buehr et al. "Capture of Authentic Embryonic Stem Cells from Rat Blastocysts," Cell, Dec. 26, 2008, pp. 1287-1298, vol. 135, No. 7, Elsevier Inc.
Burrus, V et al. "The ICESt1 element of *Streptococcus thermophilus* belongs to a large family of integrative and conjugative elements that exchange modules and change their specificity of integration," Plasmid, Sep. 2002, pp. 77-97, vol. 48, Issue 2.
Bykov, V.J.N., et al., "Restoration of the tumor suppressor function to mutant p53 by a low-molecular-weight compound," Nature Medicine, Mar. 2002, 8(3): 282-288, 7 pgs.
Calafell, F., et al., "Basic molecular genetics for epidemiologists," J Epidemiol Community Health, 2003, 57:398-400, 3 pgs.

Cantz, T., et al., "Stem Cells in liver regeneration and therapy," Cell Tissue Res, 2008, 331:271-282, 12 pgs.
Capecchi, M.R., "Altering the Genome by Homologous Recombination," Science, vol. 244(4910) (1989) pp. 1288-1292.
Caterina, Michael J., et al. "Impaired nociception and pain sensation in mice lacking the capsaicin receptor." Science (2000); 288.5464: 306-313.
Chang, et al. "Tumourigenesis associated with the p53 tumour suppressor gene", Br J Cancer 1993, 68:653-661.
Charreau, et al. "Transgenesis in rats: technical aspects and models", Transgenic Research, 1996, pp. 223-234, vol. 5.
Chen, Y.-L., et al., "Nocistatin and nociceptin exert opposite effects on the excitability of central amygdale nucleus-periaquedactal gray projection neurons," Molecular and Cellular Neuroscience, 2009, pp. 76-88, vol. 40.
Cheng, Q., et al. "Specificity determinants for bacteriophage Hong Kong 022 integrase: analysis of mutants with relaxed core-binding specificities," Molecular Microbiology, 2000, pp. 424-436, vol. 36, No. 2.
Claesson, M.H. et al. "Antibodies Directed Against Monomorphic and Evolutionary Conserved Self Epitopes may be Generated in 'Knock-Out' Mice. Development of Monoclonal Antibodies Directed Against Monomorphic MHC Class I determinants," Scandinavian Journal of Immunology, Aug. 1994, pp. 257-264, vol. 40, Issue 2.
Clark, J., et al., "A future for transgenic livestock," Nature Reviews, Oct. 2003, pp. 825-833, vol. 4.
Clarke, AR. Murine models of neoplasia: functional analysis of the tumour suppressor genes Rb-1 and p53, Cancer Metastasis Rev 1995, 14:125-148.
Collado, M., et al., "Cellular Senescence in Cancer and Aging," Cell, Jul. 27, 2007, 130:223-233, 11 pgs.
Collier et al. "Cancer gene discovery in solid tumours using transposon-based somatic mutagenesis in the mouse", Nature, 2005, vol. 436, pp. 272-276.
Cong, L. et al. "Multiplex genome engineering using CRISPR/Cas systems." Science. Feb. 15, 2013;339(6121):819-23. doi: 10.1126/science.1231143. HHS Public Access Author Manuscript, 9 pages.
Corpet, et al. How good are rodent models of carcinogenesis in predicting efficacy in humans? A systematic review and meta-analysis of colon chemoprevention in rats, mice and men, European Journal of Cancer, Sep. 2005, pp. 1911-1922, vol. 41, Issue 13.
Cotroneo, et al. Characterizing a rat Brca2 knockout model, Oncogene 2007, 26:1626-1635.
Coward et al., "In vivo gene transfer into testis and sperm: developments and future application." Arch Androl (2007); 53(4):187-197.
Cui, Z. et al. "Structure-Function Analysis of the Inverted Terminal Repeats of the Sleeping Beauty Transposon," J. Mol. Biol., 2002, pp. 1221-1235, vol. 318.
"Curriculum vitae of Bart M.G. Smits, Ph.D.", Exhibit 1010 to Request for Ex Parte Reexamination of U.S. Pat. No. 8,722,964 (U.S. Appl. No. 90/013,857), filed Nov. 3, 2016, 5 pages.
"Curriculum vitae of Bart M.G. Smits, Ph.D.", Exhibit 1011 to Request for Ex Parte Reexamination of U.S. Pat. No. 8,558,055 (U.S. Appl. No. 90/013,858), filed Nov. 3, 2016, 5 pages.
Dahlman, I., et al., "Quantitative trait loci disposing for both experimental arthritis and encephalomyelitis in the DA rat; impact on severity of myelin oligodendrocyte glycoprotein-induced experimental autoimmune encephalomyelitis and antibody isotype pattern," Eur. J. Immunol., 1998, 28:2188-2196, 9 pgs.
"Declaration of Bart M.G. Smits, PHD," Exhibit 1011 to Request for Ex Parte Reexamination of U.S. Pat. No. 8,772,964 (U.S. Appl. No. 90/013,857), filed Nov. 3, 2016, 57 pages.
"Declaration of Bart M.G. Smits, PHD," Exhibit 1012 to Request for Ex Parte Reexamination of U.S. Pat. No. 8,558,055 (U.S. Appl. No. 90/013,858), filed Nov. 3, 2016, 66 pages.
Declerck, P.J. et al. "Generation of Monoclonal Antibodies against Autologous Proteins in Gene-inactivated Mice," The Journal of Biological Chemistry, Apr. 14, 1995, pp. 8397-8400, vol. 270, No. 15, The American Society for Biochemistry and Molecular biology, Inc.

(56) References Cited

OTHER PUBLICATIONS

Ding, S., et al. "Efficient transposition of the piggyBac (PB) transposon in mammalian cells and mice", Cell, Aug. 12, 2005; 122(3):473-83.
Doherty et al., "Hyperactive piggyBac gene transfer in human cells and in vivo." Hum Gene Ther (2012); 23(3): 311-320.
Donehower, et al. "Mice deficient for p53 are developmentally normal but susceptible to spontaneous tumours", Nature, Mar. 19, 1992, pp. 215-221, vol. 356.
Dong et al. "B7-H1, a third member of the B7 family, co-stimulates T-cell proliferation and interleukin-10 secretion", Nature Medicine, Dec. 1999, p. 1365-1369, vol. 5, No. 12.
Elg, S. et al., "Cellular Subtype Distribution and Developmental Regulation of TRCP Channel Members in the Mouse Dorsal Root Ganglion," The Journal of Comparative Neurology, 2007, pp. 35-46, vol. 503, Wiley-Liss, Inc.
"Excerpts from File History of U.S. Pat. No. 8,558,055", Exhibit 1013 to Request for Ex Parte Reexamination of U.S. Pat. No. 8,558,055 (U.S. Appl. No. 90/013,858), filed Nov. 3, 2016, 35 pages.
"Excerpts from File History of U.S. Pat. No. 8,722,964", Exhibit 1002 to Request for Ex Parte Reexamination of U.S. Pat. No. 8,722,964 (U.S. Appl. No. 90/013,857), filed Nov. 3, 2016, 112 pages.
"Excerpts from File History of U.S. Pat. No. 8,722,964", Exhibit 1010 to Request for Ex Parte Reexamination of U.S. Pat. No. 8,558,055 (U.S. Appl. No. 90/013,858), filed Nov. 3, 2016, 12 pages.
Felgner, P.L. et al, "Lipofection: A Highly Efficient, Lipid-Mediated DNA-Transfection Procedure," Proc. Natl. Acad. Sci. USA, vol. 84(21) (1987) pp. 7413-7417.
Fields, M.L. et al, "The Influence of Effector T Cells and Fas Ligand on Lupus-Associated B Cells," The Journal of Immunology, Jul. 1, 2005, pp. 104-111, vol. 175(1).
Final Office Action issued by The United States Patent and Trademark Office for U.S. Appl. No. 15/810,272, dated Feb. 3, 2021, 9 pages.
Franz, G. and Savakis, C. "Minos, a new transposable element from *Drosophila hydei*, is a member of the Tc1-like family of transposon," Nucleic Acids Research, Sep. 23, 1991, p. 6646, vol. 19, No. 23.
Freichel, M. et al, "Lack of an endothelial store-operated Ca2+ current impairs agonist-dependent vasorelaxation in TRP4-/- mice," Nature Cell Biology, Feb. 2001, pp. 121-127, vol. 3.
French, L.E., "Protein-based therapeutic approaches targeting death receptors," Cell Death and Differentiation, 2003, 10:117-123, 7 pgs.
Frischmeyer, P.A., et al., "Nonsense-mediated mRNA decay in health and disease," Human Molecular Genetics, 1999, 8(10 Review): 1893-1900, 8 pgs.
Gaj, et al., "ZFN, TALEN, and CRISPR/Cas-based methods for genome engineering." Trends in Biotechnology (2013); 31(7): 397-405.
Garza, J.C., et al., "Adeno-associated virus-mediated knockdown of melanocortin-4 receptor in the paraventricular nucleus of the hypothalamus promotes high-fat diet-induced hyperphagia and obesity", Journal of Endocrinology, 2008, vol. 197, pp. 471-482, 12 pgs.
Gene Targeting, A Practical Approach, IRL Press at Oxford University Press (1993), 2 pages.
"Gene Targeting", from the University of California at San Diego, Moores Cancer Center, accessed Jul. 23, 2015, at http://cancer.uscd.edu/research-training/shared-resources/transgenic-core/services/Pages/gene-targeting.aspx, 5 pgs.
Geurts, A.M., et al., "Conditional gene expression in the mouse using a Sleeping Beauty gene-trap transposon," BioMed Central Biotechnology, 2006, pp. 1-15, vol. 6:30.
Geurts, A.M., et al., "Gene Mutations and Genomic Rearrangements in the Mouse as a Result of Transposon Mobilization from Chromosomal Concatemers," PLOS Genetics, Sep. 2006, 2(9-e516):1413-1423, 17 pgs.

Geurts, A.M., et al., "Generation of gene-specific mutated rats using zinc-finger nucleases", Rat Genomics: Methods of Molecular Biology, 2010, vol. 597, pp. 211-225.
Geurts et al., "Knockout Rats via Embryo Microinjection of Zinc-Finger Nucleases," Science, vol. 325, No. 5939, Jul. 24, 2009, p. 433.
Ghebranious, N. et al, "The Mouse Equivalent of the Human p53ser249 Mutation p53ser246 Enhances Aflatoxin Hepatocarcinogenesis in Hepatitis B Surface Antigen Transgenic and p53 Heterozygous Null Mice," Hepatology, Apr. 1998, pp. 967-973, vol. 27, Issue 4.
Goldblatt, F., et al., "New therapies for systemic lupus erythematosus," Clinical and Experimental Immunology, 2005, 140:205-212, 8 pgs.
Gonzalez, F.J., "Role of cytochromes P450 in chemical toxicity and oxidative stress: Studies with CYP2E1," Mutation Research, Jan. 6, 2005, pp. 101-110, vol. 569 (1-2).
Hakamata, Y., et al., "Inducible and Conditional Promoter Systems to Generate Transgenic Animals", Chapter 5, Rat Genomics: Methods and Protocols, Methods in Molecular Biology (2010), vol. 597, pp. 71-79, 9 pgs.
Halestrap, A.P. et al, "The SLC16 gene family from monocarboxylate transporters (MCTs) to aromatic amino acid transporters and beyond," European Journal of Physiol., 2004, pp. 619-628, vol. 447.
Hammer, R.E. et al., "Spontaneous Inflammatory Disease in Transgenic Rats Expressing HLA-B27 and Human 2m: An Animal Model of HLA-B27-Associated Human Disorders," Cell, vol. 63 (1990) pp. 1099-1112.
Hannan, N.J., et al., "The Chemokines, CX3CL1, CCL14, and CCL4, Promote Human Trophoblast Migration at the Feto-Maternal Interface," Biology of Reproduction, 2006, 74:869-904, 9 pgs.
Harvey, et al. Spontaneous and carcinogen-induced tumorigenesis in p53-deficient mice, Nat Genet 1993, 5:225-229.
Hickman, A. B., et al. "Molecular Organization in Site-Specific Recombination: The Catalytic Domain of Bacteriophage HP1 Integrase at 2.7 A Resolution," Cell, Apr. 18, 1997, pp. 227-237, vol. 89, Issue 2, Cell Press.
Hogan, B., "Manipulating the Mouse Embryo", Cold Spring Harbor Laboratory Press, Cold Spring Harbor, N.Y., (1986).
Hollstein, et al. "p53 mutations in human cancers", Science 1991, 253:49-53.
Homberg, J.R. et al., "Complete Knockout of the Nociceptin/Orphanin FQ Receptor in the Rat Does Not Induce Compensatory Changes in , and Opioid Receptors," Neuroscience, 2009, pp. 308-315, vol. 163.
Houdebine, L.M. et al., "Transgenesis in fish," Experientia, vol. 47 (1991) pp. 891-897.
Hu, H.-Z., et al., "2-Aminoethoxydiphenyl Borate Is a common Activator of TRPV1, TRPV2, and TRPV3*," The Journal of Biological Chemistry, Aug. 20, 2004, pp. 35741-35748, vol. 279, No. 34, The American Society for Biochemistry and Molecular Biology, Inc.
Huang, et al. "Beyond knockout rats: new insights into finer genome manipulation in rats", Cell Cycle 2011, 10:1059-1066.
Hughes et al. "Monoclonal Antibody Targeting of Liposomes to Mouse Lung in Vivo," Cancer Research, Nov. 15, 1989, pp. 6214-6220, vol. 49, American Association for Cancer Research.
Huszar, D., et al., "Targeting Disruption of the Melanocortin-4 Receptor Results in Obesity in Mice", Cell, Jan. 10, 1997, Vo. 88, pp. 131-141, 11 pgs.
Hwang et al., "Efficient In Vivo Genome Editing Using RNA-Guided Nuclease," Nat Biotechnol 31(3):227-229 (2013).
Iannaccone, P.M., et al., "Rats!", Disease Models & Mechanisms, May-Jun. 2009, vol. 2, issue 5-6, pp. 206-210, 5 pgs.
International Preliminary Report on Patentability dated Feb. 21, 2012 for Application No. PCT/US2010/046144, 10 pages.
International Preliminary Report on Patentability dated Feb. 7, 2012 for Application No. PCT/US2010/044545, 9 pages.
International Preliminary Report on Patentability dated Jan. 24, 2012 for Application No. PCT/US2010/043043, 15 pages.
International Preliminary Report on Patentability dated Jan. 31, 2012 for Application No. PCT/US2010/043817, 10 pages.

(56) References Cited

OTHER PUBLICATIONS

International Preliminary Report on Patentability dated Jan. 4, 2012 for Application No. PCT/US2010/040768, 8 pages.
International Preliminary Report on Patentability dated Oct. 25, 2011 for Application No. PCT/US2010/032222, 17 pages.
International Preliminary Report on Patentability dated Sep. 24, 2013 for Application No. PCT/US2012/029736, 6 pages.
International Preliminary Report on Patentability issued by the International Searching Authority for Application No. PCT/US2018/025368, 10 pages.
International Search Report and Written Opinion issued by the International Searching Authority for Application No. PCT/US2018/025368, dated Jun. 14, 2018, 12 pages.
International Search Report dated Feb. 21, 2011 for Application No. PCT/US2010/043043, 11 pages.
International Search Report dated Nov. 11, 2010 for Application No. PCT/US2010/040768, 6 pages.
International Search Report dated Aug. 29, 2012 for Application No. PCT/US2012/029736, 6 pages.
International Search Report dated Dec. 7, 2010 for Application No. PCT/US2010/032222, 14 pages.
International Search Report dated Feb. 3, 2011 for Application No. PCT/US2010/044545, 8 pages.
International Search Report dated Mar. 10, 2011 for Application No. PCT/US2010/043817, 9 pages.
International Search Report dated Mar. 8, 2011 for Application No. PCT/US2010/046144, 6 pages.
Ivics, Z. et al., "Identification of functional domains and evolution of Tc1-like transposable elements," Proc. Natl. Acad. Sci. USA, vol. 93(10) (1996) pp. 5008-5013.
Izsvak, Z, et al. "Characterization of a Tc1-like transposable element in zebrafish (*Danio rerio*)," Molecular and General Genetics MGG, 1995, pp. 312-322, vol. 247, No. 3, Springer-Verlag.
Izsvak, Z, et al. "Sleeping Beauty, a Wide Host-range Transposon Vector for Genetic Transformation in Vertebrates," Journal of Molecular Biology, 2000, pp. 93-102, vol. 302, Issue 1, Academic Press.
Jacks, et al., "Tumor spectrum analysis in p53-mutant mice", Current Biology, 1994, pp. 1-7, vol. 4, No. 1.
Jacob, H.J., et al., "Gene Targeting in the Rat: Advances and Opportunities", Trends Genet., Dec. 2010, pp. 510-518, vol. 26(12).
Jacob, H.J., et al., "Rat genetics: attaching physiology and pharmacology to the genome", Nature Reviews | Genetics, Jan. 2002, pp. 33-42, vol. 3.
Jacob, H.J. "Functional genomics and rat models", Genome Res 1999, 9:1013-1016.
Jakobovits, A., "Tools of the Trade YAC Vectors: Humanizing the mouse genome." Current Biology, 1994, pp. 761-763, vol. 4, No. 8.
Jiang et al., "CRISPR-Assisted Editing of Bacterial Genomes," Nat Biotechnol 31(3):233-239 (2013).
Jinek et al., "A Programmable Dual-RNA-Guided DNA Endonuclease in Adaptive Bacterial Immunity," Science 337(6096):816-821 (2012).
Joyner, A.L., et al., "Production of a mutation in mouse En-2 gene by homologous recombination in embryonic stem cells," Nature, vol. 338 (1989) pp. 153-156.
Justice, M. J., et al., "Mouse ENU Mutagenesis," Human Molecular Genetics, 1999, pp. 1955-1963, vol. 8, No. 10.
Kage, K. et al., "Dominant-negative inhibition of breast cancer resistance protein as drug efflux pump through the inhibition of S-S dependent homodimerization," International Journal of Cancer, Feb. 10, 2002, pp. 626-630, vol. 97(5).
Kano, H., et al., "L1 retrotransposition occurs mainly in embryogenesis and creates somatic mosaicism," Genes & Development, 2009, 23;1303-1312, 10 pgs.
Karray et al. Complete Loss of Fas Ligand Gene Causes Massive Lymphoproliferation and Early Death, Indicating a Residual Activity of gld Allele. Journal of Immunology, 2004, vol. 172,pp. 2118-2125.
Katter et al., "Transposon-mediated transgenesis, transgenic rescue, and tissue-specific gene expression in rodents and rabbits." FASEB Journal (2013); 27(3): 930-941.

Ke, Z, et al. "Quetzal: a transposon of the Tc1 family in the mosquito *Anopheles albimanus*," Genetica, 1996, pp. 141-147, vol. 98, No. 2.
Keller, G., "Embryonic stem cell differentiation: emergence of a new era in biology and medicine," Genes & Development, 2005, 19:1129-1155, 28 pgs.
Keng et at, "Region-specific saturation germline mutagenesis in mice using the Sleeping Beauty transposon system," Nature Methods, Oct. 2005, pp. 763-769, vol. 2, No. 10.
Kinsey, J.A., "Tad, a LINE-Like Transposable Element of Neurospora, Can transpose Between Nuclei in Heterokaryons," Genetics, Oct. 1990, pp. 317-326, vol. 126, Genetics Society of America.
Kitada et al. "Generating mutant rats using the Sleeping Beauty transposon system," Methods: A Companion to Methods in Enzymology, 2009, pp. 236-242, vol. 49, Academic Press Inc., New York, NY, US.
Kitada et al. "Transposon-tagged mutagenesis in the rat." Nature Methods, Feb. 2007, pp. 131-133, vol. 4, No. 2.
Kley, N.J. et al., "A Universal Marker for Transgenic Insects," Nature, Nov. 25, 1999, pp. 370-371, vol. 402, Macmillan Magazines Ltd.
Kloeckener-Gruissem, B., et al. "Mutation of Solute Carrier SLC16A12 Associates with Syndrome Combining Juvenile Cataract with Microcornea and Renal Glucosuria," The American Journal of Human Genetics, Mar. 2008, pp. 772-779, vol. 82.
Kobayashi, T., et al., "A germline insertion in the tuberous sclerosis (Tsc2) gene gives rise to the Eker rat model of dominantly inherited cancer," Nature Genetics, vol. 9, Jan. 1995, pp. 70-74.
Kogan, G L, et al., "The GATE retrotransposon in *Drosophila melanogaster*: mobility in heterochromatin and aspects of its expression in germ line tissues," Molecular Genetics and Genomics, Mar. 14, 2003, pp. 234-242, vol. 269, No. 2.
Krug, et al. Tumor suppressor genes in normal and malignant hematopoiesis, Oncogene 2002, 21:3475-3495.
Kuduvalli, P.N., et al. "Target DNA structure plays a critical role in Tn7 transposition," The EMBO Journal, 2001, pp. 924-932, vol. 20, No. 4, European Molecular Biology Organization.
Kuff et al. Intracisternal A—particle genes as movable elements in the mouse genome. PNAS, 1983, vol. 80, pp. 1992-1996.
Kullberg et al. "Helicobacter hepaticus Triggers Colitis in Specific-Pathogen-Free Interleukin-10 (IL-10)-Deficient Mice through an IL-12 and Gamma Interferon-Dependent Mechanism", Infection Immunity, 1998, vol. 66, pp. 5157-5166.
Kullberg, et al. "Helicobacter hepaticus-Induced Colitis in Interleukin-10-Deficient Mice: Cytokine Requirements for the Induction and Maintenance of Intestinal Inflammation", Infection and Immunity, Jul. 2001, pp. 4232-4241, vol. 69, No. 7.
Lacroix-Fralish, M.L., et al., "The Pain Genes Database: An interactive web browser of pain-related transgenic knockout studies," Pain, 2007, 131:3.e1-3.e4.
Lakso, M. et al., "Targeted Oncogene Activation by Site-Specific Recombination in Transgenic Mice," PNAS, vol. 89(14) (1992) pp. 6232-6236.
Lam, P. et al., "Bile Acid Transport in Sister of P-Glycoprotein (ABCB11) Knockout Mice," Biochemistry, 2005, pp. 12598-12605, vol. 44(37).
Lam, W L, et al. "Discovery of Amphibian Tc1-like Transposon Families," Journal of Molecular Biology, 1996, pp. 359-366, vol. 257, Issue 2, Academic Press Limited.
Lampe, D.J., et al. "Factors affecting transposition of the Himar1 mariner transposon in vitro," Genetics, May 1998, pp. 179-187, vol. 149(11), Genetics Society of America.
Lee, S.S.T. et al., "Role of CYP2E1 in the Hepatotoxicity of Acetaminophen," J. Biol. Chem., 1996, pp. 1-16, vol. 271(20).
Lewerenz, J., et al., "Basal Levels of eIF2 Phosphorylation Determine Cellular Antioxidant Status by Regulating ATF4 and xCT Expression," The Journal of Biological Chemistry, Jan. 9, 2009, pp. 1106-1115, vol. 284 No. 2.
Li, P., et al., "Germline Competent Embryonic Stem Cells Derived from Rat Blastocysts," Cell, Dec. 2008, pp. 1299-1310, vol. 135, Issue 7.

(56) References Cited

OTHER PUBLICATIONS

Li, Y. and Austin, S. "The P1 plasmid in action: time-lapse photomicroscopy reveals some unexpected aspects of plasmid partition," Plasmid, Jul. 22, 2002, pp. 174-178, vol. 48, issue 3, 2002 Elsevier Science (USA).

Liang, H.C.L. et al., "Cypla2(−/−) null mutant mice develop normally but show deficient drug metabolism," PNAS, vol. 93 (Feb. 1996) pp. 1671-1676.

Li-Hawkins, J. et al., "Disruption of the oxysterol 7alpha-hydroxylase gene in mice," Journal of Biological Chemistry, Jun. 2, 2000, pp. 16536-16542, vol. 275(22).

Lin, S., "Transgenic Zebrafish," Developmental Biology Protocols: vol. II—Methods in Molecular Biology, 2000, pp. 375-383, vol. 136, IV.

Lindblad-Toh, Kerstin, "Three's company: Publication of the rat genome sequence will not only advance physiological studies in this paragon of laboratory animals, but also greatly enhance the power of comparative research into mammalian genomes", Nature, Apr. 1, 2004, pp. 475-476, vol. 428.

Lindsay, J.O., et al., "The Prevention and Treatment of Murine Colitis Using Gene Therapy with Adenoviral Vectors Encoding IL-101," J Immunol, 2001, 166:7625-7633, 10 pgs.

Litzinger, D.C. and Huang, L. "Biodistribution and immunotargetability of ganglioside-stabilized dioleoylphosphatidylethanolamine liposomes," Biochimica et Biophysica Acta (BBA)Biomembranes, Feb. 17, 1992, pp. 179-187, vol. 1104, Issue 1.

Liu, R. et al., "Cystine-Glutamate Transporter SLC7A11 Mediates Resistance to Geldanamycin but Not to 17-(Allylamino)-17-demethoxygeldanamycin," Molecular Pharmacology, 2007, pp. 1637-1646, vol. 72, No. 6.

Lorentzen, J.C., et al., "Identification of rat susceptibility loci for adjuvant-oil-induced arthritis," Proc. Natl. Acad. Sci. USA, May 1998, 95:6383-6387, 5 pgs.

Lorico, A. et al., "Disruption of the Murine MRP (Multidrug Resistance Protein) Gene Leads to Increased Sensitivity to Etoposide (VP-16) and Increased Levels of Glutathione," Cancer Research, 1997, pp. 5238-5242, vol. 57.

Lu et al, "Generation of rat mutants using a coat color-tagged Sleeping Beauty transposon system", Mammalian Genome, 2007, vol. 18, Issue 5 , pp. 338-346.

Luan, D.D. et al., "Reverse Transcription of R2Bm RNA Is Primed by a Nick at the Chromosomal Target Site: A Mechanism for Non-LTR Retrotransposition," Cell, vol. 72 (1993) pp. 595-605.

Luan, D.D. et al, "RNA Template Requirements for Target DNA-Primed Reverse Transcription by the R2 Retrotransposable Element," Mol. Cell Biol., vol. 15(7) (1995) pp. 3882-3891.

Maeder and Gersbach, "Genome-editing Technologies for Gene and Cell Therapy." Molecular Therapy (2016); 24(3): 430-446.

Makino, H., et al., "Rat p53 gene mutations in primary Zymbal glad tumors induced by 2-amino-3-methylimidazo[4,5-]quinoline, a food mutagen", Proc. Natl. Acad. Sci., USA, Jun. 1992, vol. 89, pp. 4850-4854, 5 pgs.

Mali, L. et al. (Feb. 15, 2013) "RNA-Guided Human Genome Engineering via Cas9" Science, 339(6121):823-826.

Malkin, et al. Germ line p53 mutations in a familial syndrome of breast cancer, sarcomas, and other neoplasms, Science 1990, 250:1233-1238.

Marh et al., "Hyperactive self-inactivating piggyBac for transposase-enhanced pronuclear microinjection transgenesis." PNAS (2012); 109(47): 19184-19189.

Marra, D. and Scott, J. R. "Regulation of excision of the conjugative transposon Tn916," Molecular Microbiology, 1999, pp. 609-621, vol. 31(2).

Martin, C. et al., "CYP7B Generates a Selective Estrogen Receptor Agonist in Human Prostate," The Journal of Clinical Endocrinology & Metabolism, 2004, pp. 2928-2935, vol. 89(6).

Mashimo et al. "Generation of Knockout Rats with X-Linked Severe Combined Immunodeficiency (X-SCID) Using Zinc-Finger Nucleases," Plos One, Jan. 2010, pp. 1-7, vol. 5, issue 1, E8870.

Masui et al. "Establishment of a Set of Combined Immunodeficient DA/S1c-Foxn1rnu Lystbg Congenic Rat Strains," Experimental Animals (Tokyo), 2004, pp. 399-407, vol. 53, No. 5.

Mates et al., "Molecular evolution of a novel hyperactive Sleeping Beauty transposase enables robust stable gene transfer in vertebrates," Nature Genetics, Technical Report, Jun. 2009, 41(6):753-761, 9 pgs.

Mates et al., "Technology transfer from worms and flies to vertebrates: transposition-based genome manipulations and their future perspectives," Genome Biology, 2007, 8(Suppl 1):S1-S1.19, 19 pgs.

McDorman, K.S. et al. "Use of the Spontaneous Tsc2 Knockout (Eker) Rat Model of hereditary Renal Cell Carcinoma for the Study of Renal Carcinogens," Toxicologic Pathology, 2002, pp. 675-680, vol. 30, No. 6.

Merriman, P J, et al. "S Elements: A Family of Tc1-Like Transposons in the Genome of *Drosophila melanogaster*," Genetics, Dec. 1995, pp. 1425-1438, vol. 141, Genetics Society of America.

Miao and Zhang, "Production of transgenic mice carrying the Thanatin gene by intratesticular injection." Biochem Biophys, Res Commun (2011); 415(3): 429-433.

Mizuno, N. et al., "Impact of drug transporter studies on drug discovery and development," Pharmacological Reviews, Sep. 2003, pp. 425-461, vol. 55(3).

Mizuno, N., et al., "Impaired Renal Excretion Of 6-Hydroxy-5,7-Dimethyl-2-Methylamino-4-(3-Pyridylmethyl) Benzothiazole (E3040) Sulfate In Breast Cancer Resistance Protein (Bcrp1/Abcg2) Knockout Mice." Drug Metabolism and Disposition ( 2004); 32(9): 898-901.

Mulligan, Lois M., et al. "Mechanisms of p53 loss in human sarcomas." Proceedings of the National Academy of Sciences (1990); 87.15: 5863-5867.

Nagata, S., "Human autoimmune lymphoproliferative syndrome, a defect in the apoptosis-inducing Fas receptor: A lesson from the mouse model," J. Hum. Genet., vol. 43 (1998) pp. 2-8.

Nakagama, et al. Modeling human colon cancer in rodents using a food-borne carcinogen, PhIP, Cancer Science, Oct. 2005, pp. 627-639, vol. 96, No. 10.

Nandi, et al. Hormones and mammary carcinogenesis in mice, rats, and humans: A unifying hypothesis, PNAS, Apr. 1995, pp. 3650-3657, vol. 92.

Nishimura, et al., "c drug-metabolizing enzymes and transporters in chimeric mouse with humanized liver." Xenobiotica (2005); 35(9): 877-890.

Nishiyama; Y., et al., "Low Incidence of Point Mutations in H-, K- and N-ras Oncogenes and p53 Tumor Suppressor Gene in Renal Cell Carcinoma and Peritoneal Mesothelioma of Wistar Rats Induced by Ferric Nitrilotriacetate", Jpn., J. Cance Res., Dec. 1995, vol. 86, pp. 1150-1158, 9 pgs.

Niu and Liang, "Progress in gene transfer by germ cells in mammals." J Genet Genomics (2008); 35(12): 701-714.

Nobuyuki, et al. "A new colon and mammary carcinogen in cooked food, 2-amino-1-methyl-6-phenylimidazo[4,5-b]pyridine (PhIP)", Carcinogenesis, 1991, pp. 1503-1506, vol. 12, No. 8.

Nordlinger, et al. "Experimental model of colon cancer: Recurrences after surgery alone or associated with intraperitoneal 5-fluorouracil chemotherapy", Diseases of the Colon & Rectum, Aug. 1991, pp. 658-663, vol. 34.

Notice of Allowance issued by The United States Patent and Trademark Office for U.S. Appl. No. 15/810,272, dated Mar. 2, 2021, 9 pages.

Notice of Intent to Issue Ex Parte Reexamination Certificate in Ex Parte Reexamination of U.S. Pat. No. 8,772,964 (U.S. Appl. No. 90/013,857), dated Jan. 26, 2018, 5 pages.

Noto et al., Sprague-Dawley Rag2/Null Rats Created from Engineered Spermatogonial Stem Cells Are Immunodeficient and Permissive to Human Xenografts, Mol Cancer Ther: 17(11)2481-2488 (2018).

Noto et al., "The SRG Rat, A Sprague-Dawley Rag2/II2rg Double-Knockout Validated for Human Tumor Oncology Studies," PLOS One, pp. 1-16 (2020).

(56) References Cited

OTHER PUBLICATIONS

Nunes-Duby, SE, et al. "Similarities and differences among 105 members of the Int family of site-specific recombinases," Nucleic Acids Research, 1998, pp. 391-406, vol. 26, No. 2, Oxford University Press.
"Office Action" in Request for Ex Parte Reexamination of U.S. Pat. No. 8,558,055 (U.S. Appl. No. 90/013,858), dated Apr. 7, 2017, 15 pages.
"Office Action" in Request for Ex Parte Reexamination of U.S. Pat. No. 8,558,055 (U.S. Appl. No. 90/013,858), dated Aug. 8, 2017, 15 pages.
"Office Action" in Request for Ex Parte Reexamination of U.S. Pat. No. 8,772,964 (U.S. Appl. No. 90/013,857), dated Aug. 11, 2017, 16 pages.
"Office Action" in Request for Ex Parte Reexamination of U.S. Pat. No. 8,772,964 (U.S. Appl. No. 90/013,857), dated Mar. 31, 2017, 17 pages.
Office Action in U.S. Appl. No. 14/776,656 dated Jul. 24, 2017, 20 pages.
Office Action in U.S. Appl. No. 14/979,754 dated Jun. 26, 2017, 15 pages.
Office Action in U.S. Appl. No. 14/979,760 dated Mar. 5, 2018, 13 pages.
Office Action in U.S. Appl. No. 14/979,760 dated May 18, 2017, 14 pages.
Office Action in U.S. Appl. No. 15/070,275 dated May 11, 2017, 26 pages.
O'Gorman, S. et al., "Recombinase-Mediated Gene Activation and Site-Specific Integration in Mammalian Cells," Science, vol. 251(1991) pp. 1351-1355.
Okimoto, K., et al., "A germ-line insertion in the Bin-Hogg-Dub (BHD) gene gives rise to the Nihon rat model of inherited renal cancer", Proc. Natl. Acad. Sci., Feb. 17, 2004, vol. 101, No. 7, pp. 2023-2027, 5 pgs.
Olivier, J.D.A., et al., "A Study in Male and Female 5-HT Transporter Knockout Rats: An Animal Model for Anxiety and Depression Disorders", Neuroscience, 152 (2008) 573-584.
Omoto, Y., et al., "Early onset of puberty and early ovarian failure in CYP7B1 knockout mice," PNAS, Feb. 22, 2005, pp. 2814-2819, vol. 102, No. 8.
"Order Granting Request for Ex Parte Reexamination," Request for Ex Parte Reexamination of U.S. Pat. No. 8,558,055 (U.S. Appl. No. 90/013,858), dated Jan. 19, 2017, 13 pages.
"Order Granting Request for Ex Parte Reexamination," Request for Ex Parte Reexamination of U.S. Pat. No. 8,772,964 (U.S. Appl. No. 90/013,857), dated Dec. 15, 2016, 13 pages.
Ostertag, E.M., et al., "Mutagenesis in rodents using the L1 retrotransposagen," Genome Biology, 2007, 8(Suppl. 1):S16-S16.9, 9 pgs.
O'Sullivan, G.J., et al., "Potential and limitations of genetic manipulation in animals," Drug Discovery Today: Technologies, 2006, vol. 3, No. 2, pp. 173-180.
Parrington et al., "Sperm and testis mediated DNA transfer as a means of gene therapy." Syst Biol Reprod Med (2011); 57(1-2): 35-42.
Phillips, M.S., et al, "Leptin receptor missense mutation in the fatty Zucker rat," Nature Genetics, May 1996, pp. 18-19, vol. 13.
Phys Gen Knockouts, Strain Report for F344-FasIgTn(sb-T2/Bart3)2.325Mcwi (May 11, 2009), 2 pages. http://rgd.mcw.edu/tools/strains/strainsview.cgi?Submit=View+Strain&id=2306875.
Pietersz, G.A. and Mckenzie, I.F.C. "Antibody Conjugates for the Treatment of Cancer," Immunology Reviews, Oct. 1992, pp. 57-80, vol. 129, Issue 1.
Preudhomme, et al. Very low incidence of p53 antibodies in adult non-Hodgkin's lymphoma and multiple myeloma, Br J Haematol 1998, 100:184-186.
Purdie, et al. Tumour incidence, spectrum and ploidy in mice with a large deletion in the p53 gene, Oncogene (1994); 9: 603-609.
Pursel, V.G. et al., "Genetic Engineering of Livestock," Science, vol. 244(4910) (1989) pp. 1281-1288.
"Request for Ex Parte Reexamination of U.S. Pat. No. 8,558,055 (U.S. Appl. No. 90/013,858) Under 35 U.S.C. 302-307 and 37 C.F.R. 1.510", including Exhibits, filed Nov. 3, 2016, part 1 of 2, 262 pages.
"Request for Ex Parte Reexamination of U.S. Pat. No. 8,558,055 (U.S. Appl. No. 90/013,858) Under 35 U.S.C. 302-307 and 37 C.F.R. 1.510", including Exhibits, filed Nov. 3, 2016, part 2 of 2, 200 pages.
"Request for Ex Parte Reexamination of U.S. Pat. No. 8,772,964 (U.S. Appl. No. 90/013,857) Under 35 U.S.C. 302-307 and 37 C.F.R. 1.510", including Exhibits, filed Nov. 3, 2016, part 1 of 2, 284 pages.
"Request for Ex Parte Reexamination of U.S. Pat. No. 8,772,964 (U.S. Appl. No. 90/013,857) Under 35 U.S.C. 302-307 and 37 C.F.R. 1.510", including Exhibits, filed Nov. 3, 2016, part 2 of 2, 200 pages.
Rezende, L. F., et al. "Essential Amino Acid Residues in the Single-stranded DNA-binding Protein of Bacteriophage T7. Identification of the Dimer Interface," The Journal of Biological Chemistry, Dec. 27, 2002, pp. 50643-50653, vol. 277, No. 52, The American Society for Biochemistry and molecular Biology, Inc.
RGD, "Gene: Cyp7b1Tn(sb-T2/Bart3)2.306Mcwi (cytochrome P450, family 7, subfamily b, polypeptide 1; transposon insertion 2.306, Medical College of Wisconsin) Rattus norvegicus" Bioinformatics Program, HMGC at the Medical College of Wisconsin, Mar. 3, 2009, 2 pages.
Rhinehart, E.K., et al., "Neuropeptidergic characterization of the leptin receptor mutated obese Koletsky rat," Regulatory Peptides, 2004, pp. 3-10, vol. 119.
Riley, et al. "Transcriptional control of human p53-regulated genes", Natl Rev Mol Cell Biol 2008, 9:402-412.
Robertson, E. J., Teratocarcinomas and Embryonic Stem Cells, A Practical Approach, ed., IRL Press (1987).
Roffler, S. et al., "Anti-neoplastic glucuronide prodrug treatment of human tumor cells targeted with a monoclonal antibody-enzyme conjugate," Biochem. Pharmacol., vol. 42(10) (1991) pp. 2062-2065.
Rohacs, T., et al.,. "Phospholipase C mediated modulation of TRPV1 Channels," Mol Neurobiol, 2008, pp. 153-163, vol. 37.
Rose, K. et al., "Neurosteroid Hydroxylase CYP7B Vivid Reporter Activity in Dentate Gyrus of Gene-Targeted Mice and Abolition of a Widespread Pathway of Steroid and Oxysterol Hydroxylation," J. Biol. Chemistry (2001); 276(26): 23937-23944.
Rostovskaya et al., "Transposon mediated BAC transgenesis via pronuclear injection of mouse zygotes." Genesis (2013); 51(2): 135-141.
Rubin, G. M. and Spradling A. C. "Vectors for P element-mediated gene transfer in *Drosophila*," Nucleic Acids Research, 1983, pp. 6341-6351, vol. 11, No. 18.
Rubin, G.M. and Spradling, A.C. "Genetic Transformation of *Drosophila* with Transposable Element Vectors," Science, Oct. 22, 1982, pp. 348-353, vol. 218.
Russo, et al. "Comparative study of human and rat mammary tumorigenesis", Lab Invest, Mar. 1990, vol. 62(3), pp. 244-278.
Ryan, M.J., et al., "Use of Transgenic and Knockout Strategies in Mice", Seminars in Nephrology, Mar. 2002, vol. 22, No. 2, pp. 154-160, 7 pgs.
Ryding et al. "Conditional transgenic technologies," Journal of Endocrinology, 2001, pp. 1-14, vol. 171.
Sangamo Press Release, "Researchers Create First Targeted Knockout Rats Using Finger Nuclease Technology", Jul. 23, 2009, 2 pgs.
Sato et al., "Spatiotemporal analysis of [Ca2+]i rises in mouse eggs after intracytoplasmic sperm injection (ICSI)." Cell Calcium (1999); 26(1-2): 49-58.
Sato, H., et al., "Redox Imbalance in Cystine/Glutamate Transporter-deficient Mice," The Journal of Biological Chemistry, Nov. 11, 2005, pp. 37423-37429, vol. 280, No. 45.
Schneider, E. et al., "Organic cation transporter 3 modulates murine basophil functions by controlling intracellular histamine levels," J. Exp. Med., Aug. 1, 2005, pp. 387-393, vol. 202, No. 3.
Schwarz, M., "Pathways and defects of bile acid synthesis: insights from in vitro and in vivo experimental models," Drug Discovery Today: Disease Models, Dec. 17, 2004, pp. 205-212, vol. 1(3).

(56) References Cited

OTHER PUBLICATIONS

Sen, B., et al. "The transcriptional profile of the kidney in Tsc2 heterozygous mutant Long Evans (Eker) rats compared to wild-type," Mutation Research/Fundamental and Molecular Mechanisms of Mutagenesis, May 2004, pp. 213-224, vol. 549, Issues1-2.
Senter, P.D. et al. "Generation of 5-Flourouracil from 5-Flourocytosine by Monoclonal Antibody-Cytosine Deaminase Conjugates," Bioconjugate Chemistry, 1991, vol. 2 (6), pp. 447-451.
Senter, P.D. et al. "Generation of Cytotoxic Agents by Targeted Enzymes," Bioconjugate Chemistry, 1993, vol. 4 (1), pp. 3-9.
Sesink, et al., "Breast Cancer Resistance Protein (Bcrp1/Abcg2) Limits Net Intestinal Uptake of Quercetin in Rats by Facilitating Apical Efflux of Glucuronides." Molecular Pharmacology (2005); 67(6): 1999-2006.
Setchell, K.D.R. et al., "Identification of a New Inborn Error in Bile Acid Synthesis: Mutation of the Oxysterol 7-Hydroxylase Gene Causes Severe Neonatal Liver Disease," J. Clin. Invest., Nov. 1998, pp. 1690-1703, vol. 102, No. 9.
Shoemaker, N. B. et al., "The Bacteroides mobilizable insertion element, NBU1, integrates into the 3' end of a Leu-tRNA gene and has an integrase that is a member of the lambda integrase family," J. Bacteriol., vol. 178(12) (1996) pp. 3594-3600.
Shultz et al. "Humanized mice in translational biomedical research." Nature Reviews Immunology (2007); 7.2: 118-130.
Silos et al., "Patient-Derived Tumor Xenografts: Transforming Clinical Samples into Mouse Models," American Association for Cancer Research, pp. 5315-5319 (2013).
Simons, J.P. et al., "Gene Transfer into Sheep." Nature Biotechnology, Feb. 1988, pp. 179-183, vol. 6.
Smits, B.M.G., et al., "Gene Targeting in the Rat? Cut it Out!", Molecular Interventions, Oct. 2009, vol. 9, Issue 5, pp. 226-229.
Smits, B.M.G. et al., "Rat genetics: the next episode," Trends in Genetics, Apr. 2006, pp. 232-240, vol. 22(4).
Smits, et al. "Generation of gene knockouts and mutant models in the laboratory rat by ENU-driven target-selected mutagenesis", Pharmacogenet Genomics 2006, 16:159-169.
Smits, et al. "Genetically Engineered Rat Models for Breast Cancer", Breast Disease, 2007, pp. 53-61, vol. 28.
Son, et al. "Profile of early occurring spontaneous tumors in Han Wistar rats", Toxicol Pathol 2010, 38:292-296.
Sparreboom, A. et al., "Limited oral bioavailability and active epithelial excretion of paclitaxel (Taxol) caused by P-glycoprotein in the intestine," PNAS, Mar. 1997, pp. 2031-2035, vol. 94.
Steinke and Borish et al., "3. Cytokines and Chemokines," J Allergy Clin Immunol, 2006, 117(2):S441-S445, 5 pgs.
Stemmer, K. et al. "Carcinogen-Specific Gene Expression Profiles in Short-term Treated Eker and Wild-type Rats Indicative of Pathways Involved in Renal Tumorigenesis," Cancer Cancer Research, 2007, pp. 4052-4068, vol. 67.
Sun, X. et al, "Conditional inactivation of Fgf4 reveals complexity of signaling during limb bud development," Nat. Genet., vol. 25 (2000) pp. 83-86.
Surani, M.A., "Reprogramming of genome function through epigenetic inheritance", Nature, Nov. 1, 2001, 414:122-128, 7 pgs.
Swanberg, M., et al., "MHC2TA is associated with differential MHC molecule expression and susceptibility to rheumatoid arthritis, multiple sclerosis and myocardial infarction," Nature Genetics, May 2005, 37(5):486-494, 11 pgs.
Szakacs, G. et al., "The role of ABC transporters in drug absorption, distribution, metabolism, excretion and toxicity (ADME-Tox)," Drug Discovery Today, May 1, 2008, pp. 279-393, vol. 13(9-10).
Tesson, L., et al., "Knockout rats generated by embryo microinjection of TALENs," Nature Biotechnology, vol. 29, No. 8, Aug. 2011, pp. 695-696.
Tischfield, J.A., "Somatic Genetics '97, Loss of Heterozygosity or: How I Learned to Stop Worrying and Love Mitotic Recombination," Am. J. Hum. Genet., 1997, 61:995-999.
Tong, C. et al, "Production of p53 gene knockout rats by homologous recombination in embryonic stem cells", Nature, Sep. 2010, pp. 211-213, vol. 467.
Toshiki, T. et al. "Germline transformation of the silkworm *Bombyx mori* L. using a piggyBac transposon-derived vector," Nature Biotechnology, Jan. 2000, pp. 81-84, vol. 18, Nature America Inc.
Tsubura, et al, Animal Models of N-Methyl-N-nitrosourea-induced Mammary Cancer and Retinal Degeneration with Special Emphasis on Therapeutic Trials, in vivo, Jan.-Feb. 2011, pp. 11-22, vol. 25, No. 1.
Tu, Z. and Shao, H. "Intra- and inter-specific diversity of Tc-3-like transposons in nematodes and insects and implications for their evolution and transposition," Gene, Jan. 9, 2002, pp. 133-142, vol. 282, Issues 1-2.
U.S. Appl. No. 61/172,016, filed Apr. 23, 2009, 119 pages.
U.S. Appl. No. 61/222,327, filed Jul. 1, 2009, 90 pages.
U.S. Appl. No. 61/228,369, filed Jul. 24, 2009, 97 pages.
U.S. Appl. No. 61/229,979, filed Jul. 30, 2009, 117 pages.
U.S. Appl. No. 61/231,549, filed Aug. 5, 2009, 98 pages.
U.S. Appl. No. 61/235,559, filed Aug. 20, 2009, 114 pages.
U.S. Appl. No. 61/466,603, filed Mar. 23, 2011, 99 pages.
U.S. Appl. No. 61/467,600, filed Mar. 25, 2011, 102 pages.
U.S. Appl. No. 90/013,858, Exhibit 1005 to Request for Ex Parte Reexamination of U.S. Pat. No. 8,558,055 (U.S. Appl. No. 90/013,858), filed Nov. 3, 2016, 58 pages.
U.S. Appl. No. 90/013,857, Exhibit 1005 to Request for Ex Parte Reexamination of U.S. Pat. No. 8,722,964 (U.S. Appl. No. 90/013,857), filed Nov. 3, 2016, 58 pages.
Van Boxtel, et al. "ENU mutagenesis to generate genetically modified rat models", Methods Mol Biol 2010, 597:151-167.
Van Boxtel et al. "Homozygous and heterozygous p53 knockout rats develop metastasizing sarcomas with high frequency." American J Pathol, 2011, vol. 179, pp. 1616-1622.
Van Boxtel, et al. "Improved generation of rat gene knockouts by target-selected mutagenesis in mismatch repair-deficient animals", BMC Genomics 2008, 9:460, 10 pages.
Van Boxtel, et al. "Lack of DNA mismatch repair protein MSH6 in the rat results in hereditary non-polyposis colorectal cancer-like tumorigenesis", Carcinogenesis 2008, 29:1290-1297.
Van Boxtel, et al. "Rat traps: filling the toolbox for manipulating the rat genome", Genome Biol 2010, 11 (9): 217, 9 pages.
Van Boxtel, R. et al., "Rat Reverse Genetics: Generation and Characterization of Chemically Induced Rat Mutants," Diss. Utrecht University 2010, pp. 1-82 (XP-002681613).
Van Boxtel, R., et al., "Systematic generation of in vivo G protein-coupled receptor mutants in the rat," The Pharmacogenomics Journal, 2011 pp. 326-336, vol. 11.
Van Herwaarden, A.E. et al., "Knockout of cytochrome P450 3A yields new mouse models for understanding xenobiotic metabolism," The Journal of Clinical Investigation, Nov. 2007, pp. 3583-3592, vol. 117(11).
Wakamiya et al., "Disruption of the adenosine deaminase gene causes hepatocellular impairment and perinatal lethality in mice," Proc. Natl. Acad. Sci. USA, Apr. 1995, pp. 3673-3677, vol. 92.
Wang, et al. "Difference in the Response of neu and ras Oncogene-induced Rat Mammary Carcinomas to Early and Late Ovariectomy", Cancer Research, Aug. 1, 1992, pp. 4102-4105, vol. 52.
Watanabe, H., et al., "The Pathological Role of Transient Receptor Potential Channels in Heart Disease," Circulation Journal, Mar. 2009, pp. 419-427, vol. 73.
Wilmut, I. et al, "Viable offspring derived from fetal and adult mammalian cells," Nature, vol. 385 (1997) pp. 810-813.
Wissenbach, U., et al., "TRP channels as potential drug targets," Science Direct, Biology of the Cell (2004); 96: 47-54.
Wolff, J. A., et al. "Direct gene transfer into mouse muscle in vivo," Science, Mar. 23, 1990, pp. 1465-1468, vol. 247, No. 4949.
Written Opinion dated Aug. 29, 2012 for Application No. PCT/US2012/029736, 5 pages.
Written Opinion dated Dec. 7, 2010 for Application No. PCT/US2010/032222, 16 pages.
Written Opinion dated Feb. 21, 2011 for Application No. PCT/US2010/043043, 14 pages.
Written Opinion dated Feb. 3, 2011 for Application No. PCT/US2010/044545, 8 pages.
Written Opinion dated Mar. 10, 2011 for Application No. PCT/US2010/043817, 9 pages.

(56) References Cited

OTHER PUBLICATIONS

Written Opinion dated Mar. 8, 2011 for Application No. PCT/US2010/046144, 9 pages.
Written Opinion dated Nov. 11, 2010 for Application No. PCT/US2010/040768, 7 pages.
Yant, S., et al. "Somatic integration and long-term transgene expression in normal and haemophilic mice using a DNA transposon system," Nature Genetics, May 2000, pp. 35-41, vol. 25.
Yeung, R.S., et al., "Susceptibility to renal carcinoma in the Eker rat involves a tumor suppressor gene on chromosome 10," Proc. Natl. Acad. Sci. USA, vol. 90, Sep. 1993, pp. 8038-8042.
Yonezawa et al., "Detection of transgene in progeny at different developmental stages following testis-mediated gene transfer." Mol Reprod Dev (2001); 60(2): 196-201.
Zan, et al. "Production of knockout rats using ENU mutagenesis and a yeast-based screening assay", Nat Biotechnol 2003, 21:645-651.
Zhang, L. et al. "DNA-binding activity and subunit interaction of the mariner transposase," Nucleic Acids Research, 2001, pp. 3566-3575, vol. 29, No. 17.
Zhang, Y. et al., "In vitro and in vivo models for assessing drug efflux transporter activity," Advanced Drug Delivery reviews, Jan. 21, 2003, vol. 55(1), pp. 31-51.
Zhou, Q., et al., "Generation of Fertile Cloned Rats by Regulating Oocyte Activation," Science, vol. 302, Nov. 14, 2003, p. 1179.
Request For Ex Parte Reexamination of U.S. Pat. No. 11,089,765 (U.S. Appl. No. 90/015,171), dated Nov. 30, 2022, 85 pages.
Noto, Fallon K., et al., "Novel immunodeficient rat models capable of supporting the growth of human tumor xenografts" [abstract]. In: Proceedings of the AACR Special Conference: Advances in Modeling Cancer in Mice: Technology, Biology, and Beyond; Sep. 24-27, 2017; Orlando, Florida. Philadelphia (PA): AACR; Cancer Res 2018;78(10 Suppl):Abstract nr B36.
Noto, Fallon K., et al., "Novel immunodeficient rat models capable of supporting the growth of human tumor xenografts" Hera BioLabs [online] <https://www.herabiolabs.com/wp-content/uploads/2017/10/AACR-Advances-to-modeling-cancer-in-mice-Sept-2017-Poster-Noto.pdf> (Sep. 2017); 1 page.
Azpilikueta et al., "Successful Immunotherapy against a Transplantble Mouse Squamous Lung Carcinoma with Anti-PD-1 and Anti-CD137 Monoclonal Antibodies," Journal of Thoracic Oncology 11(4):524-536 (2016).
NCBI accession No. XM_032902242.1 , pp. 1-2 (Year: 2010).
Shultz et al., "Human Cancer Growth and Therapy in NOD/SCID/IL2Rγnull (NSG) Mice," Cold Spring Harb Protoc. 4(7):694-708 (2014).
Xue et al Journal of Immunology, vol. 188, No. 1, Supp. Meeting abstract No. 126.30, abstract p. 1 (Year: 2012).

\* cited by examiner

Breeding and Screening

Figure 3.

Sequences encoding the transposases for the DNA transposons Sleeping Beauty and piggyBac:

SB Transposase:
ATGGGAAAATCAAAAGAAATCAGCCAAGACCTCAGAAAAAAATTGTAG
ACCTCCACAAGTCTGGTTCATCCTTGGGAGCAATTTCCAAACGCCTGAAA
GTACCACGTTCATCTGTACAAACAATAGTACGCAAGTATAAACACCATGG
GACCACGCAGCCGTCATACCGCTCAGGAAGGAGACGCGTTCTGTCTCCTA
GAGATGAACGTACTTTGGTGCGAAAAGTGCAAATCAATCCCAGAACAACA
GCAAAGGACCTTGTGAAGATGCTGGAGGAAACAGGTACAAAAGTATCTAT
ATCCACAGTAAAACGAGTCCTATATCGACATAACCTGAAAGGCCGCTCAG
CAAGGAAGAAGCCACTGCTCCAAAACCGACATAAGAAAGCCAGACTACG
GTTTGCAACTGCACATGGGGACAAAGATCGTACTTTTGGAGAAATGTCC
TCTGGTCTGATGAAACAAAATAGAACTGTTTGGCCATAATGACCATCGT
TATGTTTGGAGGAAGAAGGGGGAGGCTTGCAAGCCGAAGAACACCATCC
CAACCGTGAAGCACGGGGGTGGCAGCATCATGTTGTGGGGGTGCTTTGCT
GCAGGAGGGACTGGTGCACTTCACAAAATAGATGGCATCATGAGGAAGG
AAAATTATGTGGATATATTGAAGCAACATCTCAAGACATCAGTCAGGAAG
TTAAAGCTTGGTCGCAAATGGGTCTTCCAAATGGACAATGACCCCAAGCA
TACTTCCAAAGTTGTGGCAAAATGGCTTAAGGACAACAAAGTCAAGGTAT
TGGAGTGGCCATCACAAAGCCCTGACCTCAATCCTATAGAAAATTTGTGG
GCAGAACTGAAAAAGCGTGTGCGAGCAAGGAGGCCTACAAACCTGACTC
AGTTACACCAGCTCTGTCAGGAGGAATGGGCCAAAATTCACCCAACTTAT
TGTGGGAAGCTTGTGGAAGGCTACCCGAAACGTTTGACCCAAGTTAAACA
ATTTAAAGGCAATGCTACCAAATACTAG SB 5' ITR:
CAGTTGAAGTCGGAAGTTTACATACACTTAAGTTGGAGTCATTAAAACTC
GTTTTTCAACTACTCCACAAATTTCTTGTTAACAAACAATAGTTTTGGCAA
GTCAGTTAGGACATCTACTTTGTGCATGACACAAGTCATTTTTCCAACAAT
TGTTTACAGACAGATTATTTCACTTATAATTCACTGTATCACAATTCCAGT
GGGTCAGAAGTTTACATACACTAAGT SB 3' ITR:
ATTGAGTGTATGTAAACTTCTGACCCACTGGGAATGTGATGAAAGAAATA
AAAGCTGAAATGAATCATTCTCTCTACTATTATTCTGATATTTCACATTCTT
AAAATAAAGTGGTGATCCTAACTGACCTAAGACAGGGAATTTTACTAGG
ATTAAATGTCAGGAATTGTGAAAAGTGAGTTTAAATGTATTTGGCTAAG
GTGTATGTAAACTTCCGACTTCAACTG PB Transposase:
ATGGGTAGTTCTTTAGACGATGAGCATATCCTCTCTGCTCTTCTGCAAAGC
GATGACGAGCTTGTTGGTGAGGATTCTGACAGTGAAATATCAGATCACGT
AAGTGAAGATGACGTCCAGAGCGATACAGAAGAAGCGTTTATAGATGAG Figure 3 (continued).

GTACATGAAGTGCAGCCAACGTCAAGCGGTAGTGAAATATTAGACGAACA
AAATGTTATTGAACAACCAGGTTCTTCATTGGCTTCTAACAGAATCTTGAC
CTTGCCACAGAGGACTATTAGAGGTAAGAATAAACATTGTTGGTCAACTT
CAAAGTCCACGAGGCGTAGCCGAGTCTCTGCACTGAACATTGTCAGATCT
CAAAGAGGTCCGACGCGTATGTGCCGCAATATATATGACCCACTTTTATG
CTTCAAACTATTTTTACTGATGAGATAATTTCGGAATTGTAAATGGAC
AAATGCTGAGATATCATTGAAACGTCGGGAATCTATGACAGGTGCTACAT
TTCGTGACACGAATGAAGATGAAATCTATGCTTTCTTTGGTATTCTGGTAA
TGACAGCAGTGAGAAAGATAACCACATGTCCACAGATGACCTCTTTGAT
CGATCTTTGTCAATGGTGTACGTCTCTGTAATGAGTCGTGATCGTTTTGAT
TTTTTGATACGATGTCTTAGAATGGATGACAAAGTATACGGCCCACACTT
CGAGAAAACGATGTATTTACTCCTGTTAGAAAAATATGGGATCTCTTTATC
CATCAGTGCATACAAAATTACACTCCAGGGGCTCATTTGACCATAGATGA
ACAGTTACTTGGTTTTAGAGGACGGTGTCCGTTTAGGATGTATATCCCAAA
CAAGCCAAGTAAGTATGGAATAAAAATCCTCATGATGTGTGACAGTGGTA
CGAAGTATATGATAAATGGAATGCCTTATTTGGGAAGAGGAACACAGACC
AACGGAGTACCACTCGGTGAATACTACGTGAAGGAGTTATCAAAGCCTGT
GCACGGTAGTTGTCGTAATATTACGTGTGACAATTGGTTCACCTCAATCCC
TTTGGCAAAAACTTACTACAAGAACCGTATAAGTTAACCATTGTGGAA
CCGTGCGATCAAACAAACGCGAGATACCGGAAGTACTGAAAAACAGTCG
CTCCAGGCCAGTGGGAACATCGATGTTTTGTTTTGACGGACCCCTTACTCT
CGTCTCATATAAACCGAAGCCAGCTAAGATGGTATACTTATTATCATCTTG
TGATGAGGATGCTTCTATCAACGAAAGTACCGGTAAACCGCAAATGGTTA
TGTATTATAATCAAACTAAAGGCGGAGTGGACACGCTAGACCAAATGTGT
TCTGTGATGACCTGCAGTAGGAAGACGAATAGGTGGCCTATGGCATTATT
GTACGGAATGATAAACATTGCCTGCATAAATTCTTTTATTATATACAGCCA
TAATGTCAGTAGCAAGGGAGAAAAGGTTCAAAGTCGCAAAAAATTTATGA
GAAACCTTTACATGAGCCTGACGTCATCGTTTATGCGTAAGCGTTTAGAAG
CTCCTACTTTGAAGAGATATTTGCGCGATAATATCTCTAATATTTTGCCAA
ATGAAGTGCCTGGTACATCAGATGACAGTACTGAAGAGCCAGTAATGAAA
AAACGTACTTACTGTACTTACTGCCCCTCTAAAATAAGGCGAAAGGCAAA
TGCATCGTGCAAAAATGCAAAAAGTTATTTGTCGAGAGCATAATATTG
ATATGTGCCAAAGTTGTTTCTGA

PB 5' ITR:
CCCTAGAAAGATAGTCTGCGTAAAATTGACGCATGCATTCTTGAAATAT
TGCTCTCTCTTTCTAAATAGCGCGAATCCGTCGCTGTGCATTTAGGACATC
TCAGTCGCCGCTTGGAGCTCCCGTGAGGCGTGCTTGTCAATGCGGTAAGT
GTCACTGATTTTGAACTATAACGACCGCGTGAGTCAAAATGACGCATGAT
TATCTTTTACGTGACTTTTAAGATTTAACTCATACGATAATTATATTGTTAT
TTCATGTTCTACTTACGTGATAACTTATTATATATATTTTCTTGTTATAG
ATATC (minimal sequence is underlined and bold, i.e., first 35 bp)

PB 3' ITR:
TAAAAGTTTTGTTACTTTATAGAAGAAATTTTGAGTTTTGTTTTTTTTAA
TAAATAAATAAACATAAATAAATTGTTTGTTGAATTTATTATTAGTATGTA

Figure 3 (continued).

AGTGTAAATATAATAAAACTTAATATCTATTCAAATTAATAAATAAACCTC
GATATACAGACCGATAAAACA**CATGCGTCAATTTTACGCATGATTATCT
TTAACGTACGTCACAATATGATTATCTTTCTAGGG** (minimal sequence is underlined and bold, i.e., first 35 bp)

Figure 4 Legend

- SB-transposase transcription
- SB-transposase
- SB-transposon ITR recognition sequences
- Gene trap cassette
- Gene trap cassette with flanking SB transposon ITR recognition sequences

SEQUENCE LISTING

<160> NUMBER OF SEQ ID NOS: 17

<210> SEQ ID NO 1
<211> LENGTH: 352
<212> TYPE: PRT
<213> ORGANISM: Rattus norvegicus

<400> SEQUENCE: 1

Met Ala Gln Thr Pro Ala Phe Asn Lys Pro Lys Val Glu Leu His Val
1               5                   10                  15

His Leu Asp Gly Ala Ile Lys Pro Glu Thr Ile Leu Tyr Tyr Gly Lys
            20                  25                  30

Lys Arg Gly Ile Asp Leu Pro Ala Asp Thr Val Glu Gly Leu Arg Asn
        35                  40                  45

Ile Ile Gly Met Asp Lys Pro Leu Ser Leu Pro Asp Phe Leu Ala Lys
    50                  55                  60

Phe Asp Tyr Tyr Met Pro Ala Ile Ala Gly Cys Arg Glu Ala Ile Lys
65                  70                  75                  80

Arg Ile Ala Tyr Glu Phe Val Glu Met Lys Ala Lys Glu Gly Val Val
                85                  90                  95

Tyr Val Glu Val Arg Tyr Ser Pro His Leu Leu Ala Asn Ser Lys Val
            100                 105                 110

Asp Pro Ile Pro Trp Asn Gln Ala Glu Gly Asp Leu Thr Pro Asp Glu
        115                 120                 125

Val Val Asp Leu Val Asn Gln Gly Leu Gln Glu Gly Glu Gln Ala Phe
    130                 135                 140

Gly Ile Lys Val Arg Ser Ile Leu Cys Cys Met Arg His Gln Pro Ser
145                 150                 155                 160

Trp Ser Pro Glu Val Leu Glu Leu Cys Lys Lys Tyr His Gln Lys Thr
                165                 170                 175

Val Val Ala Met Asp Leu Ala Gly Asp Glu Thr Ile Glu Gly Ser Ser
            180                 185                 190

Leu Phe Pro Gly His Val Glu Ala Tyr Glu Gly Ala Val Lys Asp Gly
        195                 200                 205

Ile His Arg Thr Val His Ala Gly Glu Val Gly Ser Ala Glu Val Val
    210                 215                 220

Arg Glu Ala Val Asp Ile Leu Lys Thr Glu Arg Val Gly His Gly Tyr
225                 230                 235                 240

His Thr Ile Glu Asp Glu Ala Leu Tyr Asn Arg Leu Leu Lys Glu Asn
                245                 250                 255

Met His Phe Glu Val Cys Pro Trp Ser Ser Tyr Leu Thr Gly Ala Trp
            260                 265                 270

Asn Pro Lys Thr Thr His Ala Val Val Arg Phe Lys Asp Asp Gln Ala
        275                 280                 285

Asn Tyr Ser Leu Asn Ser Asp Asp Pro Leu Ile Phe Lys Ser Thr Val
    290                 295                 300

Asp Thr Asp Tyr Gln Met Val Lys Lys Asp Met Gly Phe Thr Glu Glu
305                 310                 315                 320

Glu Phe Lys Arg Leu Asn Ile Asn Ala Ala Lys Ser Ser Phe Leu Pro
                325                 330                 335

Glu Asp Glu Lys Lys Glu Leu Leu Glu Arg Leu Tyr Lys Glu Tyr Gln
            340                 345                 350

<210> SEQ ID NO 2
<211> LENGTH: 352

```
<212> TYPE: PRT
<213> ORGANISM: Mus musculus

<400> SEQUENCE: 2

Met Ala Gln Thr Pro Ala Phe Asn Lys Pro Lys Val Glu Leu His Val
1               5                   10                  15

His Leu Asp Gly Ala Ile Lys Pro Glu Thr Ile Leu Tyr Phe Gly Lys
            20                  25                  30

Lys Arg Gly Ile Ala Leu Pro Ala Asp Thr Val Glu Glu Leu Arg Asn
            35                  40                  45

Ile Ile Gly Met Asp Lys Pro Leu Ser Leu Pro Gly Phe Leu Ala Lys
        50                  55                  60

Phe Asp Tyr Tyr Met Pro Val Ile Ala Gly Cys Arg Glu Ala Ile Lys
65                  70                  75                  80

Arg Ile Ala Tyr Glu Phe Val Glu Met Lys Ala Lys Gly Val Val
                85                  90                  95

Tyr Val Glu Val Arg Tyr Ser Pro His Leu Leu Ala Asn Ser Lys Val
                100                 105                 110

Asp Pro Met Pro Trp Asn Gln Thr Glu Gly Asp Val Thr Pro Asp Asp
            115                 120                 125

Val Val Asp Leu Val Asn Gln Gly Leu Gln Glu Gly Gln Ala Phe
        130                 135                 140

Gly Ile Lys Val Arg Ser Ile Leu Cys Cys Met Arg His Gln Pro Ser
145                 150                 155                 160

Trp Ser Leu Glu Val Leu Glu Leu Cys Lys Lys Tyr Asn Gln Lys Thr
                165                 170                 175

Val Val Ala Met Asp Leu Ala Gly Asp Glu Thr Ile Glu Gly Ser Ser
                180                 185                 190

Leu Phe Pro Gly His Val Glu Ala Tyr Glu Gly Ala Val Lys Asn Gly
            195                 200                 205

Ile His Arg Thr Val His Ala Gly Glu Val Gly Ser Pro Glu Val Val
        210                 215                 220

Arg Glu Ala Val Asp Ile Leu Lys Thr Glu Arg Val Gly His Gly Tyr
225                 230                 235                 240

His Thr Ile Glu Asp Glu Ala Leu Tyr Asn Arg Leu Leu Lys Glu Asn
                245                 250                 255

Met His Phe Glu Val Cys Pro Trp Ser Ser Tyr Leu Thr Gly Ala Trp
            260                 265                 270

Asp Pro Lys Thr Thr His Ala Val Val Arg Phe Lys Asn Asp Lys Ala
        275                 280                 285

Asn Tyr Ser Leu Asn Thr Asp Asp Pro Leu Ile Phe Lys Ser Thr Leu
    290                 295                 300

Asp Thr Asp Tyr Gln Met Thr Lys Lys Asp Met Gly Phe Thr Glu Glu
305                 310                 315                 320

Glu Phe Lys Arg Leu Asn Ile Asn Ala Ala Lys Ser Ser Phe Leu Pro
                325                 330                 335

Glu Glu Glu Lys Lys Glu Leu Leu Glu Arg Leu Tyr Arg Glu Tyr Gln
                340                 345                 350

<210> SEQ ID NO 3
<211> LENGTH: 117
<212> TYPE: DNA
<213> ORGANISM: Artificial Sequence
<220> FEATURE:
<223> OTHER INFORMATION: Tc1/mariner-type
```

<400> SEQUENCE: 3

```
taggttcctg ggttcaaact caggttgtca tgctttgtgg aaggcacctt cacccactga    60
gccatcttac cagttccaga atttgacact tgactttttct caaagcacta ttcctag     117
```

<210> SEQ ID NO 4
<211> LENGTH: 1023
<212> TYPE: DNA
<213> ORGANISM: Artificial Sequence
<220> FEATURE:
<223> OTHER INFORMATION: TC1/Mariner-Type transposon from salmonid fish

<400> SEQUENCE: 4

```
atgggaaaat caaaagaaat cagccaagac ctcagaaaaa aaattgtaga cctccacaag    60
tctggttcat ccttgggagc aatttccaaa cgcctgaaag taccacgttc atctgtacaa   120
acaatagtac gcaagtataa acaccatggg accacgcagc cgtcataccg ctcaggaagg   180
agacgcgttc tgtctcctag agatgaacgt actttggtgc gaaaagtgca atcaatccc    240
agaacaacag caaaggacct tgtgaagatg ctggaggaaa caggtacaaa agtatctata   300
tccacagtaa aacgagtcct atatcgacat aacctgaaag gccgctcagc aaggaagaag   360
ccactgctcc aaaaccgaca taagaaagcc agactacggg ttgcaactgc catgggggac   420
aaagatcgta cttttttggag aaatgtcctc tggtctgatg aaacaaaaat agaactgttt   480
ggccataatg accatcgtta tgtttggagg aagaagggg aggcttgcaa gccgaagaac   540
accatcccaa ccgtgaagca cggggggtggc agcatcatgt tgtgggggtg ctttgctgca   600
ggagggactg gtgcacttca caaatagat ggcatcatga ggaaggaaaa ttatgtggat   660
atattgaagc aacatctcaa gacatcagtc aggaagttaa agcttggtcg caaatgggtc   720
ttccaaatgg acaatgaccc caagcatact tccaaagttg tggcaaaatg gcttaaggac   780
aacaaagtca aggtattgga gtggccatca caaagccctg acctcaatcc tatagaaaat   840
ttgtgggcag aactgaaaaa gcgtgtgcga gcaaggaggc ctacaaacct gactcagtta   900
caccagctct gtcaggagga atgggccaaa attcacccaa cttattgtgg gaagcttgtg   960
gaaggctacc cgaaacgttt gacccaagtt aaacaattta aaggcaatgc taccaaatac  1020
tag                                                                 1023
```

<210> SEQ ID NO 5
<211> LENGTH: 229
<212> TYPE: DNA
<213> ORGANISM: Artificial Sequence
<220> FEATURE:
<223> OTHER INFORMATION: TC1/mariner-type transposon from salmonid fish

<400> SEQUENCE: 5

```
cagttgaagt cggaagttta catacactta agttggagtc attaaaactc gttttttcaac    60
tactccacaa atttcttgtt aacaaacaat agttttggca agtcagttag gacatctact   120
ttgtgcatga cacaagtcat tttttccaaca attgttttaca gacagattat ttcacttata   180
attcactgta tcacaattcc agtgggtcag aagtttacat acactaagt                229
```

<210> SEQ ID NO 6
<211> LENGTH: 229
<212> TYPE: DNA
<213> ORGANISM: Artificial Sequence
<220> FEATURE:
<223> OTHER INFORMATION: TC1/mariner type tansposon from salmonid fish

<400> SEQUENCE: 6

```
attgagtgta tgtaaacttc tgacccactg ggaatgtgat gaaagaaata aaagctgaaa      60
tgaatcattc tctctactat tattctgata tttcacattc ttaaaataaa gtggtgatcc     120
taactgacct aagacaggga attttacta ggattaaatg tcaggaattg tgaaaaagtg     180
agtttaaatg tatttggcta aggtgtatgt aaacttccga cttcaactg                229
```

<210> SEQ ID NO 7
<211> LENGTH: 1785
<212> TYPE: DNA
<213> ORGANISM: Artificial Sequence
<220> FEATURE:
<223> OTHER INFORMATION: Tc1/mariner-type transposon from cabbage
      looper moth Trichoplusia ni

<400> SEQUENCE: 7

```
atgggtagtt ctttagacga tgagcatatc ctctctgctc ttctgcaaag cgatgacgag      60
cttgttggtg aggattctga cagtgaaata tcagatcacg taagtgaaga tgacgtccag     120
agcgatacag aagaagcgtt tatagatgag gtacatgaag tgcagccaac gtcaagcggt     180
agtgaaatat tagacgaaca aaatgttatt gaacaaccag gttcttcatt ggcttctaac     240
agaatcttga cctgccaca gaggactatt agaggtaaga ataaacattg ttggtcaact     300
tcaaagtcca cgaggcgtag ccgagtctct gcactgaaca ttgtcagatc tcaaagaggt     360
ccgacgcgta tgtgccgcaa tatatatgac ccactttat gcttcaaact attttttact     420
gatgagataa tttcggaaat tgtaaaatgg acaaatgctg agatatcatt gaaacgtcgg     480
gaatctatga caggtgctac atttcgtgac acgaatgaag atgaaatcta tgctttcttt     540
ggtattctgg taatgacagc agtgagaaaa gataaccaca tgtccacaga tgacctcttt     600
gatcgatctt tgtcaatggt gtacgtctct gtaatgagtc gtgatcgttt tgattttttg     660
atacgatgtc ttagaatgga tgacaaaagt atacggccca cacttcgaga aaacgatgta     720
tttactcctg ttagaaaaat atgggatctc tttatccatc agtgcataca aaattacact     780 ccagggctc atttgaccat agatgaacag ttacttggtt ttagaggacg gtgtccgttt     840
aggatgtata tcccaaacaa gccaagtaag tatggaataa aaatcctcat gatgtgtgac     900
agtggtacga agtatatgat aaatggaatg cctatttgg gaagaggaac acagaccaac     960
ggagtaccac tcggtgaata ctacgtgaag gagttatcaa agcctgtgca cggtagttgt    1020
cgtaatatta cgtgtgacaa ttggttcacc tcaatcccct tggcaaaaaa cttactacaa    1080
gaaccgtata agttaaccat tgtgggaacc gtgcgatcaa acaaacgcga gataccggaa    1140
gtactgaaaa acagtcgctc caggccagtg ggaacatcga tgttttgttt tgacggaccc    1200
cttactctcg tctcatataa accgaagcca gctaagatgg tatacttatt atcatcttgt    1260
gatgaggatg cttctatcaa cgaaagtacc ggtaaaccgc aaatggttat gtattataat    1320
caaactaaag gcggagtgga cacgctagac caaatgtgtt ctgtgatgac ctgcagtagg    1380
aagacgaata ggtggcctat ggcattattg tacggaatga taaacattgc ctgcataaat    1440 tctttatta tatacagcca taatgtcagt agcaagggag aaaaggttca agtcgcaaa    1500 aaatttatga gaacccttta catgagcctg acgtcatcgt ttatgcgtaa gcgtttagaa    1560
gctcctactt tgaagagata tttgcgcgat aatatctcta atattttgcc aaatgaagtg    1620
cctggtacat cagatgacag tactgaagag ccagtaatga aaaaacgtac ttactgtact    1680
tactgcccct ctaaataaag gcgaaaggca aatgcatcgt gcaaaaatg caaaaaagtt    1740 atttgtcgag agcataatat tgatatgtgc caaagttgtt tctga                   1785
```

<210> SEQ ID NO 8
<211> LENGTH: 309
<212> TYPE: DNA
<213> ORGANISM: Artificial Sequence
<220> FEATURE:
<223> OTHER INFORMATION: inverted terminal repeat from Tc1/mariner-type
      DNA transposon from cabbage looper moth Trichoplusia ni

<400> SEQUENCE: 8

```
ccctagaaag atagtctgcg taaaattgac gcatgcattc ttgaaatatt gctctctctt      60
tctaaatagc gcgaatccgt cgctgtgcat ttaggacatc tcagtcgccg cttggagctc     120
ccgtgaggcg tgcttgtcaa tgcggtaagt gtcactgatt ttgaactata acgaccgcgt     180
gagtcaaaat gacgcatgat tatcttttac gtgactttta agatttaact catacgataa     240
ttatattgtt atttcatgtt ctacttacgt gataacttat tatatatata ttttcttgtt     300
atagatatc                                                              309
```

<210> SEQ ID NO 9
<211> LENGTH: 238
<212> TYPE: DNA
<213> ORGANISM: Artificial Sequence
<220> FEATURE:
<223> OTHER INFORMATION: inverted terminal repeat from Tc1/mariner-type
      DNA transposon from cabbage looper moth Trichoplusia ni

<400> SEQUENCE: 9

```
taaaagttttt gttactttat agaagaaatt ttgagttttt gttttttttt aataaataaa      60
taaacataaa taaattgttt gttgaattta ttattagtat gtaagtgtaa atataataaa     120
acttaatatc tattcaaatt aataaataaa cctcgatata cagaccgata aaacacatgc     180
gtcaatttta cgcatgatta tctttaacgt acgtcacaat atgattatct ttctaggg       238
```

<210> SEQ ID NO 10
<211> LENGTH: 1023
<212> TYPE: DNA
<213> ORGANISM: Artificial Sequence
<220> FEATURE:
<223> OTHER INFORMATION: SB Transposase

<400> SEQUENCE: 10

```
atgggaaaat caaagaaat cagccaagac ctcagaaaaa aaattgtaga cctccacaag       60
tctggttcat ccttgggagc aatttccaaa cgcctgaaag taccacgttc atctgtacaa     120
acaatagtac gcaagtataa acaccatggg accacgcagc cgtcataccg ctcaggaagg     180
agacgcgttc tgtctcctag agatgaacgt actttggtgc gaaaagtgca atcaatccc      240 agaacaacag caaaggacct tgtgaagatg ctggaggaaa caggtacaaa agtatctata     300
tccacagtaa aacgagtcct atatcgacat aacctgaaag gccgctcagc aaggaagaag     360
ccactgctcc aaaaccgaca taagaaagcc agactacggt ttgcaactgc catggggac     420 aaagatcgta cttttggag aaatgtcctc tggtctgatg aaacaaaaat gaactgttt      480 ggccataatg accatcgtta tgtttggagg aagaaggggg aggcttgcaa gccgaagaac     540
accatcccaa ccgtgaagca cggggtggc agcatcatgt tgtggggtg ctttgctgca      600 ggagggactg gtgcacttca caaatagat ggcatcatga ggaaggaaaa ttatgtggat      660
atattgaagc aacatctcaa gacatcagtc aggaagttaa agcttggtcg caaatgggtc     720
ttccaaatgg acaatgaccc caagcatact tccaaagttg tggcaaatg gcttaaggac     780
```

```
aacaaagtca aggtattgga gtggccatca caaagccctg acctcaatcc tatagaaaat    840
ttgtgggcag aactgaaaaa gcgtgtgcga gcaaggaggc ctacaaacct gactcagtta    900
caccagctct gtcaggagga atgggccaaa attcacccaa cttattgtgg gaagcttgtg    960
gaaggctacc cgaaacgttt gacccaagtt aaacaattta aggcaatgc taccaaatac   1020 tag                                                                1023

<210> SEQ ID NO 11
<211> LENGTH: 229
<212> TYPE: DNA
<213> ORGANISM: Artificial Sequence
<220> FEATURE:
<223> OTHER INFORMATION: SB 5' ITR

<400> SEQUENCE: 11
cagttgaagt cggaagttta catacactta agttggagtc attaaaactc gttttcaac      60 tactccacaa atttcttgtt aacaaacaat agttttggca agtcagttag gacatctact    120
ttgtgcatga cacaagtcat ttttccaaca attgttaca gacagattat ttcacttata    180
attcactgta tcacaattcc agtgggtcag aagtttacat acactaagt               229

<210> SEQ ID NO 12
<211> LENGTH: 229
<212> TYPE: DNA
<213> ORGANISM: Artificial Sequence
<220> FEATURE:
<223> OTHER INFORMATION: SB 3' ITR

<400> SEQUENCE: 12
attgagtgta tgtaaacttc tgacccactg ggaatgtgat gaaagaaata aaagctgaaa     60
tgaatcattc tctctactat tattctgata tttcacattc ttaaaataaa gtggtgatcc    120
taactgacct aagacaggga attttttacta ggattaaatg tcaggaattg tgaaaaagtg   180
agtttaaatg tatttggcta aggtgtatgt aaacttccga cttcaactg                229

<210> SEQ ID NO 13
<211> LENGTH: 1785
<212> TYPE: DNA
<213> ORGANISM: Artificial Sequence
<220> FEATURE:
<223> OTHER INFORMATION: PB Transposase

<400> SEQUENCE: 13
atgggtagtt cttagacga tgagcatatc ctctctgctc ttctgcaaag cgatgacgag       60
cttgttggtg aggattctga cagtgaaata tcagatcacg taagtgaaga tgacgtccag    120
agcgatacag aagaagcgtt tatagatgag gtacatgaag tgcagccaac gtcaagcggt    180
agtgaaatat tagacgaaca aatgttatt gaacaaccag gttcttcatt ggcttctaac    240
agaatcttga ccttgccaca gaggactatt agaggtaaga ataaacattg ttggtcaact    300
tcaaagtcca cgaggcgtag ccgagtctct gcactgaaca ttgtcagatc tcaaagaggt    360
ccgacgcgta tgtgccgcaa tatatatgac ccacttttat gcttcaaact atttttact    420 gatgagataa tttcggaaat tgtaaaatgg acaaatgctg agatatcatt gaaacgtcgg    480
gaatctatga caggtgctac atttcgtgac acgaatgaag atgaaatcta tgctttcttt    540
ggtattctgg taatgacagc agtgagaaaa gataaccaca tgtccacaga tgacctcttt    600
gatcgatctt tgtcaatggt gtacgtctct gtaatgagtc gtgatcgttt tgattttttg    660
atacgatgtc ttagaatgga tgacaaaagt atacggccca cacttcgaga aaacgatgta    720
```

```
tttactcctg ttagaaaaat atgggatctc tttatccatc agtgcataca aaattacact    780 ccagggctc  atttgaccat agatgaacag ttacttggtt ttagaggacg gtgtccgttt    840
aggatgtata tcccaaacaa gccaagtaag tatggaataa aaatcctcat gatgtgtgac    900
agtggtacga agtatatgat aaatggaatg ccttatttgg gaagaggaac acagaccaac    960
ggagtaccac tcggtgaata ctacgtgaag gagttatcaa agcctgtgca cggtagttgt   1020
cgtaatatta cgtgtgacaa ttggttcacc tcaatccctt tggcaaaaaa cttactacaa   1080
gaaccgtata agttaaccat tgtgggaacc gtgcgatcaa acaaacgcga gataccggaa   1140
gtactgaaaa acagtcgctc caggccagtg ggaacatcga tgttttgttt tgacggaccc   1200
cttactctcg tctcatataa accgaagcca gctaagatgg tatacttatt atcatcttgt   1260
gatgaggatg cttctatcaa cgaaagtacc ggtaaaccgc aaatggttat gtattataat   1320
caaactaaag gcggagtgga cacgctagac caaatgtgtt ctgtgatgac ctgcagtagg   1380
aagacgaata ggtggcctat ggcattattg tacggaatga taaacattgc ctgcataaat   1440
tcttttatta tatacagcca taatgtcagt agcaagggag aaaaggttca agtcgcaaa    1500 aaatttatga gaaaccttta catgagcctg acgtcatcgt ttatgcgtaa gcgtttagaa   1560
gctcctactt tgaagagata tttgcgcgat aatatctcta atattttgcc aaatgaagtg   1620
cctggtacat cagatgacag tactgaagag ccagtaatga aaaaacgtac ttactgtact   1680
tactgcccct ctaaaataag gcgaaaggca aatgcatcgt gcaaaaaatg caaaaaagtt   1740
atttgtcgag agcataatat tgatatgtgc caaagttgtt tctga                   1785

<210> SEQ ID NO 14
<211> LENGTH: 309
<212> TYPE: DNA
<213> ORGANISM: Artificial Sequence
<220> FEATURE:
<223> OTHER INFORMATION: PB 5' ITR

<400> SEQUENCE: 14
ccctagaaag atagtctgcg taaaattgac gcatgcattc ttgaaatatt gctctctctt     60
tctaaatagc gcgaatccgt cgctgtgcat ttaggacatc tcagtcgccg cttggagctc    120
ccgtgaggcg tgcttgtcaa tgcggtaagt gtcactgatt ttgaactata acgaccgcgt    180
gagtcaaaat gacgcatgat tatctttttac gtgacttttta agatttaact catacgataa    240
ttatattgtt atttcatgtt ctacttacgt gataacttat tatatatata ttttcttgtt    300
atagatatc                                                            309

<210> SEQ ID NO 15
<211> LENGTH: 238
<212> TYPE: DNA
<213> ORGANISM: Artificial Sequence
<220> FEATURE:
<223> OTHER INFORMATION: PB 3' ITR

<400> SEQUENCE: 15
taaaagtttt gttactttat agaagaaatt ttgagttttt gtttttttt aataaataaa      60 taaacataaa taaattgttt gttgaattta ttattagtat gtaagtgtaa atataataaa    120
acttaatatc tattcaaatt aataaataaa cctcgatata cagaccgata aaacacatgc    180 gtcaattta cgcatgatta tctttaacgt acgtcacaat atgattatct ttctaggg       238

<210> SEQ ID NO 16
```

```
<211> LENGTH: 6
<212> TYPE: PRT
<213> ORGANISM: Unknown
<220> FEATURE:
<223> OTHER INFORMATION: exemplary polypeptide sequence

<400> SEQUENCE: 16

Ala Cys Asp Glu Phe Gly
1               5

<210> SEQ ID NO 17
<211> LENGTH: 6
<212> TYPE: PRT
<213> ORGANISM: Unknown
<220> FEATURE:
<223> OTHER INFORMATION: exemplary polypeptide sequence

<400> SEQUENCE: 17

Ala Cys Asp His Ile Lys
1               5
```

GENETICALLY MODIFIED RAT MODELS FOR SEVERE COMBINED IMMUNODEFICIENCY (SCID)

CROSS REFERENCE TO RELATED APPLICATIONS

This application is a continuation of U.S. application Ser. No. 17/335,568, filed Jun. 1, 2021, which is a continuation of U.S. application Ser. No. 15/810,272, filed Nov. 13, 2017, now U.S. Pat. No. 11,089,765, issued Aug. 17, 2021, which is a continuation of U.S. application Ser. No. 15/070,275, filed Mar. 15, 2016, now abandoned; which is a continuation of U.S. Application No. 13/391,307, filed Feb. 20, 2012, now U.S. Pat. No. 9,314,005, issued Apr. 19, 2016; which is a U.S. National Phase application of PCT/US2010/040768, filed Jul. 1, 2010, which claims the benefit of priority from U.S. Provisional Application No. 61/222,327, filed Jul. 1, 2009, the contents of each of which are incorporated by reference in their entireties for all purposes.

INCORPORATION OF SEQUENCE LISTING

The contents of the text file, a computer readable format copy of the Sequence Listing named "HRBI_003_05US_SubSeqList_ST25", which was recorded on Jun. 28, 2022 and is 18.9 kilobytes in size, are hereby incorporated by reference in its entirety.

BACKGROUND OF THE INVENTION

Gene modification is a process whereby a specific gene, or a fragment of that gene, is altered. This alteration of the targeted gene may result in a change in the level of RNA and/or protein that is encoded by that gene, or the alteration may result in the targeted gene encoding a different RNA or protein than the untargeted gene. The modified gene may be studied in the context of a cell, or, more preferably, in the context of a genetically modified animal.

Genetically modified animals are among the most useful research tools in the biological sciences. An example of a genetically modified animal is a transgenic animal, which has a heterologous (i.e., foreign) gene, or gene fragment, incorporated into their genome that is passed on to their offspring. Although there are several methods of producing genetically modified animals, the most widely used is microinjection of DNA into single cell embryos. These embryos are then transferred into pseudopregnant recipient foster mothers. The offspring are then screened for the presence of the new gene, or gene fragment. Potential applications for genetically modified animals include discovering the genetic basis of human and animal diseases, generating disease resistance in humans and animals, gene therapy, toxicology studies, drug testing, and production of improved agricultural livestock.

Identification of novel genes and characterization of their function using mutagenesis has also been shown to be productive in identifying new drugs and drug targets. Creating in vitro cellular models that exhibit phenotypes that are clinically relevant provides a valuable substrate for drug target identification and screening for compounds that modulate not only the phenotype but also the target(s) that controls the phenotype. Modulation of such a target can provide information that validates the target as important for therapeutic intervention in a clinical disorder when such modulation of the target serves to modulate a clinically relevant phenotype.

Animal models exhibiting Severe Combined Immunodeficiency (SCID) have and important advantage over animals with more limited immunodeficiencies due to the lack of B-cells, T-cells and NK-cells. SCID animals readily accept xenografts and, are therefore, a crucial model for cancer research. The SCID animal can receive grafts and other tissue transplants (e.g., lymphocytes or tumor cells) without eliciting an immune response. SCID animal models are used for xenotransplantation of cell lines such as cultured human cancer cell lines or cells from surgically resected tumors. For example, fragments of tumors resected from patients can transplanted into an anesthetized SCID mouse. The xenografts are stable (i.e. not rejected by the host's immune system), and are useful for a wide range of studies. The histological studies of such xenografts show that they maintain major features such as cysts, and mono-or-multilocular cavities, as the original tumors. The SCID animal xenografts are therefore relevant for human tumor biology studies. SCID animal xenografts are also useful for examination of known cancer genes such as tumor suppressor genes and the potential discovery of new cancer targets. In one method, tumor tissues from the SCID animal xenografts are taken, RNA is extracted, reverse transcribed, and PCR amplified. The analysis of sequences can identify mutations in genes that are associated with the tumor or cancer. In another method, a functional assay can be performed to identify genes that may be over or under expressed in the tumor. The SCID animal xenografts are also useful for studies of the efficacy of potential oncoceuticals. In one method, a radiological growth assay is employed to determine tumor growth delay. The tumor is typically given a single dose of irradiation treatment, and the tumor size is scored to calculate the growth delay. In a similar fashion, therapeutic agents such as compounds and biologics can be tested for tumor or metastasis suppression.

Since the SCID model lacks peripheral B- and T-cell activity, the animal accepts human grafts including human lymphoid tissues. This technique gives a SCID model that is reconstituted with human immune system components. One example is the engraftment of human peripheral blood lymphocytes (PBLs), thymus, and liver tissue into a SCID mouse. The SCID model can therefore mimic human immune response better than a wild type animal before actual human clinical trials.

Having the capability of generating rats with humanized organs using primary cells either from healthy patients or from patients with genetic lesions associated with various disease states would provide unique and valuable resources for drug discovery and therapeutic research programs. The organs include, but are not limited to, liver, pancreas, skin and intestine. Since the SCID rats lack peripheral T-cell and NK-cell activity, transplanted human cells will not be rejected and will incorporate into the tissue at the site of injection. The rat will then contain an organ which consists of significant numbers of human cells. In the best case scenario, the organ will completely be composed of human cells, although organs with lower percentages of human cells remain useful for drug discovery and therapeutic research In some applications it may be more desirable to generate rat organs with lower levels of human cells (chimeric organs) using primary cells either from healthy patients or from patients with genetic lesions associated with various disease states. These models would provide unique and valuable resources for drug discovery and therapeutic research programs. Such examples include, but are not limited to brain, heart and skeletal muscle, where it may not be possible to generate completely humanized organs.

Animal models which exhibit the SCID phenotype are used for immunologic studies. These experiments usually involve but are not limited to the testing for the presence and measurement of leukocyte populations, and the functionality of immunocompetent cells. In order to test for the presence of immune cells, flow cytometry can be done using cells suspensions from the thymuses and spleen. Antibodies can target immune cell surface antigens such as Cd3, and identify leukocytes, which contain B-, T-, and NK-cell populations. Cell numbers can be compared to control populations to indicate whether the immune system has been compromised. To test the functionality of immune cells, one may test the proliferation of spleen cells when stimulated by B- and T-cell mitogens. The mitogens will stimulate cell growth and division in functional immune cells. The amount of proliferation reflects the functionality of immunocompetent cells.

SCID animal models are very useful to test immune response to infectious diseases and pathogens, such as but not limited to *Mycobacterium tuberculosis*. Recurrent *M. tuberculosis* and other infections frequently occur in both SCID patients and SCID animal models. Many experiments can be employed to measure the progression of infectious diseases and alleviation of the disease due to therapeutic intervention. To measure the virulence of bacteria in infectious disease studies, SCID animal models can be infected via aerosol inhalation. Lung cells and tissue are then collected and plated on agar to count the number of colony forming units (CFU). The amount of CFU produced over time is an indicator of disease progression. Residential alveolar macrophages play a substantial role in protection against infectious disease; therefore, cytokine assays can be done to determine what cell types are recruited to the alveolar space during disease progression. Bronchoalveolar lavage cells (BAL) are harvested from the trachea, put on a slide and stained for the presence of cytokines such as Ccl2. The numbers and types of cytokines present are known to play different roles and can be measured to monitor disease progression.

The SCID rat, as compared to other SCID models, is particularly useful for many applications, including but not limited to drug testing, toxicology models, humanized organ production, immunologic, and infectious disease models. The SCID rat has many advantages over the SCID mouse model. The rat is has been known to be a better animal model for many human disease states for over 50 years. The rat performs most major medical assays with a higher proficiency than mice. The size of the rat is also important. Study by instrumentation, nerve conduction, surgery, and imaging are all more efficient in the rat. Blood, tissue, and tumor sampling are all easier and more accurate in the rat. The rat also provides up to ten times more tissue for more conclusive data.

SCID models will provide an immunocompromised model that can serve as a recipient of transplanted stem cells or in vitro differentiated stem cells. Examples of stem cells include, but are not limited to, embryonic, amniotic, umbilical cord-, mesenchymal-, hepatic- or adipose stromal, induced pluripotent cell-derived populations. Stem cells or differentiated stem cells obtained from healthy or diseased patients can be used to produce organs comprised entirely of human cells (humanized organs) or organs with significant percentages of human cells (chimeric organs).

Animal models exhibiting clinically relevant phenotypes are also valuable for drug discovery and development and for drug target identification. For example, mutation of somatic or germ cells facilitates the production of genetically modified offspring or cloned animals having a phenotype of interest. Such animals have a number of uses, for example as models of physiological disorders (e.g., of human genetic diseases) that are useful for screening the efficacy of candidate therapeutic compounds or compositions for treating or preventing such physiological disorders. Furthermore, identifying the gene(s) responsible for the phenotype provides potential drug targets for modulating the phenotype and, when the phenotype is clinically relevant, for therapeutic intervention. In addition, the manipulation of the genetic makeup of organisms and the identification of new genes have important uses in agriculture, for example in the development of new strains of animals and plants having higher nutritional value or increased resistance to environmental stresses (such as heat, drought, or pests) relative to their wild-type or non-mutant counterparts.

Since most eukaryotic cells are diploid, two copies of most genes are present in each cell. As a consequence, mutating both alleles to create a homozygous mutant animal is often required to produce a desired phenotype, since mutating one copy of a gene may not produce a sufficient change in the level of gene expression or activity of the gene product from that in the non-mutated or wild-type cell or multicellular organism, and since the remaining wild-type copy would still be expressed to produce functional gene product at sufficient levels. Thus, to create a desired change in the level of gene expression and/or function in a cell or multicellular organism, at least two mutations, one in each copy of the gene, are often required in the same cell.

In other instances, mutation in multiple different genes may be required to produce a desired phenotype. In some instances, a mutation in both copies of a single gene will not be sufficient to create the desired physiological effects on the cell or multi-cellular organism. However, a mutation in a second gene, even in only one copy of that second gene, can reduce gene expression levels of the second gene to produce a cumulative phenotypic effect in combination with the first mutation, especially if the second gene is in the same general biological pathway as the first gene. This effect can alter the function of a cell or multi-cellular organism. A hypomorphic mutation in either gene alone could result in protein levels that are severely reduced but with no overt effect on physiology. Severe reductions in the level of expression of both genes, however, can have a major impact. This principle can be extended to other instances where mutations in multiple (two, three, four, or more, for example) genes are required cumulatively to produce an effect on activity of a gene product or on another phenotype in a cell or multi-cellular organism. It should be noted that, in this instance, such genes may all be expressed in the same cell type and therefore, all of the required mutations occur in the same cell. However, the genes may normally be expressed in different cell types (for example, secreting the different gene products from the different cells). In this case, the gene products are expressed in different cells but still have a biochemical relationship such that one or more mutations in each gene is required to produce the desired phenotype.

BRIEF SUMMARY OF THE INVENTION

In accordance with the purposes of this invention, as embodied and broadly described herein, this invention relates to the engineering of animal cells, preferably mammalian, more preferably rat, that are deficient due to the disruption of gene(s) or gene product(s) resulting in Severe Combined Immunodeficiency (SCID).

In another aspect, the invention relates to genetically modified rats, as well as the descendants and ancestors of such animals, which are animal models of human SCID and methods of their use.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWING

This invention, as defined in the claims, can be better understood with reference to the following drawings:

FIGS. 1-4 show the process for creating a genetically modified SCID rat model using DNA transposons to create an insertion mutation directly in the germ line.

FIG. 1: Gene modification by DNA transposons,

FIG. 2: Breeding strategy for creating rat knockouts directly in the germ cells with DNA transposons.

FIG. 3: DNA sequences.

FIG. 4: DNA transposon-mediated insertion mutation in *Rattus norvegicus* Ada gene.

Figure 1:
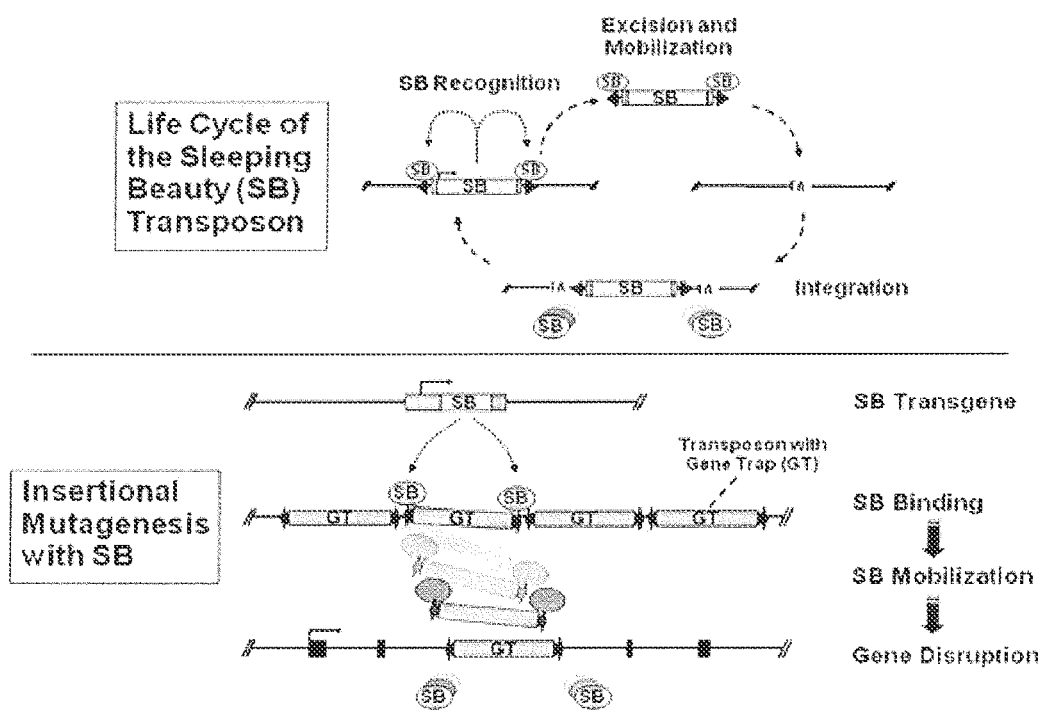

In the following description of the illustrated embodiments, references are made to the accompanying drawings, which form a part hereof, and in which is shown by way of illustration various embodiments in which the invention may be practiced. It is to be understood that other embodiments may be utilized and structural and functional changes may be made without departing from the scope of the present invention.

DETAILED DESCRIPTION OF THE INVENTION

Definitions

The present invention may be understood more readily by reference to the following detailed description of preferred embodiments of the invention and the Examples included therein and to the Figures and their previous and following description. Although any methods and materials similar or equivalent to those described herein can be used in the practice or testing of the present invention, the preferred methods, devices, and materials are now described. All references, publications, patents, patent applications, and commercial materials mentioned herein are incorporated herein by reference for the purpose of describing and disclosing the materials and/or methodologies which are reported in the publications which might be used in connection with the invention. Nothing herein is to be construed as an admission that the invention is not entitled to antedate such disclosure by virtue of prior invention.

Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

In this specification and in the claims which follow, reference will be made to a number of terms which shall be defined to have the following meanings:

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

"Complementary," as used herein, refers to the subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

A "deletion mutation" means a type of mutation that involves the loss of genetic material, which may be from a single base to an entire piece of chromosome. Deletion of one or more nucleotides in the DNA could alter the reading frame of the gene; hence, it could result in a synthesis of a nonfunctional protein due to the incorrect sequence of amino acids during translation.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed". An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "gene", also called a "structural gene" means a DNA sequence that codes for or corresponds to a particular sequence of amino acids which comprise all or part of one or more proteins or enzymes, and may or may not include introns and regulatory DNA sequences, such as promoter sequences, 5'-untranslated region, or 3'-untranslated region which affect for example the conditions under which the gene is expressed. Some genes, which are not structural genes, may be transcribed from DNA to RNA, but are not translated into an amino acid sequence. Other genes may function as regulators of structural genes or as regulators of DNA transcription.

By "genetically modified" is meant a gene that is altered from its native state (e.g., by insertion mutation, deletion mutation, nucleic acid sequence mutation, or other mutation), or that a gene product is altered from its natural state (e.g., by delivery of a transgene that works in trans on a gene's encoded mRNA or protein, such as delivery of inhibitory RNA or delivery of a dominant negative transgene).

By "exon" is meant a region of a gene which includes sequences which are used to encode the amino acid sequence of the gene product.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature.

As used herein, the term "homology" refers to the subunit sequence identity or similarity between two polymeric molecules e.g., between two nucleic acid molecules, e.g., between two DNA molecules, or two polypeptide molecules. When a subunit position in both of the two molecules is occupied by the same monomeric subunit, e.g., if a position in each of two polypeptide molecules is occupied by phenylalanine, then they are identical at that position. The homology between two sequences, most clearly defined as the % identity, is a direct function of the number of identical positions, e.g., if half (e.g., 5 positions in a polymer 10 subunits in length) of the positions in two polypeptide sequences are identical then the two sequences are 50% identical; if 70% of the positions, e.g., 7 out of 10, are matched or homologous, the two sequences share 70% identity. By way of example, the polypeptide sequences ACDEFG (SEQ ID NO: 16) and ACDHIK (SEQ ID NO: 17) share 50% identity and the nucleotide sequences CAATCG and CAAGAC share 50% identity. It should be understood that a sequence identity of at least 90%, such as 90% identity, 91% identity, 92% identity, 93% identity, 94% identity, 95% identity, 96% identity, 97% identity, 98% identity, or 99% identity applies to all sequences disclosed in the present application.

"Homologous recombination" is the physical exchange of DNA expedited by the breakage and reunion of two non-sister chromatids. In order to undergo recombination the DNA duplexes must have complimentarily. The molecular mechanism is as follows: DNA duplexes pair, homologous strands are nicked, and broken strands exchange DNA between duplexes. The region at the site of recombination is called the hybrid DNA or heteroduplex DNA. Second nicks are made in the other strand, and the second strand crosses over between duplexes. After this second crossover event the reciprocal recombinant or splice recombinant is created. The duplex of one DNA parent is covalently linked to the duplex of another DNA parent. Homologous recombination creates a stretch of heteroduplex DNA.

A "hypomorphic mutation" is a change to the genetic material (usually DNA or RNA), which can be caused by any form of genetic mutation, and causes an decrease in normal gene function without causing a complete absence of normal gene function.

The term "inbred animal" is used herein to refer to an animal that has been interbred with other similar animals of the same species in order to preserve and fix certain characteristics, or to prevent other characteristics from being introduced into the breeding population.

The term "insertional mutation" is used herein to refer the translocation of nucleic acid from one location to another location which is in the genome of an animal so that it is integrated into the genome, thereby creating a mutation in the genome. Insertional mutations can also include knocking out or knocking in of endogenous or exogenous DNA via gene trap or cassette insertion. Exogenous DNA can access the cell via electroporation or chemical transformation. If the exogenous DNA has homology with chromosomal DNA it will align itself with endogenous DNA. The exogenous DNA is then inserted or disrupts the endogenous DNA via two adjacent crossing over events, known as homologous recombination. A targeting vector can use homologous recombination for insertional mutagenesis. Insertional mutagenesis of endogenous or exogenous DNA can also be carried out via DNA transposon. The DNA transposon is a mobile element that can insert itself along with additional exogenous DNA into the genome. Insertional mutagenesis of endogenous or exogenous DNA can be carried out by retroviruses. Retroviruses have a RNA viral genome that is converted into DNA by reverse transcriptase in the cytoplasm of the infected cell. Linear retroviral DNA is transported into the nucleus, and become integrated by an enzyme called integrase. Insertional mutagenesis of endogenous or exogenous DNA can also be done by retrotransposons in which an RNA intermediate is translated into DNA by reverse transcriptase, and then inserted into the genome.

The term "gene knockdown" refers to techniques by which the expression of one or more genes is reduced, either through genetic modification (a change in the DNA of one of the organism's chromosomes) or by treatment with a reagent such as a short DNA or RNA oligonucleotide with a sequence complementary to either an mRNA transcript or a gene. If genetic modification of DNA is done, the result is a "knockdown organism" or "knockdowns".

By "knock-out" is meant an alteration in the nucleic acid sequence that reduces the biological activity of the polypeptide normally encoded therefrom by at least 80% compared to the unaltered gene. The alteration may be an insertion, deletion, frameshift mutation, or missense mutation. Preferably, the alteration is an insertion or deletion, or is a frameshift mutation that creates a stop codon.

An "L1 sequence" or "L1 insertion sequence" as used herein, refers to a sequence of DNA comprising an L1 element comprising a 5' UTR, ORF1 and ORF2, a 3' UTR and a poly A signal, wherein the 3' UTR has DNA (e.g., a gene trap or other cassette) positioned either therein or positioned between the 3' UTR and the poly A signal, which DNA is to be inserted into the genome of a cell.

A "mutation" is a detectable change in the genetic material in the animal, which is transmitted to the animal's progeny. A mutation is usually a change in one or more deoxyribonucleotides, the modification being obtained by, for example, adding, deleting, inverting, or substituting nucleotides. Exemplary mutations include but are not limited to a deletion mutation, an insertion mutation, a nonsense mutation or a missense mutation. Thus, the terms "mutation" or "mutated" as used herein are intended to denote an alteration in the "normal" or "wild-type" nucleotide sequence of any nucleotide sequence or region of the allele. As used herein, the terms "normal" and "wild-type" are intended to be synonymous, and to denote any nucleotide sequence typically found in nature. The terms "mutated" and "normal" are thus defined relative to one another; where a cell has two chromosomal alleles of a gene that differ in nucleotide sequence, at least one of these alleles is a "mutant" allele as that term is used herein. Based on these definitions, an "endogenous SCID gene" is the "wild-type" gene that exists normally in a cell, and a "mutated SCID gene" defines a gene that differs in nucleotide sequence from the wild-type gene.

"Non-homologous end joining (NHEJ)" is a cellular repair mechanism. The NHEJ pathway is defined by the ligation of blunt ended double stand DNA breaks. The pathway is initiated by double strand breaks in the DNA, and works through the ligation of DNA duplex blunt ends. The first step is recognition of double strand breaks and formation of scaffold. The trimming, filling in of single stranded overhangs to create blunt ends and joining is executed by the NHEJ pathway. An example of NHEJ is repair of a DNA cleavage site created by a zinc finger nuclease (ZFN). This would normally be expected to create a small deletion mutation.

"Nucleic Acid sequence mutation" is a mutation to the DNA of a gene that involves change of one or multiple nucleotides. A point mutation which affects a single nucleotide can result in a transition (purine to purine or pyrimidine to pyrimidine) or a transversion (purine to pyrimidine or pyrimidine to purine). A point mutation that changes a codon to represent a different amino acid is a missense mutation. Some point mutations can cause a change in amino acid so that there is a premature stop codon; these mutations are called nonsense mutations. A mutation that inserts or deletes a single base will change the entire downstream sequence and are known as frameshift mutations. Some mutations change a base pair but have no effect on amino acid representation; these are called silent mutations. Mutations to the nucleic acid of a gene can have different consequences based on their location (intron, exon, regulatory sequence, and splice joint).

"Optional" or "optionally" means that the subsequently described event or circumstance may or may not occur, and that the description includes instances where said event or circumstance occurs and instances where it does not.

The term "outbred animal" is used herein to refer to an animal that breeds with any other animal of the same species without regard to the preservation of certain characteristics.

As used herein, the term "phenotype" means any property of a cell or organism. A phenotype can simply be a change in expression of an mRNA or protein. Examples of phenotypes also include, but are in no way limited to, cellular, biochemical, histological, behavioral, or whole organismal properties that can be detected by the artisan. Phenotypes include, but are not limited to, cellular transformation, cell migration, cell morphology, cell activation, resistance or sensitivity to drugs or chemicals, resistance or sensitivity to pathogenic protein localization within the cell (e.g., translocation of a protein from the cytoplasm to the nucleus), resistance or sensitivity to ionizing radiation, profile of secreted or cell surface proteins, (e.g., bacterial or viral) infection, post-translational modifications, protein localization within the cell (e.g., translocation of a protein from the cytoplasm to the nucleus), profile of secreted or cell surface proteins, cell proliferation, signal transduction, metabolic defects or enhancements, transcriptional activity, recombination intermediate joining, DNA damage response, cell or organ transcript profiles (e.g., as detected using gene chips), apoptosis resistance or sensitivity, animal behavior, organ histology, blood chemistry, biochemical activities, gross morphological properties, life span, tumor susceptibility, weight, height/length, immune function, organ function, any disease state, and other properties known in the art. In certain situations and therefore in certain embodiments of the invention, the effects of mutation of one or more genes in a cell or organism can be determined by observing a change in one or more given phenotypes (e.g., in one or more given structural or functional features such as one or more of the phenotypes indicated above) of the mutated cell or organism compared to the same structural or functional feature(s) in a corresponding wild-type or (non-mutated) cell or organism (e.g., a cell or organism in which the gene(s) have not been mutated).

By "plasmid" is meant a circular strand of nucleic acid capable of autosomal replication in plasmid-carrying bacteria. The term includes nucleic acid which may be either DNA or RNA and may be single- or double-stranded. The plasmid of the definition may also include the sequences which correspond to a bacterial origin of replication.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

A "random site" is used herein to refer to a location in the genome where a retrotransposition or transposition or other DNA mutation event takes places, without prior intention of mutation at that particular location. It is also used herein to refer to a location in the genome that is randomly modified by any insertion mutation or deletion mutation or nucleic acid sequence mutation.

The term "regulatory sequence" is defined herein as including promoters, enhancers and other expression control elements such as polyadenylation sequences, matrix attachment sites, insulator regions for expression of multiple genes on a single construct, ribosome entry/attachment sites, introns that are able to enhance expression, and silencers.

By "reporter gene" is meant any gene which encodes a product whose expression is detectable. A reporter gene product may have one of the following attributes, without restriction: fluorescence (e.g., green fluorescent protein), enzymatic activity (e.g., lacZ or luciferase), or an ability to be specifically bound by a second molecule (e.g., biotin or an antibody-recognizable epitope).

By "retrotransposition" as used herein, is meant the process of integration of a sequence into a genome, expression of that sequence in the genome, reverse transcription of the integrated sequence to generate an extrachromosomal copy of the sequence and reintegration of the sequence into the genome.

A "retrotransposition event" is used herein to refer to the translocation of a retrotransposon from a first location to a second location with the preferable outcome being integration of a retrotransposon into the genome at the second location. The process involves a RNA intermediate, and can retrotranspose from one chromosomal location to another or from introduced exogenous DNA to endogenous chromosomal DNA.

By "selectable marker" is meant a gene product which may be selected for or against using chemical compounds, especially drugs. Selectable markers often are enzymes with an ability to metabolize the toxic drugs into non-lethal products. For example, the pac (puromycin acetyl transferase) gene product can metabolize puromycin, the dhfr gene product can metabolize trimethoprim (tmp) and the bla gene product can metabolize ampicillin (amp). Selectable markers may convert a benign drug into a toxin. For example, the HSV tk gene product can change its substrate, FIAU, into a lethal substance. Another selectable marker is one which may be utilized in both prokaryotic and eukaryotic cells. The neo gene, for example, metabolizes and neutralizes the toxic effects of the prokaryotic drug, kanamycin, as well as the eukaryotic drug, G418.

By "selectable marker gene" as used herein is meant a gene or other expression cassette which encodes a protein which facilitates identification of cells into which the selectable marker gene is inserted.

A "specific site" is used herein to refer to a location in the genome that is predetermined as the position where a retrotransposition or transposition event or other DNA mutation will take place. It is also used herein to refer to a specific location in the genome that is modified by any insertion mutation or deletion mutation or nucleic acid sequence mutation.

A "SCID gene" is used herein to refer to a gene which encodes a protein that is associated with the phenotype that is characterized as Severe Combined Immunodeficiency (SCID). This phenotype ranges from early onset (infancy), delayed, and late-onset (adulthood). The phenotype may also vary in the extent of immune insufficiency from severe infections to gradual immunologic debilitation. The phenotype encompasses all B-, T-, and NK-cell deficiencies and combinations of individual cell deficiencies. A "SCID protein" is used herein to refer to a protein product of a gene that is associated with the phenotype that is characterized as SCID.

As used herein, the term "targeted genetic recombination" refers to a process wherein recombination occurs within a DNA target locus present in a host cell or host organism. Recombination can involve either homologous or non-homologous DNA.

The term "transfection" means the introduction of a foreign nucleic acid into a cell. The term "transformation" means the introduction of a "foreign" (i.e. extrinsic or extracellular) gene, DNA or RNA sequence to an ES cell or pronucleus, so that the cell will express the introduced gene or sequence to produce a desired substance in a genetically modified animal.

By "transgenic" is meant any animal which includes a nucleic acid sequence which is inserted by artifice into a cell and becomes a part of the genome of the animal that develops from that cell. Such a transgene may be partly or entirely heterologous to the transgenic animal. Although transgenic mice represent another embodiment of the invention, other transgenic mammals including, without limitation, transgenic rodents (for example, hamsters, guinea pigs, rabbits, and rats), and transgenic pigs, cattle, sheep, and goats are included in the definition.

By "transposition" as used herein, is meant the process of one DNA sequence insertion into another (location) without relying on sequence homology. The DNA element can be transposed from one chromosomal location to another or from introduction of exogenous DNA and inserted into the genome.

A "transposition event" or "transposon insertion sequence" is used herein to refer to the translocation of a DNA transposon either from one location on the chromosomal DNA to another or from one location on introduced exogenous DNA to another on the chromosomal DNA.

By "transposon" or "transposable element" is meant a linear strand of DNA capable of integrating into a second strand of DNA which may be linear or may be a circularized plasmid. Transposons often have target site duplications, or remnants thereof, at their extremities, and are able to integrate into similar DNA sites selected at random, or nearly random. Preferred transposons have a short (e.g., less than 300) base pair repeat at either end of the linear DNA. By "transposable elements" is meant any genetic construct including but not limited to any gene, gene fragment, or nucleic acid that can be integrated into a target DNA sequence under control of an integrating enzyme, often called a transposase.

A coding sequence is "under the control of" or "operatively associated with" transcriptional and translational control sequences in a cell when RNA polymerase transcribes the coding sequence into mRNA, which is then trans-RNA spliced (if it contains introns) and translated, in the case of mRNA, into the protein encoded by the coding sequence.

The term "variant" may also be used to indicate a modified or altered gene, DNA sequence, enzyme, cell, etc., i.e., any kind of mutant.

The term "vector" is used interchangeably with the terms "construct", "cloning vector" and "expression vector" and means the vehicle by which a DNA or RNA sequence (e.g., a foreign gene) can be introduced into a host cell, (e.g., ES cell or pronucleus) so as to transform the host and promote expression (e.g., transcription and translation) of the introduced sequence including but not limited to plasmid, phage, transposons, retrotransposons, viral vector, and retroviral vector. By "non-viral vector" is meant any vector that does not comprise a virus or retrovirus.

A "vector sequence" as used herein, refers to a sequence of DNA comprising at least one origin of DNA replication and at least one selectable marker gene.

For the purposes of the present invention, the term "zinc finger nuclease" or "ZFN" refers to a chimeric protein molecule comprising at least one zinc finger DNA binding domain effectively linked to at least one nuclease or part of a nuclease capable of cleaving DNA when fully assembled. Ordinarily, cleavage by a ZFN at a target locus results in a double stranded break (DSB) at that locus.

The present invention provides a desired rat or a rat cell which contains a predefined, specific and desired alteration rendering the rat or rat cell predisposed to Severe Combined Immunodeficiency (SCID) and its variations (autosomal recessive, ionizing radiation sensitive, X-linked, microcephaly, growth retardation). Specifically, the invention pertains to a genetically altered rat, or a rat cell in culture, that is defective in at least one of two alleles of a SCID gene such as the Ada gene, the Rag1 gene, etc. In one embodiment, the SCID gene is the Ada gene. In another embodiment, the SCID gene is one of several known SCID genes, such as (Rag1, Rag2, Dclre1c, Nhej1, Jak3, Il7r, Ptprc, Cd3d, Cd3e, Il2rg, Prkdc Sirpa, Foxn1). The inactivation of at least one of these SCID alleles results in an animal with a higher susceptibility to Severe Combined Immunodeficiency (SCID) induction. In one embodiment, the genetically altered animal is a rat of this type and is able to serve as a useful model for SCID and as a test animal for oncology and other studies. The invention additionally pertains to the use of such rats or rat cells, and their progeny in research and medicine.

In one embodiment, the invention provides a genetically modified or chimeric rat cell whose genome comprises two chromosomal alleles of a SCID gene (especially, the Ada gene), wherein at least one of the two alleles contains a mutation, or the progeny of this cell. The invention includes the embodiment of the above animal cell, wherein one of the alleles expresses a normal SCID gene product. The invention includes the embodiment wherein the rat cell is a pluripotent cell such as an embryonic cell, embryonic stem (ES) cell, induced pluripotent stem cell (iPS), or spermatogonial stem (SS) cell, and in particular, wherein the SCID gene is the gene. In another embodiment, the SCID gene is one of several known SCID genes, such as (Rag1, Rag2, Dclre1c, Nhej1, Jak3, Il7r, Ptprc, Cd3d, Cd3e, Il2rg, Prkdc, Sirpa, Foxn1). In another embodiment, the rat cell is a somatic cell.

The methods of the present invention can be used to mutate any eukaryotic cell, including, but not limited to, haploid (in the case of multiple gene mutations), diploid, triploid, tetraploid, or aneuploid. In one embodiment, the cell is diploid. Cells in which the methods of the present invention can be advantageously used include, but are not limited to, primary cells (e.g., cells that have been explanted directly from a donor organism) or secondary cells (e.g., primary cells that have been grown and that have divided for some period of time in vitro, e.g., for 10-100 generations). Such primary or secondary cells can be derived from multi-cellular organisms, or single-celled organisms. The cells used in accordance with the invention include normal cells, terminally differentiated cells, or immortalized cells (including cell lines, which can be normal, established or transformed), and can be differentiated (e.g., somatic cells or germ cells) or undifferentiated (e.g., multipotent, pluripotent or totipotent stem cells).

A variety of cells isolated from the above-referenced tissues, or obtained from other sources (e.g., commercial sources or cell banks), can be used in accordance with the invention. Non-limiting examples of such cells include somatic cells, such as, blood cells (erythrocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, thymic nurse cells, Schwann cells, etc.). Eukaryotic germ cells (spermatocytes and oocytes) can also be used in accordance with the invention, as can the progenitors, precursors and stem cells that give rise to the above-described somatic and germ cells. These cells, tissues and organs can be normal, or they can be pathological such as those involved in diseases or physical disorders, including but not limited to immune related diseases (Severe Combined Immunodeficiency (SCID): autosomal recessive, with sensitivity to ionizing radiation, microchephaly, growth retardation, X-linked, Bare Lymphocyte syndrome) infectious diseases (caused by bacteria, fungi or yeast, viruses (including HIV) or parasites), in genetic or biochemical pathologies (e.g., cystic fibrosis, hemophilia, Alzheimer's disease, schizophrenia, muscular dystrophy, multiple sclerosis, etc.), or in carcinogenesis and other cancer-related processes. Rat pluripotent cells, including embryonic cells, spermatogonial stem cells, embryonic stem cells, and iPS cells are envisioned. Rat somatic cells are also envisioned.

In certain embodiments of the invention, cells can be mutated within the organism or within the native environment as in tissue explants (e.g., in vivo or in situ). Alternatively, tissues or cells isolated from the organism using art-known methods and genes can be mutated according to the present methods. The tissues or cells are either maintained in culture (e.g., in vitro), or re-implanted into a tissue or organism (e.g., ex vivo).

The invention also includes a non-human genetically modified or chimeric rat whose genome comprises two chromosomal alleles of a Severe Combined Immunodeficiency (SCID) gene, wherein at least one of the two alleles contains a mutation, or the progeny of the animal, or an ancestor of the animal, at an embryonic stage (preferably the one-cell, or fertilized oocyte stage, and generally, not later than about the 8-cell stage) contains a mutation. The invention also includes the embodiment wherein the SCID gene of the rat is the Ada gene. In another embodiment, the SCID gene is one of several known SCID genes, such as (Rag1, Rag2, Dclre1c, Nhej1, Jak3, Il7r, Ptprc, Cd3d, Cd3e, Il2rg, Prkdc Sirpa, Foxn1). The invention is also directed to the embodiment wherein the animal cell is a rat pluripotent cell. The invention is also directed to the embodiment wherein the animal cell is a rat somatic cell.

Figure 2:
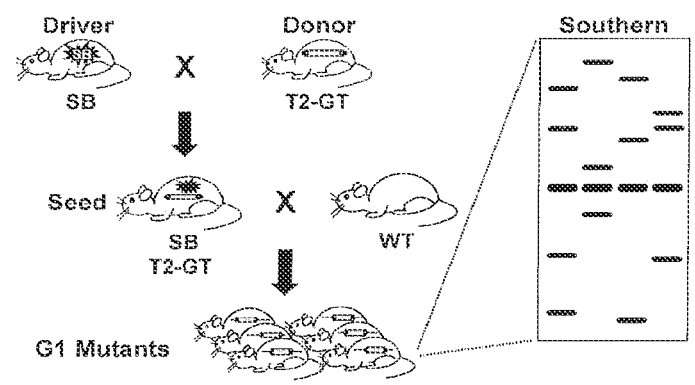

In one embodiment, the SCID gene is mutated directly in the germ cells of a living organism. The separate transgenes for DNA transposon flanking ends and transposase are facilitated to create an active DNA transposon which integrates into the rat's genome. A plasmid containing tranposon inverted repeats is used to create the transgenic "donor" rat. A plasmid containing transposase is used to create a separate transgenic "driver" rat. The donor rat is then bred with the driver rat to produce a rat which contains both donor transposon with flanking repeats and driver transposase (FIG. 2). This rat known as the "seed" rat has an activated DNA transposase which drives transposition events. The seed rat is bred to wild type rats to create heterozygote progeny with new transposon insertions. The heterozygotes can be interbred to create homozygous rats. Transposon insertion mutations are identified and recovered via a cloning and sequencing strategy involving the transposon-cellular DNA junction fragments. The rats that are identified to have a new DNA transposon insertion in a known gene or EST or DNA sequence of interest are called knockout rats.

In one embodiment, the SCID gene is mutated in the oocyte before fusion of the pronuclei. This method for genetic modification of rats uses microinjected DNA into the male pronucleus before nuclear fusion. The microinjected DNA creates a genetically modified founder rat. A female rat is mated and the fertilized eggs are flushed from their oviducts. After entry of the sperm into the egg, the male and female pronuclei are separate entities until nuclear fusion occurs. The male pronucleus is larger are can be identified via dissecting microscope. The egg can be held in place by micromanipulation using a holding pipette. The male pronucleus is then microinjected with DNA that can be genetically modified. The microinjected eggs are then implanted into a surrogate pseudopregnant female which was mated with a vasectomized male for uterus preparation. The foster mother gives birth to genetically modified animal. The microinjection method can introduce genetic modifications directly to the germline of a living animal.

In another embodiment, the SCID gene is mutated in a pluripotent cell. These pluripotent cells can proliferate in cell culture and be genetically modified without affecting their ability to differentiate into other cell types including germline cells. Genetically modified pluripotent cells from a donor can be microinjected into a recipient blastocyst, or in the case of spermatogonial stem cells can be injected into the rete testis of a recipient animal. Recipient genetically modified blastocysts are implated into pseudopregnant surrogate females. The progeny which have a genetic modification to the germline can then be established, and lines homozygous for the genetic modification can be produced by interbreeding.

In another embodiment, the SCID gene is mutated in a somatic cell and then used to create a genetically modified animal by somatic cell nuclear transfer. Somatic cell nuclear transfer uses embryonic, fetal, or adult donor cells which are isolated, cultured, and/or modified to establish a cell line. Individual donor cells are fused to an enucleated oocyte. The fused cells are cultured to blastocyst stage, and then transplanted into the uterus of a pseudopregnant female.

In one embodiment, the present invention is directed to methods for mutating a single gene or multiple genes (e.g., two or more) in eukaryotic cells and multicellular organisms. The present invention contemplates several methods for creating mutations in the SCID gene(s). In one embodiment the mutation is an insertion mutation. In another embodiment the mutation is a deletion mutation. In another embodiment the method of mutation is the introduction of a cassette or gene trap by recombination. In another embodiment a small nucleic acid sequence change is created by mutagenesis (through the creation of frame shifts, stop mutations, substitution mutations, small insertion mutations, small deletion mutations, and the like). In yet another embodiment, a transgene is delivered to knockout or knockdown the products of the SCID gene (mRNA or protein) in trans.

The invention also is directed to insertional mutagens for making the mutant cells and organisms, and which also can be used to analyze the mutations that are made in the cells and organisms. The invention also is directed to methods in which one or more mutated genes is tagged by a tag provided by the insertional mutagen to allow the detection, selection, isolation, and manipulation of a cell with a genome tagged by the insertional mutagen and allows the identification and isolation of the mutated gene(s). The invention provides methods for making multiple mutations (i.e., mutations in two or more genes that produce a phenotype cumulatively) in cells and organisms and tagging at least one of the mutated genes such that the mutation can be rapidly identified.

The term gene disruption as used herein refers to a gene knock-out or knock-down in which an insertional mutagen is integrated into an endogenous gene thereby resulting expression of a fusion transcript between endogenous exons and sequences in the insertional mutagen.

In one embodiment, the invention provides for insertional mutagenesis involving the integration of one or more polynucleotide sequences into the genome of a cell or organism to mutate one or more endogenous genes in the cell or organism. Thus, the insertional mutagenic polynucleotides of the present invention are designed to mutate one or more endogenous genes when the polynucleotides integrate into the genome of the cell.

Accordingly, the insertional mutagens used in the present invention can comprise any nucleotide sequence capable of altering gene expression levels or activity of a gene product upon insertion into DNA that contains the gene. The insertional mutagens can be any polynucleotide, including DNA and RNA, or hybrids of DNA and RNA, and can be single-stranded or double-stranded, naturally occurring or non-naturally occurring (e.g., phosphorothioate, peptide-nucleic acids, etc.). The insertional mutagens can be of any geometry, including but not limited to linear, circular, coiled, supercoiled, branched, hairpin, and the like, and can be any length capable of facilitating mutation, and tagging of an endogenous gene. In certain embodiments, the insertional mutagens can comprise one or more nucleotide sequences that provide a desired function.

In another embodiment, the method further involves transforming a cell with a nucleic acid construct comprising donor DNA. An example of donor DNA may include a DNA transposon. Transposable elements are discrete sequences in the genome which are mobile. They have the ability to translocate from one position in the genome to another. Unlike most genetic entities that can create modification to an organism's genome, transposons do not require homology with the recipient genome for insertion. Transposons contain inverted terminal repeats which are recognized by the protein transposase. Transposase facilitates the transposition event. Transposition can occur in replicative (the element is duplicated) or nonreplicative (element moves from one site to another and is conserved) mechanism. Transposons can either contain their own transposase or transposase can be added in trans to facilitate transposition. The transposon promotes genetic modifications in many ways. The insertion itself may cause genetic modification by disruption of a DNA sequence or introduction of DNA. The transposon may be used to deliver a gene trap.

In another embodiment, the method for mutagenesis involves transforming a cell with nucleic acid by use of a LTR retrotransposon with reverse transcriptase. The retrotransposon is initially composed of a single strand of RNA. This single stranded RNA is converted into a double stranded DNA by reverse transcriptase. This is a linear duplex of DNA that is integrated into the host's genome by the enzyme integrase. This insertion event is much like a transposition event and can be engineered to genetically modify a host's genome.

In another embodiment, the method for mutageneis is a non-LTR retrotransposon. Long Interspersed Nucleotide Elements (LINEs) are retrotransposons that do not have long terminal repeats (LTR's). The LINES open reading frame 1 (ORF1) is a DNA binding protein, ORF2 provides both reverse transcriptase and endonuclease activity. The endonucleolytic nick provides the 3'-OH end required for priming the synthesis of cDNA on the RNA template by reverse transcriptase. A second cleavage site opens the other strand of DNA. The RNA/DNA hybrid integrates into the host genome before or after converting into double stranded DNA. The integration process is called target primed reverse transcription (TPRT).

In another embodiment a retrovirus may be used for insertional genetic modification. The retroviral vector (e.g., lentivirus) inserts itself into the genome. The vector can carry a transgene or can be used for insertional mutagenesis. The infected embryos are then injected into a receptive female. The female gives birth to founder animals which have genetic modifications in their germline. Genetically modified lines are established with these founder animals.

In another embodiment, mutagenesis by recombination of a cassette into the genome may be facilitated by targeting constructs or homologous recombination vectors. Homologous recombination vectors are composed of fragments of DNA which are homologous to target DNA. Recombination between identical sequences in the vector and chromosomal DNA will result in genetic modification. The vector may also contain a selection method (e.g., antibiotic resistance or GFP) and a unique restriction enzyme site used for further genetic modification. The targeting vector will insert into the genome at a position (e.g, exon, intron, regulatory element) and create genetic modification.

In another embodiment, mutagenesis through recombination of a cassette into the genome may be carried out by Serine and Tyrosine recombinase with the addition of an insertion cassette. Site-specific recombination occurs by recombinase protein recognition of DNA, cleavage and rejoining as a phosphodiesterase bond between the serine or tyrosine residues. A cassette of exogenous or endogenous DNA may be recombined into the serine or tyrosine site. The cassette can contain a transgene, gene trap, reporter gene or other exogenous or endogenous DNA.

In one embodiment, the present invention is directed to methods for both targeted (site-specific) DNA insertions and targeted DNA deletions. In one embodiment, the method involves transformation of a cell with a nucleic acid or mRNA construct minimally comprising DNA encoding a chimeric zinc finger nuclease (ZFN), which can be used to create a DNA deletion. In another embodiment, a second DNA construct can be provided that will serve as a template for repair of the cleavage site by homologous recombination. In this embodiment, a DNA insertion may be created. The DNA insertion may contain a gene trap cassette.

The invention also is directed to nucleic acid sequence mutation for making the mutant cells and organisms.

In one embodiment, the method involves chemical mutagenesis with mutagens such as methane-sulfonic acid ethylester (EMS), N-ethyl-N-nitrosourea (ENU), diepoxyoctane and UV/trimethylpsorlalen to create nucleic acid sequence mutations.

In another embodiment, sequence editing methods are used that involve the delivery of small DNA fragments, hybrid DNA/RNA molecules, and modified DNA polymers to create sequence mismatches and nucleic acid mutations. RNA/DNA hybrids are molecules composed of a central stretch of DNA flanked by short RNA sequences that form hairpin structures. The RNA/DNA hybrids can produce single base-pair substitutions and deletions resulting in nucleotide mutations. Some other sequence editing examples include triplex forming oligonucliotides, small fragment homologous replacement, single-stranded DNA oligonucleotides, and adeno-associated virus (AAV) vectors.

The invention also is directed to genetic expression modification or mutagenesis, which may be carried out by delivery of a transgene that works in trans.

In one embodiment, RNA interference (RNAi) may be used to alter the expression of a gene. Single stranded mRNA can be regulated by the presence of sections of double stranded RNA (dsRNA) or small interfering RNA (siRNA). Both anti-sense and sense RNAs can be effective in inhibiting gene expression. siRNA mediates RNA interference and is created by cleavage of long dsDNA by the enzyme Dicer. RNAi can create genetic modification by triggering the degradation of mRNA's that are complementary to either strand of short dsRNA. When siRNA is associated with complementary single-stranded RNA it can signal for nuclease to degrade the mRNA. RNAi can also result in RNA silencing which occurs when the short dsRNA inhibits expression of a gene. Other forms of inhibitory RNA, such as small hairpin RNA (shRNA) are envisioned.

In another embodiment, the delivery of a transgene encoding a dominant negative protein may alter the expression of a target gene. Dominant negative proteins can inhibit the activity of an endogenous protein. One example is the expression a protein which contains the ligand binding site of an endogenous protein. The expressed dominant-negative protein "soaks up" all of the available ligand. The endogenous protein is therefore not activated, and the wild type function is knocked out or knocked down.

Other schemes based on these general concepts are within the scope and spirit of the invention, and are readily apparent to those skilled in the art.

The invention also provides methods for making homozygous mutations in rats by breeding a genetically modified rat which is heterozygous for a mutant allele with another genetically modified rat which is heterozygous for the same mutant allele. On average 25% of offspring of such matings are expected to produce animals that are homozygous for the mutant allele. Homozygous mutations are useful for discovering functions associated with the mutated gene.

The present invention is directed generally to reduction or inactivation of gene function or gene expression in cells in vitro and in multicellular organisms. The invention encompasses methods for mutating cells using one or more mutagens, particularly wherein at least one mutation is an insertion mutation, a deletion mutation, or a nucleic acid sequence mutation, to achieve a homozygous gene mutation or mutation of multiple genes required cumulatively to achieve a phenotype. The methods are used to create knockouts, knock-downs, and other modifications in the same cell or organism.

The mutation can result in a change in the expression level of a gene or level of activity of a gene product. Activity encompasses all functions of a gene product, e.g., structural, enzymatic, catalytic, allosteric, and signaling. In one embodiment, mutation results in a decrease or elimination of gene expression levels (RNA and/or protein) or a decrease or elimination of gene product activity (RNA and/or protein). Most mutations will decrease the activity of mutated genes. However, both the insertional and physicochemical mutagens can also act to increase or to qualitatively change (e.g., altered substrate on binding specificity, or regulation of protein activity) the activity of the product of the mutated gene. Although mutations will often generate phenotypes that may be difficult to detect, most phenotypically detectable mutations change the level or activity of mutated genes in ways that are deleterious to the cell or organism.

As used herein, decrease means that a given gene has been mutated such that the level of gene expression or level of activity of a gene product in a cell or organism is reduced from that observed in the wild-type or non-mutated cell or organism. This is often accomplished by reducing the amount of mRNA produced from transcription of a gene, or by mutating the mRNA or protein produced from the gene such that the expression product is less abundant or less active.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a rat. Also disclosed are animals produced by the process of transfecting a cell within the animal any of the nucleic acid molecules disclosed herein, wherein the mammal is a rat.

Such methods are used to achieve mutation of a single gene to achieve a desired phenotype as well as mutation of multiple genes, required cumulatively to achieve a desired phenotype, in a rat cell or rat. The invention is also directed to methods of identifying one or more mutated genes, made by the methods of the invention, in rat cells and in rats, by means of a tagging property provided by the insertional mutagen(s). The insertional mutagen thus allows identification of one or more genes that are mutated by insertion of the insertional mutagen.

The invention is also directed to rat cells and rats created by the methods of the invention and uses of the rat cells and rats. The invention is also directed to libraries of rat cells created by the methods of the invention and uses of the libraries.

Severe Combined Immunodeficiency (SCID)-Associated Genes

The invention also features a novel genetically modified rat with a genetically engineered modification in a gene encoding a Severe Combined Immunodeficiency (SCID)-associated protein. In another aspect, the invention features a genetically modified rat, wherein a gene encoding SCID protein is modified resulting in reduced SCID protein activity. In preferred embodiments of this aspect, the genetically modified rat is homozygous for the modified gene. In other preferred embodiments, the gene encoding SCID protein is modified by disruption, and the genetically modified rat has reduced SCID protein activity. In yet another embodiment, the transgenic rat is heterozygous for the gene modification.

In another embodiment of this aspect of the invention, the invention features a nucleic acid vector comprising nucleic acid capable of undergoing homologous recombination with an endogenous SCID gene in a cell, wherein the homologous recombination results in a modification of the SCID gene resulting in decreased SCID protein activity in the cell. In another aspect, the modification of the SCID gene is a disruption in the coding sequence of the endogenous SCID gene.

Another embodiment of this aspect of the invention features a rat cell, wherein the endogenous gene encoding SCID protein is modified, resulting in reduced SCID protein activity in the cell.

In certain embodiments, the reduced SCID protein activity is manifested. In a related aspect, the invention features a rat cell containing an endogenous SCID gene into which there is integrated a transposon comprising DNA encoding a gene trap and/or a selectable marker.

In another aspect, the invention features a rat cell containing an endogenous SCID gene into which there is integrated a retrotransposon comprising DNA encoding a gene trap and/or a selectable marker. In another aspect, the invention features a rat cell containing an endogenous SCID gene into which there is DNA comprising an insertion mutation in the SCID gene. In another aspect, the invention features a rat cell containing an endogenous SCID gene into which there is DNA comprising a deletion mutation in the SCID gene. In another aspect, the invention features a rat cell containing an endogenous SCID gene in which there has been nucleic acid sequence modification of the SCID gene.

In another embodiment of the invention, the invention features a method for determining whether a compound is potentially useful for treating or alleviating the symptoms of a SCID gene disorder, which includes (a) providing a cell that produces a SCID protein, (b) contacting the cell with the compound, and (c) monitoring the activity of the SCID protein, such that a change in activity in response to the compound indicates that the compound is potentially useful for treating or alleviating the symptoms of a SCID gene disorder.

It is understood that simultaneous targeting of more than one gene may be utilized for the development of "knock-out rats" (i.e., rats lacking the expression of a targeted gene product), "knock-in rats" (i.e., rats expressing a fusion protein or a protein encoded by a gene exogenous to the targeted locus), "knock down rats" (i.e., rats with a reduced expression of a targeted gene product), or rats with a targeted gene such that a truncated gene product is expressed.

Rat models that have been genetically modified to alter SCID gene expression may be used in in vivo assays to test for activity of a candidate SCID modulating agent, or to further assess the role of SCID gene in a (SCID pathway process such as V(D)J recombination or Natural Killer (NK) cell activity. Preferably, the altered SCID gene expression results in a detectable phenotype, such as decreased levels of T-, B-, and Natural Killer (NK)-cells, non-homologous end joining (NHEJ) function, or and increase in susceptibility to infections compared to control animals having normal SCID gene expression. The genetically modified rat may additionally have altered SCID gene expression (e.g., SCID gene knockout). In one embodiment, the genetically modified rats are genetically modified animals having a heterologous nucleic acid sequence present as an extrachromosomal element in a portion of its cells, i.e. mosaic animals (see, for example, techniques described by Jakobovits, 1994, Curr. Biol. 4:761-763) or stably integrated into its germ line DNA (i.e., in the genomic sequence of most or all of its cells). Heterologous nucleic acid is introduced into the germ line of such genetically modified animals by genetic manipulation of, for example, embryos or germ cells or germ cells precursors of the host animal.

Methods of making genetically modified rodents are well-known in the art (see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for genetically modified *Drosophila* see Rubin and Spradling, Science (1982) 218: 348-53 and U.S. Pat. No. 4,670,388; for genetically modified insects see Berghammer A. J. et al., A Universal Marker for Genetically modified Insects (1999) Nature 402:370-371; for genetically modified Zebrafish see Lin S., Genetically modified Zebrafish, Methods Mol Biol. (2000); 136: 375-3830); for microinjection procedures for fish, amphibian eggs and birds see Houdebine and Chourrout, Experientia (1991) 47:897-905; Hammer et al., Cell (1990) 63:1099-1112; and for culturing of embryonic stem (ES) cells and the subsequent production of genetically modified animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman genetically modified animals can be produced according to available methods (see Wilmut, I. et al. (1997) Nature 385:810-813; and PCT International Publication Nos. WO 97/07668 and WO 97/07669).

In one embodiment, the genetically modified rat is a "knock-out" animal having a heterozygous or homozygous alteration in the sequence of an endogenous SCID gene that results in a decrease of immune function, preferably such that SCID gene expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the genetically modified host species. For example, a mouse SCID gene is used to construct a homologous recombination vector suitable for altering an endogenous SCID gene in the mouse genome. Detailed methodologies for homologous recombination in rodents are available (see Capecchi, Science (1989) 244:1288-1292; Joyner et al., Nature (1989) 338:153-156). Procedures for the production of non-rodent genetically modified mammals and other animals are also available (Houdebine and Chourrout, supra; Pursel et al., Science (1989) 244:1281-1288; Simms et al., Bio/Technology (1988) 6:179-183). In a preferred embodiment, knockout animals, such as rats harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270:8397-400).

In another embodiment, the genetically modified rat is a "knock-down" animal having an alteration in its genome that results in altered expression (e.g., decreased expression) of the SCID gene, e.g., by introduction of mutations to the SCID gene, or by operatively inserting a regulatory sequence that provides for altered expression of an endogenous copy of the SCID gene.

Genetically modified rats can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" genetically modified animals, e.g., by mating two genetically modified animals, one containing a transgene encoding a selected protein and the other containing a transgene encoding a recombinase. Another example of a recombinase system is the FLP recombinase system of *Saccharomyces cerevisiae* (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified rats can be used in genetic studies to further elucidate the immune function pathways, as animal models of disease and disorders implicating defective immune function, and for in vivo testing of candidate therapeutic agents, such as those identified in screens described below. The candidate therapeutic agents are administered to a genetically modified animal having altered immune system and phenotypic changes are compared with appropriate control animals such as genetically modified animals that receive placebo treatment, and/or animals with unaltered immune systems that receive candidate therapeutic agent.

The invention also features novel genetically modified animals with a genetically engineered modification in the gene encoding SCID proteins. In one aspect, the invention features a genetically modified non-human mammal, wherein a gene encoding SCID gene is provided as follows:

T-cell(–), B-cell (–), natural killer (NK)-cell (–) SCID: Ada

The Ada gene encodes the enzyme Adenosine deaminase which catalyzes the hydrolysis of adenosine and deoxyadenosine to inosine in the purine catabolic pathway. Defects in Ada lead to SCID in which the B-, T-, and NK-cells are depleted. In humans, ADA deficiency accounts for 15% of all SCID, 30% autosomal recessive SCID, and 50% of non-X-linked SCID. There are multiple forms of SCID; early-, delayed-, and late-onset. Early-onset being the most common and with symptoms occurring immediately after birth. Delayed-onset constitutes 10-15% of SCID due to ADA deficiency and symptoms occur between 6-24 months after birth. Late-onset symptoms occur between 4 years of age and into adulthood. Partial SCID occurs when an individual has decreased ADA activity in erythrocytes, but posses up to 80% of the normal number of leukocytes. Common SCID symptoms include recurrent respiratory and other organ infections resulting in severe inflammation and insufficiency leading ultimately to death.

By the methods of cell hybridization, Southern blot, gene dosage, and high-resolution in situ hybridization, the rat Ada locus was mapped to position 3q42. In Ada deficient cells, immature thymocytes undergo apoptosis. Adenosine deaminase catalyzes the hydrolysis of adenosine and deoxyadenosine triphosphate (dATP) to inosine. The accumulation of dATP and adenosine inhibits ribonucleotide reductase's ability to reduce purine and pyrimidine ribonucleotides, which is a step required for DNA synthesis. The accumulation of dATP and adenosine also inhibits S-adenosylhomocysteine hydrolase, which is required for cell viability. Both consequences of Ada deficiency are lymphotoxic and result in decreased or absent T-, B-, and NK cells. However, it has been shown that inhibition of adenosine kinase provides T-cell recovery, and that a phosphorylated ADA substrate is the cause of lymphotoxicity. It has also been suggested that dATP accumulation induces cytochrome c release from the mitochondria and initiates apoptosis of thymocytes.

T-cell (–), B-cell (–), NK-cell (+) SCID: Rag1 & Rag2

Recombination activating genes 1 & 2 (Rag1 &Rag2) play an essential role in the activation of immunoglobin V(D)J recombination to create variable immunoglobins and T-cell receptors. The proteins encoded by the genes work by creating nicks in DNA at conserved recombination signal sequences (RSS). The nicks create double-stranded breaks that then form a covalently sealed hairpin intermediate and recombination through signal joint formation commences. The recombination activating genes are essential for immunoglobin and T-cell receptor assembly from developing lymphocytes. It has been shown that RAG1 specific amino acid changes lead to competent DNA cleavage, but result in defective in signal joint formation. Rag1 interacts directly with DNA. RAG2 contains genetic elements on its 5-prime end which coordinate expression of Rag1 & Rag2. RAG2 plays an essential role in recognition and cleavage of distorted DNA intermediates and is critical in the joining step in V(D)J recombination. RAG2 also interacts with histone H3K4me3 which plays an important role in V(D)J recombination. Mutations to the active site of RAG2 and H3K4me3 impair V(D)J recombination. The recombination activating proteins have a special non-homologous end joining (NHEJ) function. In NHEJ–/– deficient cells, RAG1 & RAG2 interfaces with NHEJ factors to maintain NHEJ function and integrity.

In humans, 20-30% of all SCID cases are T-cell (–), B-cell (–), NK-cell (+), and within this group 50% have mutations to RAG1 or RAG2. Typically patients are admitted to the hospital before 100 days of life. SCID patients undergo recurrent diarrhea, fever, candidiasis, lung infections and other infections. If not treated by stem cell therapy or gene therapy the SCID is always fatal. Disruption of RAG1 & RAG2 V(D)J recombination function leads to the arrest of T- and B-cell development and immune system failure.

Omenn Syndrome

Omenn Syndrome is a less severe immune deficiency than SCID, characterized by autoimmune responses resulting in hepatomegaly, and splenomegaly. Some other features are reticuloendotheliosis, skin disorders, diarrhea, and often terminal leukemia. In several Omenn syndrome cases the RAG2 recognition site for Histone H3K4me3 is mutated. In Omenn patients, the autoimmune regulator AIRE is down-regulated, and no insulin self-antigen, or cytochrome p450 1A2 exist.

T-cell (−), B-cell (−), NK-cell (−) with sensitivity to ionizing radiation SCID: Dclre1c & Prkdc RT-PCR and BAC contig analysis mapped the Dclre1c gene which encodes the protein Artemis to locus 17q12.3 in rat. Dclre1c activity is critical for V(D)J recombination and DNA repair. Artemis has 5'- to 3' exonuclease activity alone, but also acquires 5'- to 3' endonuclease activity when in complex and phosphorylated by Prkdc. The complex formed between these two proteins is critical for the hairpin opening step of V(D)J recombination, and plays a role in NHEJ.

Mutations to the Dclre1c gene results in Athabaskan-type SCID (SCIDA) and partial SCID. SCIDA exhibits sensitivity to ionizing radiation. This sensitivity is due to the lack of DNA repair machinery activity. The symptoms are similar to other SCID phenotypes with continuous infections, diarrhea, fever, lymphopenia. However, in partial SCID low levels of polyclonal T- and B-cells are found. Partial SCID was found to be the result of a hypomorphic mutation to Artemis.

The Prkdc gene is a nuclear DNA-dependent serine/threonine protein kinase which must interact with autoimmune antigen Ku and be bound to DNA in order to exhibit it catalytic properties. The Prkdc gene was mapped by in situ hybridization to locus 11q23 in rats. Prkdc binds to DNA double strand breaks and other cleavages that occur after damage or during recombination intermediates. Prkdc−/− cells are hypersensitive to damage by ionizing radiation due to their inability to repair double strand breaks. In Prkdc−/− cells, V(D)J intermediates are unable to be processed and ligated. Therefore, B- and T-cells do not develop mature immunoglobulin and T-cell receptors.

T-cell (−), B-cell (−), NK-cell (+) with microcephaly, growth retardation, and sensitivity to ionizing radiation: Nhej1

The Nhej1 gene encodes a DNA repair factor Xlf which is structurally similar to Xrcc4. Nhej1 was mapped to the 9q33 locus in rats. Xlf interacts with Xrcc4 and Lig4 and is essential for the non-homologous end joining (NHEJ) pathway. Nhej1−/− defective cells and rats exhibit ionizing radiation sensitivity and the inability to undergo V(D)J recombination. Mutations to the Nhej1 gene result in B-, T-cell, and Cd45ro memory T-cell deficiency, but natural killer (NK) cell levels and activity remain normal. Disruption in the Nhej1 gene in humans leads to recurrent infections, hypogammaglobulinemia, and B- and T-cell lymphocytopenia.

T-cell (−), B-cell (+), NK-cell (−) SCID: Jak3& Il2rg

The Jak3 gene produces a tyrosine kinase that is involved in cytokine receptor-mediated intracellular signal transduction. In situ hybridization studies have been used to mapped the gene to locus 16p14 in rats. Interleukin2 gamma-c receptor (Il2gr) induces phosphorylation and activation of Jak3. Il2 gr and Jak3 operate through the same pathway and share this pathway with multiple cytokines. Il2 is a T-cell growth factor which is critical for the development of active T-cell lymphocytes. Mutations that decrease the association between Il2rg and Jak3 result in X-linked SCID. Inhibition of Jak3 or Il2rg disrupts the signal pathway and results in early and severe T-cell and NK-cell developmental blocking.

Humans that have a disruption in the JAK3 or IL3RG genes or the JAK3/IL2GR pathway have T-cell (−), B-cell (+), NK-cell (−) SCID. Patients have an absence of mature circulating T-lymphocytes and NK-cells, a normal level of nonfunctional B-cells, and hypoplasia in lymphoid tissues.

T-cell (−), B-cell (+), NK-cell (+), with decreased immunoglobulins: Il7r, Cd45, Cd3d, Cd3e The Il7r gene encodes Interleukin receptor7 which requires Il2rg for proper function. The Il7r gene was mapped to the 2q16 locus in rats using in situ hybridization and Southern blot analysis. Il7 interacts with Tslp to enhance dendritic cell (DC) monocyte maturation which induces T-cell proliferation. Memory T-cell lymphocytes that express high levels of Il7r also express high levels of anti-apoptotic markers. A disruption in the Il7r gene leads to increased apoptosis of T-cells. Il7−/− cells exhibit decreased V(H)–D(H)–J(H) joining.

The Ptprc gene or Cd45 encodes a protein that is involved in cell growth, differentiation, and mitotic cycle regulation. The gene was mapped to the 13q13 locus in rats. The Cd45 protein suppresses Jak kinases, and plays a role in cytokine signaling. The Cd45 protein is essential for activation of T-cells mediated by the cell-to-cell, receptor-antigen signal transduction pathway. Cd45−/− undergo a block of T-cell maturation.

The Cd3d gene was mapped to the locus 8q22 in rats. The Cd3d protein is essential for T-cell development and signal transduction. In Cd3d−/− cells immature thymocytes are negatively selected and removed before differentiation into mature thymocytes. T-cell differentiation is blocked at early stage entry.

Through somatic cell hybrids and in situ hybridization, the Cd3e gene was mapped to locus 8q22 in rats. The Cd3e gene encodes a protein that forms a T-cell receptor complex. The Cd3e protein is essential for T-cell antigen recognition and intracellular signaling transduction pathways.

Humans with deficient IL7R, CD45, CD3D, CD3E genes have T-cell (−), B-cell (+), NK-cell (+) SCID. Fever, rash, hepatosplenomegaly, lymphadenopathy, pneumonitis, pancytopenia, and cytomegalovirus infection are common symptoms among patients. Patients display a low T-cell count, decreased immunoglobulins, and abnormal CD45, CD3D, CD3E expression.

The invention also features novel genetically modified cells and animals with a genetically engineered modification in a gene encoding SCID proteins. In one aspect, the invention features genetically modified rat cells or rats, wherein a gene modification occurs in a gene encoding a SCID protein provided in Table 1:

TABLE 1

| SCID gene | Function | Rat Chromosomal Location |
|---|---|---|
| Ada NM_130399.2 | Hydrolysis of adenosine and deoxyadenosine triphosphate (dATP) to inosine | 3q42 |
| Rag1 NM_053468.1 | Immunoglobin V(D)J recombination | 3q31 |
| Rag2 NM_001100528.1 | Immunoglobin V(D)J recombination | 3q31 |

TABLE 1-continued

| SCID gene | Function | Rat Chromosomal Location |
|---|---|---|
| Dclre1c NM_147145.1 | V(D)J recombination and DNA repair | 17q12.3 |
| Prkdc NM_001108327.1 | binds to DNA double strand breaks and other cleavages that occur after damage or during recombination intermediates, and facilitates repair | 11q23 |
| Nhej1 NM_001014217.1 | non-homologous end joining (NHEJ) pathway | 9q33 |
| Jak3 NM_012855.1 | cytokine receptor mediated intracellular signal transduction | 16p14 |
| Il2rg NM_080889.1 | Il2 is a T-cell growth factor which is critical for the development of active T-cell lymphocytes, and induces phosphorylation and activation of Jak3 | Xq31 |
| Il7r NM_001106418.1 | enhances DC monocyte maturation which induces T-cell proliferation | 2q16 |
| Cd45 NM_138507.1 | cell growth, differentiation, and mitotic cycle regulation | 13q13 |
| Cd3d NM_013169.1 | T-cell development and signal transduction | 8q22 |
| Coro1a NM_130411.2 | Chemokine mediated migration, and lymphocyte development | 1q36 |
| Cd3e NM_0001108140.1 | T-cell antigen recognition and intracellular signaling transduction | 8q22 |
| Sirpa NM_013016.2 | Signal-regulatory protein alpha plays a role in macrophage fusion | 3q36 |
| Foxn1 NM_00110648.1 | Mutations are associated with congenital athymia and hairlessness | 10q25 |

Methods

The methods used in the present invention are comprised of a combination of genetic introduction methods, genetic modification or mutagenesis mechanisms, and vector delivery methods. For all genetic modification or mutagenesis mechanisms one or more introduction and delivery method may be employed. The invention may include but is not limited to the methods described below.

Genetic Introduction Methods

In one introduction method, the SCID gene is mutated directly in the germ cells of an adult animal. This method usually involves the creation of a transgenic founder animal by pronuclear injection. Rat oocytes are microinjected with DNA into the male pronucleus before nuclear fusion. The microinjected DNA creates a transgenic founder rat. In this method, a female rat is mated and the fertilized eggs are flushed from their oviducts. After entry of the sperm into the egg, the male and female pronuclei are separate entities until nuclear fusion occurs. The male pronucleus is larger are can be identified via dissecting microscope. The egg can be held in place by micromanipulation using a holding pipette. The male pronucleus is then microinjected with DNA that can be genetically modified. The microinjected eggs are then implanted into a surrogate pseudopregnant female which was mated with a vasectomized male for uterus preparation. The foster mother gives birth to transgenic founder animals. If the transgenic DNA encodes the appropriate components of a mutagenesis system, such as transposase and a DNA transposon, then mutagenesis will occur directly in the germ cells of founder animals and some offspring will contain new mutations. Chemical mutagenesis can also be used to cause direct germ line mutations.

In another introduction method, the SCID gene is mutated in the early embryo of a developing animal. The mutant embryonic cells develop to constitute the germ cells of the organism, thereby creating a stable and heritable mutation. Several forms of mutageneis mechanisms can be introduced this way including, but not limited to, zinc finger nucleases and delivery of gene traps by a retrovirus.

In another introduction method, the SCID gene is mutated in a pluripotent cell. These pluripotent cells can proliferate in cell culture and be genetically modified without affecting their ability to differentiate into other cell types including germ line cells. Genetically modified pluripotent cells from a donor can be microinjected into a recipient blastocyst, or in the case of spermatogonial stem cells can be injected into the rete testis of a recipient animal. Recipient genetically modified blastocysts are implanted into pseudopregnant surrogate females. The progeny which have a genetic modification to the germ line can then be established, and lines homozygous for the genetic modification can be produced by interbreeding.

In another introduction method, the SCID gene is mutated in a somatic cell and then used to create a genetically modified animal by somatic cell nuclear transfer. Somatic cell nuclear transfer uses embryonic, fetal, or adult donor cells which are isolated, cultured, and/or modified to establish a cell line. Individual donor cells are fused to an enucleated oocyte. The fused cells are cultured to blastocyst stage, and then transplanted into the uterus of a pseudopregnant female. Alternatively the nucleus of the donor cell can be injected directly into the enucleated oocyte. See U.S. Appl. Publ. No. 20070209083.

Genetic Modification Methods

Mobile DNA Technology

DNA transposons are discrete mobile DNA segments that are common constituents of plasmid, virus, and bacterial chromosomes. These elements are detected by their ability to transpose self-encoded phenotypic traits from one replicon to another, or to transpose into a known gene and inactivate it. Transposons, or transposable elements, include a piece of nucleic acid bounded by repeat sequences. Active transposons encode enzymes (transposases) that facilitate the insertion of the nucleic acid into DNA sequences.

The lifecycle and insertional mutagenesis of DNA transposon Sleeping Beauty (SB) is depicted in FIG. 1. In its lifecycle, the SB encodes a transposase protein. That transposase recognizes the inverted terminal repeats (ITRs) that flank the SB transposon. The transposase then excises SB and reintegrates it into another region of the genome. Mutagenesis via Sleeping Beauty is depicted. The mechanism is similar to the life cycle, but transposase is not encoded by the transposon, but instead is encoded elsewhere in the genome The Sleeping Beauty (SB) mutagenesis breeding and screening scheme is depicted in FIG. 2. One rat referred to as the "driver" rat contains the (SB) transposase within its genome. A second rat, the "donor" rat contains the transposon which has the transposase-recognizable inverted terminal repeats (ITRs). The two rats are bred to create the "seed" rat which has an active transposon containing transposase and ITRs. The transposon recognizes the ITRs, excises the transposon, and inserts it elsewhere in the rat's genome. This insertion event often disrupts coding, regulatory, and other functional regions in the genome to create knockout rat models. The "seed" rat is bred with wild type rats which beget heterozygous G1 mutants. If the transposon has inserted into the genome, the event will be recorded via size comparison of DNA by Southern blot analysis. The exact location of the transposon insertion is determined by PCR-based amplification methods combined with sequencing of the DNA flanking the new insertion.

The sequences for the DNA transposons Sleeping Beauty (SB) piggyBac (PB) functional domains are shown in FIG. 3. The SB and PB transposase sequences encode the protein that recognizes the ITRs and carries out the excision and re-integration. The 3' and 5' ITRs are the flanking sequences which the respective transposases recognizes in order to carry out excision and reintegration elsewhere in the genome.

Figure 4:
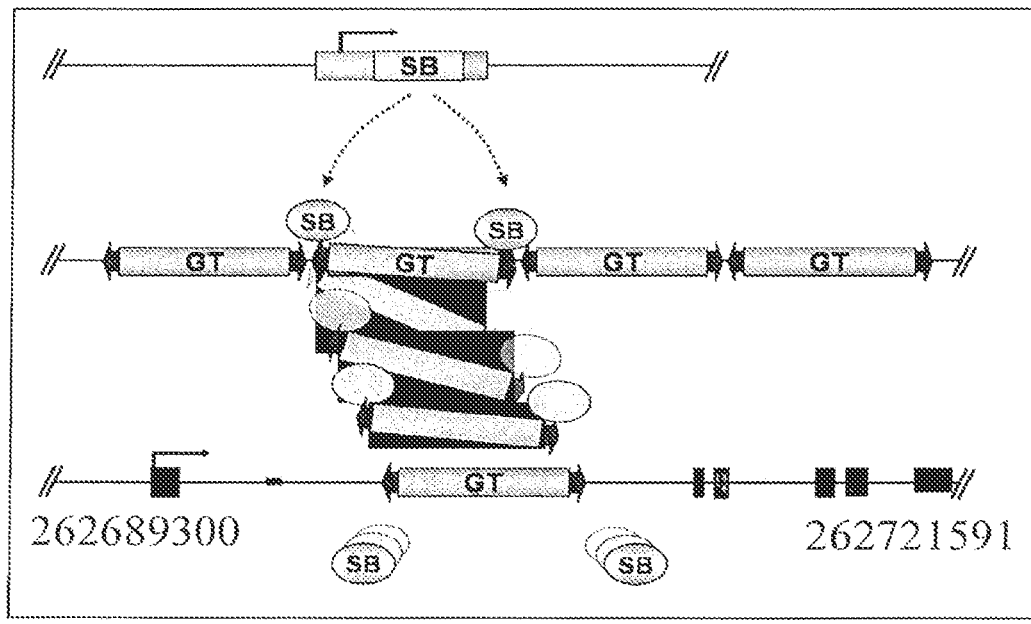

The DNA transposon Sleeping Beauty (SB) was used by the inventors to create a knockout rat in the Ada gene. The mechanism is depicted in FIG. 4, and is the same as that described above. The transposase is encoded, and the protein recognizes the ITRs of the transposon. The transposon is then excised and reinserted into the seventh intron of the rat Ada gene which resides on chromosome 3, location 3q42.

In another embodiment, the present invention utilizes the transposon piggyBac, and sequence configurations outside of piggyBac, for use as a mobile genetic element as described in U.S. Pat. No. 6,962,810. The Lepidopteran transposon piggyBac is capable of moving within the genomes of a wide variety of species, and is gaining prominence as a useful gene transduction vector. The transposon structure includes a complex repeat configuration consisting of an internal repeat (IR), a spacer, and a terminal repeat (TR) at both ends, and a single open reading frame encoding a transposase.

The Lepidopteran transposable element piggyBac transposes via a unique cut-and-paste mechanism, inserting exclusively at 5' TTAA 3' target sites that are duplicated upon insertion, and excising precisely, leaving no footprint (Elick et al., 1996b; Fraser et al., 1996; Wang and Fraser 1993).

In another embodiment, the present invention utilizes the Sleeping Beauty transposon system for genome manipulation as described, for example, in U.S. Pat. No. 7,148,203. In one embodiment, the system utilizes synthetic, salmonid-type Tc1-like transposases with recognition sites that facilitate transposition. The transposase binds to two binding-sites within the inverted repeats of salmonid elements, and appears to be substrate-specific, which could prevent cross-mobilization between closely related subfamilies of fish elements.

In another aspect of this invention, the invention relates to a transposon gene transfer system to introduce DNA into the DNA of a cell comprising: a nucleic acid fragment comprising a nucleic acid sequence positioned between at least two inverted repeats wherein the inverted repeats can bind to a SB protein and wherein the nucleic acid fragment is capable of integrating into DNA of a cell; and a transposase or nucleic acid encoding a transposase. In one embodiment, the transposase is provided to the cell as a protein and in another the transposase is provided to the cell as nucleic acid. In one embodiment the nucleic acid is RNA and in another the nucleic acid is DNA. In yet another embodiment, the nucleic acid encoding the transposase is integrated into the genome of the cell. The nucleic acid fragment can be part of a plasmid or a recombinant viral vector. Preferably, the nucleic acid sequence comprises at least a portion of an open reading frame and also preferably, the nucleic acid sequence comprises at least a regulatory region of a gene. In one embodiment the regulatory region is a transcriptional regulatory region and the regulatory region is selected from the group consisting of a promoter, an enhancer, a silencer, a locus-control region, and a border element. In another embodiment, the nucleic acid sequence comprises a promoter operably linked to at least a portion of an open reading frame.

In the transgene flanked by the terminal repeats, the terminal repeats can be derived from one or more known transposons. Examples of transposons include, but are not limited to the following: Sleeping Beauty (Izsvak Z, Ivics Z. and Plasterk R H. (2000) Sleeping Beauty, a wide host-range transposon vector for genetic transformation in vertebrates. J. Mol. Biol. 302:93-102), mos1 (Bessereau J L, et al. (2001) Mobilization of a *Drosophila* transposon in the *Caenorhabditis elegans* germ line. Nature. 413(6851):70-4; Zhang L, et al. (2001) DNA-binding activity and subunit interaction of the mariner transposase. Nucleic Acids Res. 29(17):3566-75, piggyBac (Tamura T. et al. Germ line transformation of the silkworm *Bombyx mori* L. using a piggyBac transposon-derived vector. Nat Biotechnol. 2000 January; 18(1):81-4), Himar1 (Lampe D J, et al. (1998) Factors affecting transposition of the Himar1 mariner transposon in vitro. Genetics. 149(11):179-87), Hermes, Tol2 element, Pokey, Tn5 (Bhasin A, et al. (2000) Characterization of a Tn5 pre-cleavage synaptic complex. J Mol Biol 302:49-63), Tn7 (Kuduvalli P N, Rao J E, Craig N L. (2001) Target DNA structure plays a critical role in Tn7 transposition. EMBO J 20:924-932), Tn916 (Marra D, Scott J R. (1999) Regulation of excision of the conjugative transposon Tn916. Mol Microbiol 2:609-621), Tc1/mariner (Izsvak Z, Ivics Z4 Hackett P B. (1995) Characterization of a Tc1-like transposable element in zebrafish (*Danio rerio*). Mol. Gen. Genet. 247:312-322), Minos and S elements (Franz G and Savakis C. (1991) Minos, a new transposable element from *Drosophila hydei*, is a member of the Tc1-like family of transposons. Nucl. Acids Res. 19:6646; Merriman P J, Grimes C D, Ambroziak J, Hackett D A, Skinner P, and Simmons M J. (1995) S elements: a family of Tel-like transposons in the genome of *Drosophila melanogaster*. Genetics 141:1425-1438), Quetzal elements (Ke Z, Grossman G L, Comel A J, Collins F H. (1996) Quetzal: a transposon of the Tc1 family in the mosquito *Anopheles albimanus*. Genetica 98:141-147); Txr elements (Lam W L, Seo P, Robison K, Virk S, and Gilbert W. (1996) Discovery of amphibian Tc1-like transposon families. J Mol Biol 257:359-366), Tc1-like transposon subfamilies (Ivics Z, Izsvak Z, Minter A, Hackett P B. (1996) Identification of functional domains and evolution of Tc1-like transposable elements. Proc. Natl. Acad Sci USA 93: 5008-5013), Tc3 (Tu Z. Shao H. (2002) Intra- and inter-specific diversity of Tc-3 like transposons in nematodes and insects and implications for their evolution and transposition. Gene 282:133-142), ICESt1 (Burrus Vet al. (2002) The ICESt1 element of *Streptococcus thermophilus* belongs to a large family of integrative and conjugative elements that exchange modules and change their specificity of integration. Plasmid. 48(2): 77-97), maT, and P-element (Rubin G M and Spradling A C. (1983) Vectors for P element-mediated gene transfer in *Drosophila*. Nucleic Acids Res. 11:6341-6351). These references are incorporated herein by reference in their entirety for their teaching of the sequences and uses of transposons and transposon ITRs.

Translocation of Sleeping Beauty (SB) transposon requires specific binding of SB transposase to inverted terminal repeats (ITRs) of about 230 bp at each end of the transposon, which is followed by a cut-and-paste transfer of the transposon into a target DNA sequence. The ITRs contain two imperfect direct repeats (DRs) of about 32 bp. The outer DRs are at the extreme ends of the transposon whereas the inner DRs are located inside the transposon, 165-166 bp from the outer DRs. Cui et al. (J. Mol Biol 318:1221-1235) investigated the roles of the DR elements in transposition. Within the 1286-bp element, the essential regions are contained in the intervals bounded by coordinates 229-586, 735-765, and 939-1066, numbering in base pairs from the extreme 5' end of the element. These regions may contain sequences that are necessary for transposase binding or that are needed to maintain proper spacing between binding sites.

Transposons are bracketed by terminal inverted repeats that contain binding sites for the transposase. Elements of the IR/R subgroup of the Tc1/mariner superfamily have a pair of transposase-binding sites at the ends of the 200-250 bp long inverted repeats (IRs) (Izsvak, et al. 1995). The binding sites contain short, 15-20 bp direct repeats (DRs). This characteristic structure can be found in several elements from evolutionarily distant species, such as Minos and S elements in flies (Franz and Savakis, 1991; Merriman et al, 1995), Quetzal elements in mosquitoes (Ke et al, 1996), Txr elements in frogs (Lam et al, 1996) and at least three Tc1-like transposon subfamilies in fish (Ivies et al., 1996), including SB [Sleeping Beauty] and are herein incorporated by reference.

Whereas Tc1 transposons require one binding site for their transposase in each IR, Sleeping Beauty requires two direct repeat (DR) binding sites within each IR, and is therefore classified with Tc3 in an IR/DR subgroup of the Tc1/mariner superfamily (96,97). Sleeping Beauty transposes into TA dinucleotide sites and leaves the Tc1/mariner characteristic footprint, i.e., duplication of the TA, upon excision. The non-viral plasmid vector contains the transgene that is flanked by IR/DR sequences, which act as the binding sites for the transposase. The catalytically active transposase may be expressed from a separate (trans) or same (cis) plasmid system. The transposase binds to the IR/DRs, catalyzes the excision of the flanked transgene, and mediates its integration into the target host genome.

Naturally occurring mobile genetic elements, known as retrotransposons, are also candidates for gene transfer vehicles. This mutagenesis method generally involves the delivery of a gene trap.

Retrotransposons are naturally occurring DNA elements which are found in cells from almost all species of animals, plants and bacteria which have been examined to date. They are capable of being expressed in cells, can be reverse transcribed into an extrachromosomal element and reintegrate into another site in the same genome from which they originated.

Retrotransposons may be grouped into two classes, the retrovirus-like LTR retrotransposons, and the non-LTR elements such as human L1 elements, *Neurospora* TAD elements (Kinsey, 1990, Genetics 126:317-326), I factors from *Drosophila* (Bucheton et al., 1984, Cell 38:153-163), and R2Bm from *Bombyx mori* (Luan et al., 1993, Cell 72: 595-605). These two types of retrotransposon are structurally different and also retrotranspose using radically different mechanisms.

Unlike the LTR retrotransposons, non-LTR elements (also called polyA elements) lack LTRs and instead end with polyA or A-rich sequences. The LTR retrotransposition mechanism is relatively well-understood; in contrast, the mechanism of retrotransposition by non-LTR retrotransposons has just begun to be elucidated (Luan and Eickbush, 1995, Mol. Cell. Biol. 15:3882-3891; Luan et al., 1993, Cell 72:595-605). Non-LTR retrotransposons can be subdivided into sequence-specific and non-sequence-specific types. L1 is of the latter type being found to be inserted in a scattered manner in all human, mouse and other mammalian chromosomes.

Some human L1 elements (also known as a LINES) can retrotranspose (express, cleave their target site, and reverse transcribe their own RNA using the cleaved target site as a primer) into new sites in the human genome, leading to genetic disorders.

Further included in the invention are DNAs which are useful for the generation of mutations in a cell. The mutations created are useful for assessing the frequency with which selected cells undergo insertional mutagenesis for the generation of genetically modified animals and the like. Engineered L1 elements can also be used as retrotransposon mutagens. Sequences can be introduced into the L1 that increases its mutagenic potential or facilitates the cloning of the interrupted gene. DNA sequences useful for this application of the invention include marker DNAs, such as GFP, that are specifically engineered to integrate into genomic DNA at sites which are near to the endogenous genes of the host organism. Other potentially useful DNAs for delivery are regulatory DNA elements, such as promoter sequences, enhancer sequences, retroviral LTR elements and repressors and silencers. In addition, genes which are developmentally regulated are useful in the invention.

Viral Mutagenesis Methods

Viral vectors are often created using a replication defective virus vector with a genome that is partially replaced by the genetic material of interest (e.g., gene trap, selectable marker, and/or a therapeutic gene). The viral vector is produced by using a helper virus to provide some of the viral components that were deleted in the replication defective virus, which results in an infectious recombinant virus whose genome encodes the genetic material of interest. Viral vectors can be used to introduce an insertion mutation into the rat's genome. Integration of the viral genetic material is often carried out by the viral enzyme integrase. Integrase brings the ends of viral DNA together and converts the blunt ends into recessed ends. Integrase creates staggered ends on chromosomal DNA. The recessed ends of the viral DNA are then joined with the overhangs of genomic DNA, and the singlestranded regions are repaired by cellular mechanisms. Some recombinant virus vectors are equipped with cell uptake, endosomal escape, nuclear import, and expression mechanisms allowing the genetic material of interest to be inserted and expressed in the rat's genome. The genetic material introduced via viral vectors can genetically modify the rat's genome but is not limited to disrupting a gene, inserting a gene to be expressed, and by delivery of interfering RNA. Viral vectors can be used in multiple methods of delivery. The most common mode of delivery is the microinjection of a replication deficient viral vector (e.g., retroviral, adenoviral) into an early embryo (1-4 day) or a onecell pronuclear egg. After viral vector delivery, the embryo is cultured in vitro and transferred to recipient rats to create genetically modified progeny.

In one embodiment, insertion mutations can be created by delivery of a gene trap vector into the rat genome. The gene trap vector consists of a cassette that contains selectable reporter tags. Upstream from this cassette is a 3' splice acceptor sequence. Downstream from the cassette lays a termination sequence poly adenine repeat tail (polyA). The splice accepter sequence allows the gene trap vector to be spliced into chromosomal mRNA. The polyA tail signals the premature interruption of the transcription. The result is a truncated mRNA molecule that has decreased function or is completely non-functional. The gene trap method can also be utilized to introduce exogenous DNA into the genome.

In another embodiment an enhancer trap is used for insertional mutagenesis. An enhancer trap is a transposable element vector that carries a weak minimal promoter which controls a reporter gene. When the transposable element is inserted the promoter drives expression of the reporter gene. The expression of the reporter gene also displays the expression patterns of endogenous genes. Enhancer trapping results in genetic modification and can be used for gain-of-function genetics. The Gal4-mediated expression system is an example of an enhancer trap.

Further included are one or more selectable marker genes. Examples of suitable prokaryotic marker genes include, but are not limited to, the ampicillin resistance gene, the kanamycin resistance gene, the gene encoding resistance to chloramphenicol, the lacZ gene and the like. Examples of suitable eukaryotic marker genes include, but are not limited to, the hygromycin resistance gene, the green fluorescent protein (GFP) gene, the neomycin resistance gene, the zeomycin gene, modified cell surface receptors, the extracellular portion of the IgG receptor, composite markers such as beta-geo (a lac/neo fusion) and the like.

In one embodiment, the gene trap will need to be integrated into the host genome and an integrating enzyme is needed. Integrating enzymes can be any enzyme with integrating capabilities. Such enzymes are well known in the art and can include but are not limited to transposases, integrases, recombinases, including but not limited to tyrosine site-specific recombinases and other site-specific recombinases (e.g., cre), bacteriophage integrases, retrotransposases, and retroviral integrases.

The integrating enzymes of the present invention can be any enzyme with integrating capabilities. Such enzymes are well known in the art and can include but are not limited to transposases (especially DDE transposases), integrases, tyrosine site-specific recombinases and other site-specific recombinases (e.g., cre), bacteriophage integrases, integrons, retrotransposases, retroviral integrases and terminases.

Disclosed are compositions, wherein the integrating enzyme is a transposase. It is understood and herein contemplated that the transposase of the composition is not limited and to any one transposase and can be selected from at least the group consisting of Sleeping Beauty (SB), Tn7, Tn5, mos1, piggyBac, Himar1, Hermes, Tol2, Pokey, Minos, S elements, P-elements, ICESt1, Quetzal elements, Tn916, maT, Tc1/mariner and Tc3.

Where the integrating enzyme is a transposase, it is understood that the transposase of the composition is not limited and to any one transposase and can be selected from at least the group consisting of Sleeping Beauty (SB), Tn7, Tn5, Tn916, Tc1/mariner, Minos and S elements, Quetzal elements, Txr elements, maT, mos1, piggyBac, Himar1, Hermes, Tol2, Pokey, P-elements, and Tc3. Additional transposases may be found throughout the art, for example, U.S. Pat. Nos. 6,225,121, 6,218,185 5,792,924 5,719,055, U.S. Patent Application No. 20020028513, and U.S. Patent Application No. 20020016975 and are herein incorporated by reference in their entirety. Since the applicable principal of the invention remains the same, the compositions of the invention can include transposases not yet identified.

Also disclosed are integrating enzymes of the disclosed compositions wherein the enzyme is an integrase. For example, the integrating enzyme can be a bacteriophage integrase. Such integrase can include any bacteriophage integrase and can include but is not limited to lamda bacteriophage and mu bacteriophage, as well as Hong Kong 022 (Cheng Q., et al. Specificity determinants for bacteriophage Hong Kong 022 integrase: analysis of mutants with relaxed core-binding specificities. (2000) Mol Microbiol. 36(2):424-36), HP1 (Hickman, A. B., et al. (1997). Molecular organization in site-specific recombination: The catalytic domain of bacteriophage HP1 integrase at 2.7 A resolution. Cell 89: 227-237), P4 (Shoemaker, N B, et al. (1996). The *Bacteroides mobilizable* insertion element, NBU1, integrates into the 3' end of a Leu-tRNA gene and has an integrase that is a member of the lambda integrase family. J Bacteriol. 178(12):3594-600), P1 (Li Y, and Austin S. (2002) The P1 plasmid in action: time-lapse photomicroscopy reveals some unexpected aspects of plasmid partition. Plasmid. 48(3):174-8), and T7 (Rezende, L. F., et al. (2002) Essential Amino Acid Residues in the Single-stranded DNA-binding Protein of Bacteriophage T7. Identification of the Dimer Interface. J. Biol. Chem. 277, 50643-50653). Integrase maintains its activity when fused to other proteins.

Also disclosed are integrating enzymes of the disclosed compositions wherein the enzyme is a recombinase. For example, the recombinase can be a Cre recombinase, Flp recombinase, HIN recombinase, or any other recombinase. Recombinases are well-known in the art. An extensive list of recombinases can be found in Nunes-Duby S E, et al. (1998) Nuc. Acids Res. 26(2): 391-406, which is incorporated herein in its entirety for its teachings on recombinases and their sequences.

Also disclosed are integrating enzymes of the disclosed compositions wherein the enzyme is a retrotransposase. For example, the retrotransposase can be a GATE retrotransposase (Kogan G L, et al. (2003) The GATE retrotransposon in *Drosophila melanogaster*: mobility in heterochromatin and aspects of its expression in germ line tissues. Mol Genet Genomics. 269(2):234-42).

Other general techniques for integration into the host genome include, for example, systems designed to promote homologous recombination. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

Zinc Finger Nucleases

In another method, a zinc finger nuclease creates site-specific deletions via double-stranded DNA breaks that are repaired by non-homologous end joining (NHEJ). Zinc finger nucleases may also be used to create an insertion mutation by combining the ZFN with a homologously integrating cassette to create an insertion in the genomic DNA. Therefore, this genetic modification method can be used for both targeted (site-specific) DNA insertions and targeted DNA deletions. In one embodiment, the method involves transformation of a cell with a nucleic acid or mRNA construct minimally comprising DNA encoding a chimeric zinc finger nuclease (ZFN), which can be used to create a DNA deletion. In another embodiment, a second DNA construct can be provided that will serve as a template for repair of the cleavage site by homologous recombination. In this embodiment, a DNA insertion may be created. The DNA insertion may contain a gene trap cassette. In one embodiment, this method can be combined with spermatogonial stem cell technology or embryonic stem cell technology, as mentioned above. In another embodiment, this method can be combined with mobile DNA technology. This technique can also be done directly in the rat embryo.

Nucleic Acid Modification Methods

In one embodiment, a random mutation is created with a chemical mutagen and then a screen is performed for insertions in a particular SCID gene. Chemical mutagens such as methane-sulfonic acid ethylester (EMS), N-ethyl-N-nitrosourea (ENU), diepoxyoctane and UV/trimethylpsorlalen may be employed to create nucleic acid sequence mutations.

Sequence editing methods can also be used that involve the delivery of small DNA fragments, hybrid DNA/RNA molecules, and modified DNA polymers to create sequence mismatches and nucleic acid mutations. RNA/DNA hybrids are molecules composed of a central stretch of DNA flanked by short RNA sequences that form hairpin structures. The RNA/DNA hybrids can produce single base-pair substitutions and deletions resulting in nucleotide mutations. Some other sequence editing examples include triplex forming oligonucleotides, small fragment homologous replacement, single stranded DNA oligonucleotides, and adeno-associated virus (AAV) vectors.

The invention also is directed to genetic expression modification or mutagenesis by delivery of a transgene that works in trans.

In one genetic modification method, RNA interference may be used to alter the expression of a gene. In another genetic modification method, the delivery of a transgene encoding a dominant negative protein may alter the expression of a target gene.

Vector Delivery Methods

The mutagenesis methods of this invention may be introduced into one or more cells using any of a variety of techniques known in the art such as, but not limited to, microinjection, combining the nucleic acid fragment with lipid vesicles, such as cationic lipid vesicles, particle bombardment, electroporation, DNA condensing reagents (e.g., calcium phosphate, polylysine or polyethyleneimine) or incorporating the nucleic acid fragment into a viral vector and contacting the viral vector with the cell. Where a viral vector is used, the viral vector can include any of a variety of viral vectors known in the art including viral vectors selected from the group consisting of a retroviral vector, an adenovirus vector or an adeno-associated viral vector.

DNA or other genetic material may be delivered through viral and non-viral vectors. These vectors can carry exogenous DNA that is used to genetically modify the genome of the rat. For example Adenovirus (AdV), Adeno-associated virus (AAV), and Retrovirus (RV) which contain LTR regions flanking a gene trap, transgene, cassette or interfering RNA are used to integrate and deliver the genetic material. Another delivery method involves non-viral vectors such as plasmids used for electroporation and cationic lipids used for lipofection. The non-viral vectors usually are engineered to have mechanisms for cell uptake, endosome escape, nuclear import, and expression. An example would be a non-viral vector containing a specific nuclear localization sequence and sequence homology for recombination in a targeted region of the genome.

There are a number of compositions and methods which can be used to deliver nucleic acids to cells, either in vitro or in vivo. For example, the nucleic acids can be delivered through a number of direct delivery systems such as, electroporation, lipofection, calcium phosphate precipitation, plasmids, cosmids, or via transfer of genetic material in cells or carriers such as cationic liposomes. Appropriate means for transfection, including chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed non-viral vectors for example, lipids such as liposomes, such as cationic liposomes (e.g., DOTMA, DOPE, DC-cholesterol) or anionic liposome, or polymersomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1:95-100 (1989); Feigner et al. Proc. Natl. Acad. Sci USA 84:7413-7417 (1987); U.S. Pat. No. 4,897,355. Furthermore, the vector can be administered as a component of a microcapsule that can be targeted to specific cell types, such as macrophages, or where the diffusion of the compound or delivery of the compound from the microcapsule is designed for a specific rate or dosage.

In the methods described above, which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

These vectors may be targeted to a particular cell type via antibodies, receptors, or receptor ligands. The following references are examples of the use of this technology to target specific proteins to tumor tissue and are incorporated by reference herein (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). These techniques can be used for a variety of other specific cell types. Vehicles such as "stealth" and other antibody conjugated liposomes (including lipid-mediated drug targeting to colonic carcinoma), receptor-mediated targeting of DNA through cell specific ligands, lymphocyte-directed tumor targeting, and highly specific therapeutic retroviral targeting of murine glioma cells in vivo. The following references are examples of the use of this technology to target specific proteins to tumor tissue and are incorporated by reference herein (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, DNA and Cell Biology 10:6, 399-409 (1991)).

Nucleic acids that are delivered to cells which are to be integrated into the host cell genome typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Ada Domains and Loss of Function Mutations

Rattus norvegicus Adenosine deaminase is a 352 amino acid protein. The protein contains the following active site residues: Leucine (L)-14, Valine (V)-16, Valine (V)-213, Histidine (H)-214, Glycine (G)-216,Glycine (G)-237, Cysteine (C)-269, Serine (S)-294, Aspartic Acid (D)-295-296, and one suspected post-transcriptionally modified site: Alanine (A)-2.

The Ada gene is a 1417 base pair gene with a coding sequence between base pairs 77-1135.

Blackburn et al. (J. Clin. Invest. 112: 332-344, 2003) concluded that over-expression of Il13 inhibits Ada activity, and increases the amount of adenosine accumulation. Further, adenosine induces Il13 activity in Ada−/− mice.

TABLE

Amino Acid changes resulting in SCID
This table displays some amino acid changes that are predicted to disrupt Ada activity.

| SCID | AA change | B-cell | T-cell | NK-cell |
|---|---|---|---|---|
| Full Knockout | Lys(K)80-Arg(R) | — | — | — |
| Full Knockout | Leu(L)304-Arg(R) | — | — | — |
| Full Knockout | Arg(R)101-Trp(W) | — | — | — |
| Full Knockout | Arg(R)101-Gln(Q) | — | — | — |
| Full Knockout | Arg (R)211-His(H) | — | — | — |
| Full Knockout | Val(V)304-Arg(R) | — | — | — |
| Full Knockout | Lys(K)80-Arg ® | — | — | — |
| Full Knockout | Ala(A)329-Val(V) | — | — | — |
| Full Knockout | Leu(L)107-Pro(P) | — | — | — |
| Full Knockout | Gly(G)216-Arg(R) | — | — | — |
| Full Knockout | Ala(A)329-Val(V) | — | — | — |
| Full Knockout | GG-AG transition in intron 10 creates a new splice acceptor site, and a freamshift mutation | | | |
| Full Knockout | G-A transition at the +1 position of the 5' splice joint in exon 2 | — | — | — |
| Partial | Pro(P)297-Gln(Q) | | | |
| Partial | Arg(R)76-Trp(W) | | | |
| Partial | Arg(R)149-Gln(Q) | | | |
| Partial | Pro(P)274-Leu(L) | | | |
| Partial | Arg(R)211-Cys(C) | | | |
| Partial | Ala(A)215-Thr(T) | | | |

The Ada gene is a 1417 base pair gene with a coding sequence between base pairs 77-1135.

TABLE

Amino Acid changes resulting in SCID
Ada phenotypes

The Ada gene encodes the protein Adenosine deaminase (Ada) which catalyzes the irreversible deamination of adenosine and deoxyadenosine in the purine catabolic pathway. Ada plays an critical role in the regulation of B-, T-, and NK-cell maturation, proliferation, and differentiation. Some Ada mutations result in partial loss of function or "knockdown" and others result in full loss of function mutations or "knockout".
The Ada activity resulting from a loss of function in one or several Ada effectors has completely different and variable phenotypes; some resulting in less immunodeficiency and recurrent respiratory infection development or no immunodeficiency and respiratory infection development. Complete loss of function or "knockout" of Ada resulting in loss of function in all of its effectors always results in early onset of impaired cellular immunity, and recurrent respiratory and other organ infections progressing to severe organ incompetence in known animal models.

TABLE

Severe Combined Immunodeficiency Phenotypes

| | B | T | IR NK Sensitivity | Chromosomal Location | Homozygous phenotype |
|---|---|---|---|---|---|
| Rag1 | | | | | |
| Complete loss of function, Knockout, null, Rag1 −/− | − | − | + None | 3q31 | The thymus will contain fewer cells along with nonerythroid cells in the spleen leading to small lymphoid organs at 3-9 weeks. Thymocytes will be larger than heterozygous and WT rats, and lymphocyte development is interrupted at an immature age. B- and T- cell differentiation will not occur, and the rats will have no mature B- and T-cells in lymphoid organs. Rag1 deficient rats will show no V(D)J rearrangements at age 4-7 weeks. The lack of V(D)J recombination being the cause of non-mature B- and T-lymphocytes and SCID phenotype. Only immune system organs, lymphocytes (spleen, thymus, lymph nodes) will lack cells. Other organs will appear normal and both female and male rats will be fertile. |
| Rag2 | | | | | |
| Complete loss of function, Knockout, Null, Rag2−/− | − | − | + None | 3q31 | The thymus and spleen of Rag2−/− rats will be fewer cells. B-cell differentiation and maturation will be blocked at an early stage; which will be at or near the point of Ig gene and onset of VDJ rearrangement. Lack of Ig rearrangments will lead to rats that contain no mature B-cells. No mature T-cells will be found as developing thymocyes are arrested at an early stage. No D(J) rearrangements will be detected in Rag2 −/− rats. There will be a complete lack of rearrangement at the TCR locus. Only immune system organs, lymphocytes (spleen, thymus, lymph nodes) will lack cells. Other organs will appear normal and both female and male rats will be fertile. |
| Ada | − | − | − None | 3q42 | In Ada−/− rats the thymus and spleen exhibits greater than 50% organ-to-body weight reduction. In the thymus, decrease in cortical-medullary demarcation and the Hassel's corpuscles is absent. Spleen, a decreased amount of red blood cells in the red pulp and megakaryocytes. An 8-fold decrease of lymphoid cells in the thymus; a 3-fold decrease in the spleen. In the peripheral circulation lymphophenia with one third of the lymphoid cells in circulation. The serum displayed a 3-fold decrease of overall |

TABLE-continued

Severe Combined Immunodeficiency Phenotypes

| | B | T | NK | IR Sensitivity | Chromosomal Location | Homozygous phenotype |
|---|---|---|---|---|---|---|
| Dclre1c | − | − | + | Yes | 17q12.3 | immunoglobin. Thymus, increase in Cd4−/Cd8− double negative immature thymocytes and a decrease in double positive and single positive. Spleen, there was a decrease in Cd4+ and Cd8+ T- and B- lymphocytes. Dclre1c deficient rats will show defects in opening and joining V(D)J-coding hairpin ends and increased cellular ionizing radiation sensitivity. |
| Nhej1 | − | − | + | Yes, with microcephaly and growth retardation | 9q33 | Nhej1 deficient rats will have impairments in ability to form both V(D)J coding joins and joins of their flanking recombination signal sequences. They will be highly sensitive to ionizing radiation and have DNA Double strand break (DSB) repair defects. |
| Jak3 | + | − | − | None | 16p14 | Jak3 deficient rats will show severe B-cell development defects at the pre-B stage. T-cell development will progress normally, but in response to mitogenic signals T-cells will not proliferate and will secrete small amounts of Il-2. |
| Il7r | + | − | + | None | 2q16 | Il7 deficient rats will have a significant reduction in thymic and peripheral lymphoid cellularity. |
| Ptprc (Cd45) | + | − | + | | 13q13 | Fever, rash, hepatosplenomegaly, lymphadenopathy, pneumonitis, pancytopenia, and cytomegalovirus infection. Low T-cell count, decreased immunoglobulins, and abnormal Cd45, Cd3d, Cd3e expression |
| Cd3d | + | − | + | | 8q22 | Cd3d−/− rats exhibit fever, rash, hepatosplenomegaly, lymphadenopathy, pneumonitis, pancytopenia, and cytomegalovirus infection. Low T-cell count, decreased immunoglobulins, and abnormal Cd45, Cd3d, Cd3e expression |
| Cd3e | + | − | + | | 8q22 | Cd3e−/− rats exhibit fever, rash, hepatosplenomegaly, lymphadenopathy, pneumonitis, pancytopenia, and cytomegalovirus infection. Low T-cell count, decreased immunoglobulins, and abnormal Cd45, Cd3d, Cd3e expression |
| Il2rg | + | − | − | Yes | Xq31 | Rats deficient in Il2rg will have the absolute number of lymphocytes reduced to around 10-fold of WT. |
| Prkdc | − | − | + | None | 11q23 | Prkdc deficient rats will exhibit lymphopenia, hypogammaglobulinemia, and impaired immune functions mediated by T- and B- lymphocytes. |

CLUSTAL 2.0.10 multiple sequence alignment of rat (SEQ ID NO: 1) and mouse (SEQ ID NO: 2) Adenosine Deaminase (Ada) amino acid sequence. The sequence alignment shows close homology between the mouse and rat Ada sequence. The homology of conserved domains and knowledge of insertion mutagenesis allows evidence that mutagenesis will create a total knockout rat Ada.

```
Rattus    MAQTPAFNKPKVELHVHLDGAIKPETILYYGKKRGIDLPADTVEGLRNIIGMDKPLSLPD    60
Mus       MAQTPAFNKPKVELHVHLDGAIKPETILYFGKKRGIALPADTVEELRNIIGMDKPLSLPG    60
          *****************************:****** *******.**************.

Rattus    FLAKFDYYMPAIAGCREAIKRIAYEFVEMKAKEGVVYVEVRYSPHLLANSKVDPIPWNQA   120
Mus       FLAKFDYYMPVIAGCREAIKRIAYEFVEMKAKEGVVYVEVRYSPHLLANSKVDPMPWNQT   120
          **********.***********************************************:

Rattus    EGDLTPDEVVDLVNQGLQEGEQAFGIKVRSILCCMRHQPSWSPEVLELCKKYHQKTVVAM   180
Mus       EGDVTPDDVVDLVNQGLQEGEQAFGIKVRSILCCMRHQPSWSLEVLELCKKYNQKTVVAM   180
          ***:***:*********************************:.*********:*******

Rattus    DLAGDETIEGSSLFPGHVEAYEGAVKDGIHRTVHAGEVGSAEVVREAVDILKTERVGHGY   240
Mus       DLAGDETIEGSSLFPGHVEAYEGAVKNGIHRTVHAGEVGSPEVVREAVDILKTERVGHGY   240
          *************************:.*************.******************

Rattus    HTIEDEALYNRLLKENMHFEVCPWSSYLTGAWNPKTTHAVVRFKDDQANYSLNSDDPLIF   300
Mus       HTIEDEALYNRLLKENMHFEVCPWSSYLTGAWDPKTTHAVVRFKNDKANYSLNTDDPLIF   300
          ********************************:***********:*:******:******

Rattus    KSTVDTDYQMVKKDMGFTEEEFKRLNINAAKSSFLPEDEKKELLERLYKEYQ          352
Mus       KSTLDTDYQMTKKDMGFTEEEFKRLNINAAKSSFLPEEEKKELLERLYREYQ          352
          ***:******.*********************:**********:***
```

Adenosine Deaminase (Ada−/−) Knockout, complete loss of function phenotypes

Blackburn et al. (PNAS 92: 9, 3673-7, 1995) created Ada −/− KO mice by introducing an Ada gene trap which contained the neomycin resistance and herpes simplex tk genes for selection. The mutation resulted in a null Ada allele. The thymus and spleen of Ada −/− KO mice exhibited greater than 50% organ-to-body weight reduction. In the thymus, there was a decrease in cortical-medullary demarcation and the Hassel's corpuscles were absent. In the spleen, a decreased amount of red blood cells in the red pulp and a minuscule amount of megakaryocytes were present. There was an 8-fold decrease of lymphoid cells in the thymus, and a 3-fold decrease in the spleen. In the peripheral circulation, lymphophenia existed with only one-third of the normal number of lymphoid cells in the circulation. The serum displayed a more than 3-fold decrease of overall immunoglobin. In the thymus, there was a significant increase in Cd4−/Cd8− double negative immature thymocytes and a decrease in double positive and single positive thymocytes. In the spleen there was a decrease in Cd4+ and Cd8+T- and B-lymphocytes. T- and B-cell lymphopenia and hypogammaglobulinemia were consequences of Ada deficiency. These data, along with the sudden and severe decrease in immune system competency and health, leading to death (around an age of 3 weeks), indicates that the Adenosine Deaminase (Ada−/−) KO deficiency is a severe combined immunodeficiency (SCID) phenotype.

Adenosine Deaminase (Ada) knockdown, partial loss of function phenotype.

Blackburn et al. (J Biol Chem. 273: 9:5093-100, 1998) created partial Ada-deficient mice by intercrossing male mice which were homozygous for the null Ada allele with female mice which were heterozygous for the null Ada allele. These partial Ada-deficient mice only expressed Ada in the gastrointestinal organs. The partial Ada−/− mice exhibit a much slower progression of symptoms than the complete Ada−/− KO mice. At 6 weeks of age, the lungs accumulated macrophages in the alveolar spaces. At 10 weeks lungs of partial Ada−/− mice exhibited severe inflammation, activated alveolar macrophages, perivascular and peribrochial accumulation of leukocytes and alveolitis. At 12 weeks of age, the lungs demonstrated capacious bronchial plugging. Further, the partial Ada−/− mice have an increased level of lung Adenosine that increases with age and progression of phenotype. These data, demonstrate that the partial Ada−/− mice phenotype is one of slower progression and less pronounced immunodeficiency than the complete Ada−/− knockout phenotype.

Conditional SCID Phenotype

Mutations in Ada are responsible for ~20% of the cases of SCID in humans. Human patients have small or absent thymuses and severely depressed populations of T-, B-, and NK-cells (<10% normal levels). Renal, pulmonary, and liver abnormalities are observed as well. Ada Knockout (KO) mice exhibit lethality due to defects unrelated to the immunodeficiency, namely, severe liver dysfunction. Ada KO rats exhibit similar liver defects leading to early death. It would be preferable to modulate the severe liver defect to facilitate the use of rat Ada KOs for long term propagation of human xenografts for drug discovery or therapeutic studies.

Two strategies can be used to modulate the severity of non-SCID phenotypes:

First, it was found that transgenic mice that express Ada under the transcriptional control of a trophoblast-specific promoter provide ADA activity only during gestation and that severity of the liver defects was modulated. Analysis of the peripheral blood from 15-17 day Ada KO neonates showed that these animals still retained the SCID phenotype.

In SCID patients and in Ada KO mice, injection of ADA enzyme coupled to polyethylene glycol for stabilization (PEG-ADA) was used to treat patients (or KO animals). Interestingly, Ada KO mice exhibit dose-dependent responses to PEG-ADA treatment: at low doses, Ada KO mice are protected from the early lethal defects, such as the severe liver defects, but still retained the SCID phenotype.

The PEG-ADA dosage experiments indicate that any dose-dependent conditional transgenic system that can produce defined levels of ADA enzyme in the ADA (SCID) mutant background would similarly modulate the non-immune defects, and thus create SCID models that would be amenable for long term propagation of human xenografts. An example of such a system, but not limited to this example, are doxycycline-inducible systems (so called tet-on or tet-off systems) which can be used to conditionally complement the non-immune defects, while still maintaining the SCID phenotype.

EXAMPLES

The rat and progenies thereof of the present invention may be any rat or progenies thereof, so long as they are a rat or progenies thereof in which genome is modified so as to have decreased or deleted activity of the severe combined immunodeficiency (SCID) gene.

Gene Disruption Technique which Targets at a Gene Encoding

Adenosine Deaminse (Ada)

The gene disruption method may be any method, so long as it can disrupt the gene of the target enzyme. Examples include a homologous recombination method, a method using retrovirus, a method using DNA transposon, and the like.

(a) Preparation of the rat and progenies thereof of the present invention by homologous recombination The rat and the progenies thereof of the present invention can be produced by modifying a target gene on chromosome through a homologous recombination technique which targets at a gene encoding the SCID gene. The target gene on chromosome can be modified by using a method described in Gene Targeting, A Practical Approach, IRL Press at Oxford University Press (1993) (hereinafter referred to as "Gene Targeting, A Practical Approach"); or the like, for example.

Based on the nucleotide sequence of the genomic DNA, a target vector is prepared for homologous recombination of a target gene to be modified (e.g., structural gene of the SCID gene, or a promoter gene). The prepared target vector is introduced into an embryonic stem cell and a cell in which homologous recombination occurred between the target gene and target vector is selected.

The selected embryonic stem cell is introduced into a fertilized egg according to a known injection chimera method or aggregation chimera method, and the embryonic stem cell-introduced fertilized egg is transplanted into an oviduct or uterus of a pseudopregnant female rat to thereby select germ line chimeras.

The selected germ line chimeras are crossed, and individuals having a chromosome into which the introduced target vector is integrated by homologous recombination with a gene region on the genome which encodes the SCID protein are selected from the born offsprings.

The selected individuals are crossed, and homozygotes having a chromosome into which the introduced target vector is integrated by homologous recombination with a gene region on the genome which encodes the SCID protein in both homologous chromosomes are selected from the born offsprings. The obtained homozygotes are crossed to obtain offspring to thereby prepare the rat and progenies thereof of the present invention.

(b) Preparation of the rat and progenies thereof of the present invention by a method using a transposon The rat and progenies thereof of the present invention can be prepared by using a transposon system similar to that described in Nature Genet., 25, 35 (2000) or the like, and then by selecting a mutant of the SCID gene.

The transposon system is a system in which a mutation is induced by randomly inserting an exogenous gene into chromosome, wherein an gene trap cassette or exogenous gene interposed between transposons is generally used as a vector for inducing a mutation, and a transposase expression vector for randomly inserting the gene into chromosome is introduced into the cell at the same time. Any transposase can be used, so long as it is suitable for the sequence of the transposon to be used. As the gene trap cassette or exogenous gene, any gene can be used, so long as it can induce a mutation in the DNA of the cell.

The rat and progenies thereof of the present invention can be prepared by introducing a mutation into a gene encoding the severe combined immunodeficiency (SCID) associated protein, and then by selecting a rat of interest in which the DNA is mutated.

Specifically, the method includes a method in which a rat of interest in which the mutation occurred in the gene encoding the Ada protein is selected from mutants born from generative cells which are subjected to mutation-inducing treatment or spontaneously generated mutants. In another embodiment, the SCID gene is one of several known SCID genes, such as (Rag1, Rag2, Dclre1c, Nhej1, Jak3, Il7r, Ptprc, Cd3d, Cd3e, Il2rg, Prkdc, Sirpa, Foxn1). The generative cell includes cells capable of forming an individual such as a sperm, an ovum or a pluripotent cells. The generative cell may also be a somatic cell and the animal may then be created by somatic cell nuclear transfer.

Examples in which several methods described above have been employed by the inventors to create a SCID model phenotype in *Rattus norvegicus* are described below.

Genetic modification to *Rattus norvegicus* SCID gene Adenosine Deaminase (Ada) was carried out by a DNA transposon insertional mutagenesis method similar to that described in Nature Genet., 25, 35 (2000). The DNA transposon-mediated genetically modified allele was designated AdaTn(sb-T2/Bart3)2.237Mcwi. The mutant strain symbol for the SCID rat was designated F344-AdaTn(sbT2/Bart3)2.237Mcwi.

The DNA transposon insertion occurred in chromosome 3, within intron 7 of the rat Ada gene. The sequence tag map position was between base pairs: 154638511-154638627. The sequence tag was:

TAGGTTCCTGGGTTCAAACTCAGGTTGTCATGCTTTGTGGAA

GGCACCTTCACCCACTGAGCCATCTTACCAGTTCCAGAATTT

GACACTTGACTTTTCTCAAAGCACTATTCCTAG.

Thus, a DNA transposon was inserted into the Ada gene of *Rattus norvegicus* rendering the gene completely inactive. Adenosine Deaminase (Ada–/–) KO rats have no mature B-, T-, or NK cells. There was an accumulation of 2-deoxyadenosine and dATP, and a decreased level of S-adenosylhomocysteine hydrolase in immune organs. The phenotype was that of a Severe Combined Immunodeficient (SCID) rat.

The practice of the present invention will employ, unless otherwise indicated, conventional techniques of molecular biology (including recombinant techniques), microbiology, cell biology and biochemistry, which are within the skill of the art.

The invention claimed is:

1. A genetically engineered rat, or progeny of the rat, whose genome comprises a homozygous knock-out of the interleukin 2 receptor subunit gamma (Il2rg) gene and a homozygous knock-out of the recombination activating gene 1 (Rag 1) gene, wherein the rat or its progeny exhibits Severe Combined Immunodeficiency (SCID), wherein the rat or its progeny has decreased levels of mature T-cells, B-cells and NK-cells, as compared to a rat not comprising the knock-out of the Il2rg gene and the knock-out of the Rag1 gene.

2. The genetically engineered rat, or progeny of the rat, of claim 1, wherein the rat or its progeny lacks mature B-cells, T-cells, and NK-cells.

3. The genetically engineered rat, or progeny of the rat, of claim 1 wherein the rat or its progeny is capable of accepting a xenograft without eliciting an immune response.

4. The genetically engineered rat, or progeny of the rat, of claim 3, wherein the xenograft is a tumor xenograft or healthy tissue xenograft.

5. The genetically engineered rat, or progeny of the rat, of claim 3, wherein the xenograft is from human lymphoid or myeloid tissues.

6. The genetically engineered rat, or progeny of the rat, of claim 3, wherein the xenograft is from human peripheral blood lymphocytes.

7. The genetically engineered rat, or progeny of the rat, of claim 3, wherein the xenograft is from human thymus.

8. The genetically engineered rat, or progeny of the rat, of claim 3, wherein the xenograft is from human liver tissue.

9. The genetically engineered rat, or progeny of the rat, of claim 1, wherein the rat or its progeny comprises a xenograft.

10. The genetically engineered rat, or progeny of the rat, of claim 9, wherein the xenograft is a tumor xenograft or healthy tissue xenograft.

11. The genetically engineered rat, or progeny of the rat, of claim 9, wherein the xenograft is from human lymphoid or myeloid tissues.

12. The genetically engineered rat, or progeny of the rat, of claim 9, wherein the xenograft is from human peripheral blood lymphocytes.

13. The genetically engineered rat, or progeny of the rat, of claim 9, wherein the xenograft is from human thymus.

14. The genetically engineered rat, or progeny of the rat, of claim 9, wherein the xenograft is from human liver tissue.

15. The genetically engineered rat, or progeny of the rat, of claim 1, wherein the rat or its progeny comprises transplanted cells.

16. The genetically engineered rat, or progeny of the rat, of claim 15, wherein the transplanted cells comprise human cells.

17. The genetically engineered rat, or progeny of the rat, of claim 15, wherein the transplanted cells comprise human hepatic cells.

18. The genetically engineered rat, or progeny of the rat, of claim 15, wherein the transplanted cells comprise primary cells, secondary cells, or a combination thereof.

19. The genetically engineered rat, or progeny of the rat, of claim 18, wherein the primary cells comprise primary cells from healthy subjects, or primary cells from subjects with genetic lesions associated with disease states.

20. The genetically engineered rat, or progeny of the rat, of claim 15, wherein the transplanted cells comprise stem cells.

21. The genetically engineered rat, or progeny of the rat, of claim 20, wherein the stem cells comprise embryonic cells, hematopoietic stem cells, amniotic cells, umbilical cord cells, mesenchymal stem cells, hepatic cells, adipose stromal cells, or induced pluripotent cells.

* * * * *